(12) United States Patent
Fang et al.

(10) Patent No.: US 11,622,547 B2
(45) Date of Patent: Apr. 11, 2023

(54) GENETICALLY MODIFIED MOUSE THAT EXPRESSES HUMAN ALBUMIN

(71) Applicant: Regeneron Pharmaceuticals, Inc., Tarrytown, NY (US)

(72) Inventors: Qing Fang, Chappaqua, NY (US); Chia-Jen Siao, New York, NY (US); Dan Chalothorn, New York, NY (US); KehDih Lai, Yardley, PA (US); Leah Sabin, Goldens Bridge, NY (US); Rachel Sattler, New York, NY (US); Brian Zambrowicz, Sleepy Hollow, NY (US); Lori Morton, Chappaqua, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 239 days.

(21) Appl. No.: 16/894,302

(22) Filed: Jun. 5, 2020

(65) Prior Publication Data

US 2020/0383304 A1    Dec. 10, 2020

Related U.S. Application Data

(60) Provisional application No. 62/916,666, filed on Oct. 17, 2019, provisional application No. 62/858,589, filed on Jun. 7, 2019.

(51) Int. Cl.
| | |
|---|---|
| *A01K 67/027* | (2006.01) |
| *A61K 49/00* | (2006.01) |
| *C07K 14/76* | (2006.01) |
| *C12N 15/85* | (2006.01) |

(52) U.S. Cl.
CPC ...... *A01K 67/0278* (2013.01); *A61K 49/0008* (2013.01); *C07K 14/76* (2013.01); *C12N 15/8509* (2013.01); *A01K 2207/15* (2013.01); *A01K 2227/105* (2013.01); *A01K 2267/03* (2013.01); *C12N 2015/8527* (2013.01)

(58) Field of Classification Search
None
See application file for complete search history.

(56) References Cited

U.S. PATENT DOCUMENTS

| | | | |
|---|---|---|---|
| 5,942,435 A | 8/1999 | Wheeler | |
| 6,586,251 B2 | 7/2003 | Economides et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 9,150,847 B2 | 10/2015 | Rebar | |
| 9,255,250 B2 | 2/2016 | Gregory et al. | |
| 9,394,545 B2 | 7/2016 | Rebar | |
| 9,497,944 B2 | 11/2016 | Daly | |
| 9,732,356 B2 | 8/2017 | Alam et al. | |
| 9,771,403 B2 | 9/2017 | Miller et al. | |
| 9,777,281 B2 | 10/2017 | Rebar | |
| 9,873,894 B2 | 1/2018 | Conway et al. | |
| 9,877,988 B2 | 1/2018 | Rebar | |
| 9,902,974 B2 | 2/2018 | Conway et al. | |
| 9,956,247 B2 | 5/2018 | Rebar | |
| 10,081,661 B2 | 9/2018 | Miller et al. | |
| 10,329,582 B2 | 6/2019 | Lee et al. | |
| 10,385,359 B2 | 8/2019 | Lee et al. | |
| 10,612,041 B2 | 4/2020 | Barzel et al. | |
| 10,767,175 B2 | 9/2020 | Dellinger et al. | |
| 2008/0078000 A1 | 3/2008 | Poueymirou et al. | |
| 2011/0200982 A1 | 8/2011 | Stevens et al. | |
| 2013/0042330 A1 | 2/2013 | Murphy et al. | |
| 2013/0111617 A1 | 5/2013 | MacDonald et al. | |
| 2013/0117873 A1 | 5/2013 | Wang et al. | |
| 2013/0177960 A1 | 7/2013 | Rebar | |
| 2013/0177983 A1 | 7/2013 | Rebar | |
| 2013/0280222 A1 | 10/2013 | Kay et al. | |
| 2013/0340104 A1 | 12/2013 | Murphy | |
| 2014/0017212 A1 | 1/2014 | Rebar | |
| 2014/0112896 A1 | 4/2014 | Rebar | |
| 2014/0134662 A1 | 5/2014 | Flavell et al. | |
| 2014/0155468 A1 | 6/2014 | Gregory et al. | |
| 2014/0178879 A1 | 6/2014 | Economides et al. | |

(Continued)

FOREIGN PATENT DOCUMENTS

| | | |
|---|---|---|
| EP | 2872625 B1 | 11/2016 |
| EP | 3138910 B1 | 9/2017 |

(Continued)

OTHER PUBLICATIONS

Viuff (J. Controlled Release, 2016, vol. 233, p. 22-30).*
Urano (J. Biol. Chem., 1986, vol. 261, No. 7, p. 3244-3251).*
Wang (PNAS, 1997, vol. 94, p. 11563-11566).*
Li (Blood, 2018, vol. 132, Supplement 1, 2458).*
PENG et al., "Production of Human Albumin in Pig Through CRISPR/cas9-Mediated Knockin of Human cDNA into Swine Albumin Locus in the Zygote," Sci. Rep., 5:16705, (2015).

(Continued)

*Primary Examiner* — Michael C Wilson

(74) *Attorney, Agent, or Firm* — Yongjin Choi; Alston & Bird LLP

(57) ABSTRACT

Non-human animal genomes, non-human animal cells, and non-human animals comprising a humanized albumin (ALB) locus and methods of making and using such non-human animal genomes, non-human animal cells, and non-human animals are provided. Non-human animal cells or non-human animals comprising a humanized albumin locus express a human albumin protein or a chimeric albumin protein, fragments of which are from human albumin. Methods are provided for using such non-human animals comprising a humanized albumin locus to assess in vivo efficacy of human-albumin-targeting reagents such as nuclease agents designed to target human albumin.

12 Claims, 12 Drawing Sheets

Specification includes a Sequence Listing.

(56) References Cited

U.S. PATENT DOCUMENTS

| | | |
|---|---|---|
| 2014/0235933 A1 | 8/2014 | Lee et al. |
| 2014/0245467 A1 | 8/2014 | MacDonald et al. |
| 2014/0310828 A1 | 10/2014 | Lee et al. |
| 2014/0335063 A1 | 11/2014 | Cannon et al. |
| 2015/0056705 A1 | 2/2015 | Conway et al. |
| 2015/0106961 A1 | 4/2015 | Rojas et al. |
| 2015/0159172 A1 | 6/2015 | Miller et al. |
| 2015/0166618 A1 | 6/2015 | Miller et al. |
| 2015/0240263 A1 | 8/2015 | Holmes et al. |
| 2015/0313194 A1 | 11/2015 | Hu et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0344893 A1 | 12/2015 | Rebar |
| 2015/0376628 A1 | 12/2015 | Schoenherr et al. |
| 2015/0376651 A1 | 12/2015 | Frendewey et al. |
| 2016/0060656 A1 | 3/2016 | Rebar |
| 2016/0090607 A1 | 3/2016 | Conway et al. |
| 2016/0143953 A1 | 5/2016 | Gregory et al. |
| 2016/0145646 A1 | 5/2016 | Frendewey et al. |
| 2016/0298134 A1 | 10/2016 | Chen et al. |
| 2017/0016027 A1 | 1/2017 | Lee et al. |
| 2017/0119906 A1 | 5/2017 | Riley |
| 2017/0196992 A1 | 7/2017 | Holmes et al. |
| 2017/0245481 A1 | 8/2017 | Gusarova et al. |
| 2017/0342118 A1 | 11/2017 | Miller et al. |
| 2017/0355999 A1 | 12/2017 | Rebar |
| 2018/0110808 A1 | 4/2018 | Rebar |
| 2018/0117181 A1 | 5/2018 | Huston |
| 2018/0139940 A1 | 5/2018 | Macdonald et al. |
| 2018/0185516 A1 | 7/2018 | Ansell et al. |
| 2018/0214490 A1 | 8/2018 | Rebar |
| 2018/0243450 A1 | 8/2018 | Devalaraja-Narashimha et al. |
| 2018/0362601 A1 | 12/2018 | Miller et al. |
| 2019/0002869 A1 | 1/2019 | Yin et al. |
| 2019/0010490 A1 | 1/2019 | Cowan et al. |
| 2019/0076551 A1 | 3/2019 | Bogorad et al. |
| 2019/0098879 A1 | 4/2019 | Drummond-Samuelson et al. |
| 2019/0112353 A1 | 4/2019 | Yang et al. |
| 2019/0153440 A1 | 5/2019 | Kantardzhieva et al. |
| 2019/0211362 A1 | 7/2019 | Lundberg et al. |
| 2019/0225991 A1 | 7/2019 | Izpisua Belmonte et al. |
| 2019/0247517 A1 | 8/2019 | Brooks |
| 2019/0290783 A1 | 9/2019 | Voronina et al. |
| 2019/0365924 A1 | 12/2019 | Conway et al. |
| 2019/0382798 A1 | 12/2019 | Cowan et al. |
| 2019/0390195 A1 | 12/2019 | Tondera et al. |
| 2020/0015462 A1 | 1/2020 | Murphy et al. |
| 2020/0080082 A1 | 3/2020 | Lundberg et al. |
| 2020/0268906 A1 | 8/2020 | Finn et al. |
| 2020/0270617 A1 | 8/2020 | Finn et al. |
| 2020/0270618 A1 | 8/2020 | Finn et al. |
| 2020/0282079 A1 | 9/2020 | Holmes et al. |
| 2020/0289628 A1 | 9/2020 | Finn et al. |
| 2020/0315149 A1 | 10/2020 | Tang et al. |
| 2020/0318136 A1 | 10/2020 | Wang et al. |
| 2020/0340015 A1 | 10/2020 | Dahlman et al. |
| 2020/0384125 A1 | 12/2020 | Brooks |
| 2020/0385721 A1 | 12/2020 | Lee et al. |
| 2020/0385760 A1 | 12/2020 | Haines et al. |
| 2020/0392541 A1 | 12/2020 | Zhang et al. |
| 2021/0079427 A1 | 3/2021 | Chen et al. |
| 2021/0095316 A1 | 4/2021 | Kim et al. |
| 2021/0187125 A1 | 6/2021 | Brooks |
| 2021/0198696 A1 | 7/2021 | Kong et al. |
| 2021/0348159 A1 | 11/2021 | Brooks et al. |

FOREIGN PATENT DOCUMENTS

| | | |
|---|---|---|
| EP | 3196301 B1 | 10/2018 |
| EP | 3138911 B1 | 12/2018 |
| EP | 2839013 B1 | 8/2020 |
| EP | 3011031 B1 | 9/2020 |
| WO | WO 2013/044008 A2 | 3/2013 |
| WO | WO 2014/011237 A1 | 1/2014 |
| WO | WO 2014/089212 A1 | 6/2014 |
| WO | WO 2014/130706 A1 | 8/2014 |
| WO | WO 2014/172489 A2 | 10/2014 |
| WO | WO 2014/186585 A2 | 11/2014 |
| WO | WO 2015/042557 A1 | 3/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/127439 A1 | 8/2015 |
| WO | WO 2015/200334 A1 | 12/2015 |
| WO | WO 2015/200805 A2 | 12/2015 |
| WO | WO 2016/044745 A1 | 3/2016 |
| WO | WO 2016/081923 A2 | 5/2016 |
| WO | WO 2017/011519 A1 | 1/2017 |
| WO | WO 2017/074526 A1 | 5/2017 |
| WO | WO 2017/077386 A1 | 5/2017 |
| WO | WO 2017/087780 A1 | 5/2017 |
| WO | WO 2017/091512 A1 | 6/2017 |
| WO | WO 2017/093804 A2 | 6/2017 |
| WO | WO 2017/109757 A1 | 6/2017 |
| WO | WO 2017/134529 A1 | 8/2017 |
| WO | WO 2017/141109 A1 | 8/2017 |
| WO | WO 2017/158422 A1 | 9/2017 |
| WO | WO 2018/007871 A1 | 1/2018 |
| WO | WO 2018/013932 A1 | 1/2018 |
| WO | WO 2018/075736 A1 | 4/2018 |
| WO | WO 2018/107026 A1 | 6/2018 |
| WO | WO 2018/126087 A1 | 7/2018 |
| WO | WO 2018/232382 A1 | 12/2018 |
| WO | WO 2019/079527 A1 | 4/2019 |
| WO | WO 2019/113310 A1 | 6/2019 |
| WO | WO 2019/118875 A1 | 6/2019 |
| WO | WO 2019/134561 A1 | 7/2019 |
| WO | WO 2019/140330 A1 | 7/2019 |
| WO | WO 2019/161310 A1 | 8/2019 |
| WO | WO 2019/237069 A1 | 12/2019 |
| WO | WO 2019/246203 A1 | 12/2019 |
| WO | WO 2020/006126 A1 | 1/2020 |
| WO | WO 2020/006131 A2 | 1/2020 |
| WO | WO 2020/006132 A1 | 1/2020 |
| WO | WO 2020/032986 A1 | 2/2020 |
| WO | WO 2020/079033 A1 | 4/2020 |
| WO | WO 2020/081843 A1 | 4/2020 |
| WO | WO 2020/082046 A2 | 4/2020 |
| WO | WO 2020/112908 A2 | 6/2020 |
| WO | WO 2020/168362 A1 | 8/2020 |
| WO | WO 2020/206162 A1 | 10/2020 |
| WO | WO 2020/210552 A1 | 10/2020 |
| WO | WO 2020/241679 A1 | 12/2020 |
| WO | WO 2020/247812 A1 | 12/2020 |
| WO | WO 2021-072115 A1 | 4/2021 |
| WO | WO 2021/083073 A1 | 5/2021 |
| WO | WO 2021/224416 A1 | 11/2021 |

OTHER PUBLICATIONS

Viuff et al., "Generation of a double transgenic humanized neonatal Fc receptor (FcRn)/albumin mouse to study the pharmacokinetics of albumin-lined drugs," J. Control. Release, 223:22-30, (2015).

WIPO Application No. PCT/US2020/036412, PCT International Search Report and Written Opinion of the International Searching Authority dated Sep. 18, 2020.

Zhu et al., "Humanising the mouse genome piece by piece," Nat. Commun. 10(1):1845, (Apr. 23, 2019).

Barthold, "Genetically altered mice: phenotypes, no phenotypes, and Faux phenotypes," Genetica, 122(1):75-88, (2004).

Barzel et al., "Promoterless gene targeting without nucleases ameliorates haemophilia B in mice," Nature, 517:360-364 and Extended Data, (2014).

Birling, et al., "Modeling human disease in rodents by CRISPR/Cas9 genome editing," Mamm. Genome, 28(7-8):291-301, (2017).

Brevini, et al., "No shortcuts to pig embryonic stem cells," Theriogenology, 74(4):544-550, (2010).

Brevini, et al., "Porcine embryonic stem cells: Facts, challenges and hopes," Theriogenology, 68 Suppl. 1:S206-S213, (2007).

Burova, et al., "Characterization of the Anti-PD-1 Antibody REGN2810 and Its Antitumor Activity in Human PD-1 Knock-In Mice," Mol. Cancer Ther., 16(5):861-870, (2017).

(56) References Cited

OTHER PUBLICATIONS

Cao, et al., "Isolation and Culture of Primary Bovine Embryonic Stem Cell Colonies by a Novel Method," J. Exp. Zool. A. Ecol. Genet. Physiol., 311 (5):368-376, (2009).
Clark, et al., "A future for transgenic livestock," Nat. Rev. Genet., 4(10):825-833, (2003).
Dechiara, T.M., et al., "VelociMouse: Fully ES Cell-Derived F0-Generation Mice Obtained from the Injection of ES Cells into Eight-Cell-Stage Embryos," Methods in Molecular Biology, 530(16): 311-324, (2009).
Dennis, "Welfare Issues of Genetically Modified Animals," Ilar J., 43(2):100-109, (2002).
Feng, Bo, "High-efficiency CRISPR-based technology for hemophilia B gene therapy," A-Biotech (Hong Kong) Co. Ltd. (2018).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Harari et al., "Bridging the species divide: transgenic mice humanized for type-I interferon response," PLoS One 9(1):e84259, (2014).
He et al., "Knock-in of large reporter genes in human cells via CRISPR/Cas9-induced homology-dependent and independent DNA repair," Nucleic Acids Research, 44(9):e85, pp. 1-14, (2016).
Herndler-Brandstetter, et al., "Humanized mouse model supports development, function, and tissue residency of human natural killer cells," Proc. Natl. Acad. Sci. U.S.A., 114(45):E9626-E9634, (2017).
Houdebine, "Methods to Generate Transgenic Animals," pp. 31-48 in "Genetic Engineering in Livestock: New Applications and Interdisciplinary Perspectives," Ed. Engelhard et al., (2009).
Jean, et al., "Pluripotent genes in avian stem cells," Dev. Growth Differ., 55(1): 41-51, (2013).
Kawamata, et al., "Generation of genetically modified rats from embryonic stem cells," Proc. Natl. Acad. Sci. U.S.A., 7(32):14223-14228, (2010).
Kumar, et al., "Transgenic Mouse Technology: Principles and Methods," Methods Mol. Biol., 590:335-362, (2009).
Laoharawee et al., "Dose-Dependent Prevention of Metabolic and Neurologic Disease in Murine MPS II by ZFN-Mediated In Vivo Genome Editing," Molecular Therapy, 26(4):1127-1136, (2018).
Lute, et al., "Human CTLA4 knock-in mice unravel the quantitative link between tumor immunity and autoimmunity induced by anti-CTLA-4 antibodies," Blood, 106(9):3127-3133, (2005).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Papapetrou et al., "Gene Insertion Into Genomic Safe Harbors for Human Gene Therapy," Molecular Therapy, 24(4):678-684, (2016).
Paris, et al., "Equine embryos and embryonic stem cells: defining reliable markers of pluripotency," Theriogenology, 74(4): 516-524, (2010).
Porro et al., "Promoterless gene targeting without nucleases rescues lethality of a Crigler-Najjar syndrome mouse model," EMBO Molecular Medicine, 9(10):1346-1355, (2017).
Poueymirou, et al., "F0 generation mice fully derived from gene-targeted embryonic stem cells allowing immediate phenotypic analyses," Nat. Biotechnol., 25(1):91-99, (2007).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Sharma et al., "In vivo genome editing of the albumin locus as a platform for protein replacement therapy," Blood, 126(15):1777-1784 (2015).
Sigmund, "Viewpoint: Are Studies in Genetically Altered Mice Out of Control?," Arterioscler. Thromb. Vasc. Biol., 20(6):1425-1429, (2000).
Valenzuela, et al., "High-throughput engineering of the mouse genome coupled with high-resolution expression analysis," Nat. Biotechnol., 21(6):652-659, (2003).
Wakchaure, et al., "Transgenic Animals: A Review on its Various Dimensions and Applications in Animal Biotechnology," International Journal of Emerging Technology and Advanced Engineering, 5(11):210-213, (2015).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Lloyd, "A knockout mouse resource for the biomedical research community," Ann. N.Y. Acad. Sci., 1245:24-26, (2011).

\* cited by examiner

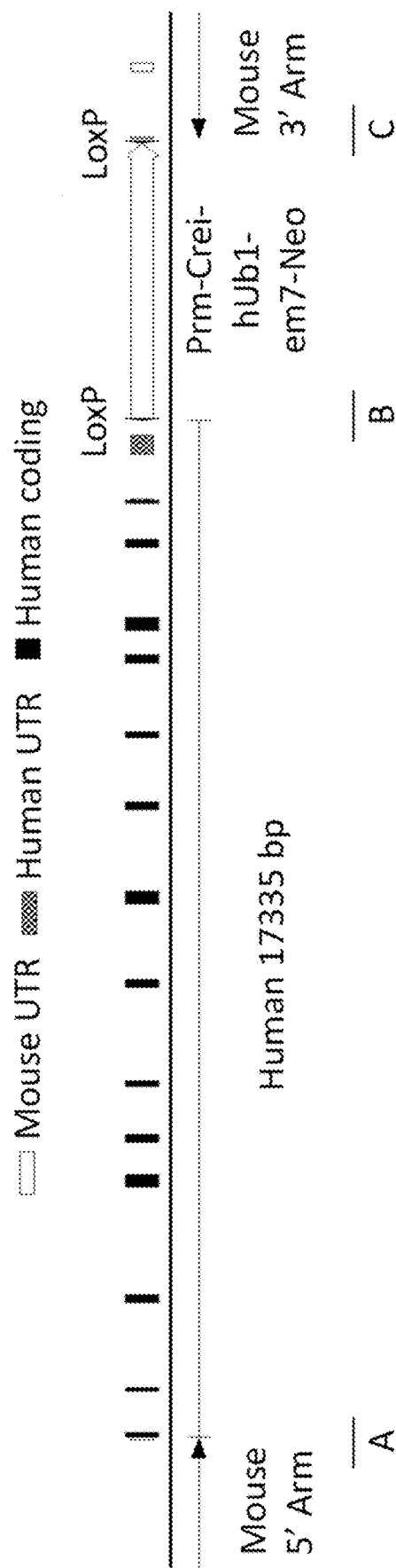
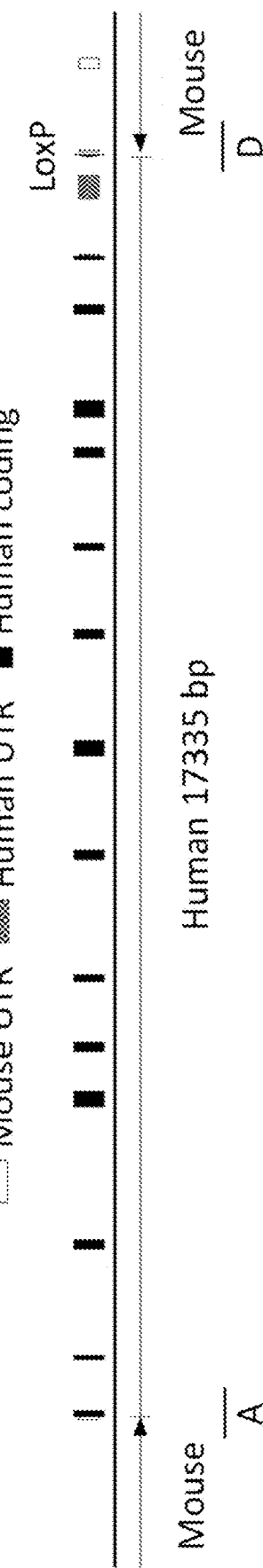
FIG. 1A
FIG. 1B

```
                  Signal peptide   Propeptide              Serum peptide
mouse Alb       1 MKWVTFLLLLFVSGGSAFSRGVFRREAHKSEIAHRYNDLGEQHFKGLVLIAFSQYLQKCSY  60
human ALB       1 MKWVTFISLLFLFSSAYSRGVFRRDAHKSEVAHRFKDLGEENFKALVLIAFAQYLQQCPF  60
7626 HumIn Prot 1 MKWVTFISLLFLFSSAYSRGVFRRDAHKSEVAHRFKDLGEENFKALVLIAFAQYLQQCPF  60
                  **************** **** * ** * * * * mouse Alb      61 DEHAKLVQEVTDFAKTCVADESAANCDKSLHTLFGDKLCAIPNLRENYGELADCCTKQEP 120
human ALB      61 EDHVKLVNEVTEFAKTCVADESAENCDKSLHTLFGDKLCTVATLRETYGEMADCCAKQEP 120
7626 HumIn Prot 61 EDHVKLVNEVTEFAKTCVADESAENCDKSLHTLFGDKLCTVATLRETYGEMADCCAKQEP 120
                    * * ******* ************ * * * *** * mouse Alb     121 ERNECFLQHKDDNPSLPPFERPEAEAMCTSFKENPTTFMGHYLHEVARRHPYFYAPELLY 180
human ALB     121 ERNECFLQHKDDNPNLPRLVRPEVDVMCTAFHDNEETFLKKYLYEIARRHPYFYAPELLF 180
7626 HumIn Prot121 ERNECFLQHKDDNPNLPRLVRPEVDVMCTAFHDNEETFLKKYLYEIARRHPYFYAPELLF 180
                  ************  ***  * *** *   *  * ********** mouse Alb     181 YAEQYNEILTQCCAEADKESCLTPKLDGVKEKALVSSVRQRMKCSSMQKFGERAFKAWAV 240
human ALB     181 FAKRYKAAFTECCQAADKAACLLPKLDELRDEGKASSAKQRLKCASLQKFGERAFKAWAV 240
7626 HumIn Prot181 FAKRYKAAFTECCQAADKAACLLPKLDELRDEGKASSAKQRLKCASLQKFGERAFKAWAV 240
                   *  *   ** * *     **   * * *    *********** mouse Alb     241 ARLSQTFPNADFAEITKLATDLTKVNKECCHGDLLECADDRAELAKYMCENQATISSKLQ 300
human ALB     241 ARLSQRFPKAEFAEVSKLVTDLTKVHTECCHGDLLECADDRADLAKYICENQDSISSKLK 300
7626 HumIn Prot241 ARLSQRFPKAEFAEVSKLVTDLTKVHTECCHGDLLECADDRADLAKYICENQDSISSKLK 300
                  *****  *  **   *** ***********     *** mouse Alb     301 TCCDKPLLKKAHCLSEVEHDTMPADLPAIAADFVEDQEVCKNYAEAKDVFLGTFLYEYSR 360
human ALB     301 ECCEKPLLEKSHCIAEVENDEMPADLPSLAADFVESKDVCKNYAEAKDVFLGMFLYEYAR 360
7626 HumIn Prot301 ECCEKPLLEKSHCIAEVENDEMPADLPSLAADFVESKDVCKNYAEAKDVFLGMFLYEYAR 360
                   ** ****   ** ****   ******  ****** ****************  ****
```

FIG. 3A

```
                        Serum peptide
                       ┌─────────────────────────────────────────────────────────┐
mouse Alb       361    RHPDYSVSLLLRLAKYEATLEKCCAEANPPACYGTVLAEFQPLVEEPKNLVKTNCDLYE   420
human ALB       361    RHPDYSVVLLLRLAKTYETTLEKCCAAADPHECYAKVFDEFKPLVEEPQNLIKQNCELFE   420
7626 HumIn Prot 361    RHPDYSVVLLLRLAKTYETTLEKCCAAADPHECYAKVFDEFKPLVEEPQNLIKQNCELFE   420
                       ********** ** * ******  **** **** * mouse Alb       421    KLGEYGFQNAILVRYTQKAPQVSTPTLVEAARNLGRVGTKCCTLPEDQRLPCVEDYLSAI   480
human ALB       421    QLGEYKFQNALLVRYTKKVPQVSTPTLVEVSRNLGKVGSKCCKHPEAKRMPCAEDYLSVV   480
7626 HumIn Prot 421    QLGEYKFQNALLVRYTKKVPQVSTPTLVEVSRNLGKVGSKCCKHPEAKRMPCAEDYLSVV   480
                       ***  * ******* *  ***    * * * ***** mouse Alb       481    LNRVCLLHEKTPVSEHVTKCCSGSLVERRPCFSALTVDETYVPKEFKAETFTFHSDICTL   540
human ALB       481    LNQLCVLHEKTPVSDRVTKCCTESLVNRPCFSALEVDETYVPKEFNAETFTFHADICTL   540
7626 HumIn Prot 481    LNQLCVLHEKTPVSDRVTKCCTESLVNRPCFSALEVDETYVPKEFNAETFTFHADICTL   540
                       ** * ******* * * *****  ******* *** ** mouse Alb       541    PEKEKQIKKQTALAELVKHKPKATAEQLKTVMDDFAQFLDTCCKAADKDTCFSTEGPNLV   600
human ALB       541    SEKERQIKKQTALVELVKHKPKATKEQLKAVMDDFAAFVEKCCKADDKETCFAEEGKKLV   600
7626 HumIn Prot 541    SEKERQIKKQTALVELVKHKPKATKEQLKAVMDDFAAFVEKCCKADDKETCFAEEGKKLV   600
                        * **** ******  **** * ***  **  * * ** mouse Alb       601    TRCKDALA    608    (SEQ ID NO: 1)
human ALB       601    AASQAALGL   609    (SEQ ID NO: 5)
7626 HumIn Prot 601    AASQAALGL   609    (SEQ ID NO: 5)
                        *  *
```

FIG. 3B

GENETICALLY MODIFIED MOUSE THAT EXPRESSES HUMAN ALBUMIN

CROSS-REFERENCE TO RELATED APPLICATIONS

This application claims the benefit of U.S. Application No. 62/858,589, filed Jun. 7, 2019, and U.S. Application No. 62/916,666, filed Oct. 17, 2019, each of which is herein incorporated by reference in its entirety for all purposes.

REFERENCE TO A SEQUENCE LISTING SUBMITTED AS A TEXT FILE VIA EFS WEB

The Sequence Listing written in file 548195SEQLIST.txt is 158 kilobytes, was created on Jun. 5, 2020, and is hereby incorporated by reference.

BACKGROUND

Gene therapy is a promising therapeutic approach for several human diseases. One approach to gene therapy is insertion of a transgene into a safe harbor locus in the genome. Safe harbor loci include chromosomal loci where transgenes or other exogenous nucleic acid inserts can be stably and reliably expressed in all tissues of interest without overtly altering cell behavior or phenotype. Often, a safe harbor locus is one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

One example of a safe harbor locus is albumin. However, there remains a need for suitable non-human animals providing the true or close approximation of the true human genomic DNA target of human-albumin-targeting reagents at the endogenous albumin locus in vivo, thereby enabling testing of the efficacy and mode of action of such agents in live animals as well as pharmacokinetic and pharmacodynamics studies in a setting where the humanized gene is the only version of albumin present.

SUMMARY

Non-human animals comprising a humanized albumin (ALB) locus are provided, as well as methods of making and using such non-human animals. Non-human animal genomes or cells comprising a humanized albumin (ALB) locus are also provided. Humanized albumin genes are also provided.

In one aspect, provided are non-human animal genomes, non-human animal cells, or non-human animals comprising a humanized albumin (ALB) locus. Such non-human animal genomes, non-human animal cells, or non-human animals can comprise in their genomes a humanized endogenous albumin locus in which a segment of the endogenous albumin locus has been deleted and replaced with a corresponding human albumin sequence.

In some such non-human animal genomes, non-human animal cells, or non-human animals the humanized endogenous albumin locus encodes a protein comprising a human serum albumin peptide. In some such non-human animal genomes, non-human animal cells, or non-human animals the humanized endogenous albumin locus encodes a protein comprising a human albumin propeptide. In some such non-human animal genomes, non-human animal cells, or non-human animals the humanized endogenous albumin locus encodes a protein comprising a human albumin signal peptide.

In some such non-human animal genomes, non-human animal cells, or non-human animals a region of the endogenous albumin locus comprising both coding sequence and non-coding sequence has been deleted and replaced with a corresponding human albumin sequence comprising both coding sequence and non-coding sequence. In some such non-human animal genomes, non-human animal cells, or non-human animals the humanized endogenous albumin locus comprises the endogenous albumin promoter, wherein the human albumin sequence is operably linked to the endogenous albumin promoter. In some such non-human animal genomes, non-human animal cells, or non-human animals at least one intron and at least one exon of the endogenous albumin locus have been deleted and replaced with the corresponding human albumin sequence.

In some such non-human animal genomes, non-human animal cells, or non-human animals the entire albumin coding sequence of the endogenous albumin locus has been deleted and replaced with the corresponding human albumin sequence. Optionally, the region of the endogenous albumin locus from the start codon to the stop codon has been deleted and replaced with the corresponding human albumin sequence.

In some such non-human animal genomes, non-human animal cells, or non-human animals the humanized endogenous albumin locus comprises a human albumin 3' untranslated region. In some such non-human animal genomes, non-human animal cells, or non-human animals the endogenous albumin 5' untranslated region has not been deleted and replaced with the corresponding human albumin sequence.

In some such non-human animal genomes, non-human animal cells, or non-human animals the region of the endogenous albumin locus from the start codon to the stop codon has been deleted and replaced with a human albumin sequence comprising the corresponding human albumin sequence and a human albumin 3' untranslated region, and the endogenous albumin 5' untranslated region has not been deleted and replaced with the corresponding human albumin sequence, and the endogenous albumin promoter has not been deleted and replaced with the corresponding human albumin sequence.

In some such non-human animal genomes, non-human animal cells, or non-human animals the human albumin sequence at the humanized endogenous albumin locus comprises a sequence at least 90%, 95%, 96%, 97%, 98%, 99%, or 100% identical to the sequence set forth in SEQ ID NO: 35. In some such non-human animal genomes, non-human animal cells, or non-human animals the humanized endogenous albumin locus encodes a protein comprising a sequence at least 90%, 95%, 96%, 97%, 98%, 99%, or 100% identical to the sequence set forth in SEQ ID NO: 5. In some such non-human animal genomes, non-human animal cells, or non-human animals the humanized endogenous albumin locus comprises a coding sequence comprising a sequence at least 90%, 95%, 96%, 97%, 98%, 99%, or 100% identical to the sequence set forth in SEQ ID NO: 13. In some such non-human animal genomes, non-human animal cells, or non-human animals the humanized endogenous albumin locus comprises a sequence at least 90%, 95%, 96%, 97%, 98%, 99%, or 100% identical to the sequence set forth in SEQ ID NO: 17 or 18. In some such non-human animal genomes, non-human animal cells, or non-human animals the human albumin sequence at the humanized endogenous albumin locus comprises a sequence at least about 90%, at least about 95%, at least about 96%, at least about 97%, at least about 98%, at least about 99%, or about 100% identical to the sequence set forth in SEQ ID NO: 35. In some such non-human animal genomes, non-human animal cells, or non-human animals the humanized endogenous albumin locus encodes a protein comprising a sequence at least about 90%, at least about 95%, at least about 96%, at least about 97%, at least about 98%, at least about 99%, or about 100% identical to the sequence set forth in SEQ ID NO: 5. In some such non-human animal genomes, non-human animal cells, or non-human animals the humanized endogenous albumin locus comprises a coding sequence comprising a sequence at least about 90%, at least about 95%, at least about 96%, at least about 97%, at least about 98%, at least about 99%, or about 100% identical to the sequence set forth in SEQ ID NO: 13. In some such non-human animal genomes, non-human animal cells, or non-human animals the humanized endogenous albumin locus comprises a sequence at least about 90%, at least about 95%, at least about 96%, at least about 97%, at least about 98%, at least about 99%, or about 100% identical to the sequence set forth in SEQ ID NO: 17 or 18.

In some such non-human animal genomes, non-human animal cells, or non-human animals the humanized endogenous albumin locus does not comprise a selection cassette or a reporter gene.

In some such non-human animal genomes, non-human animal cells, or non-human animals the non-human animal is homozygous for the humanized endogenous albumin locus. In some such non-human animal genomes, non-human animal cells, or non-human animals the non-human animal comprises the humanized endogenous albumin locus in its germline.

In some such non-human animal genomes, non-human animal cells, or non-human animals the non-human animal is a mammal. Optionally, the non-human animal is a rat or mouse. Optionally, the non-human animal is a mouse.

In some such non-human animal genomes, non-human animal cells, or non-human animals, the non-human animal comprises serum albumin levels of at least about 10 mg/mL. In some such non-human animal genomes, non-human animal cells, or non-human animals, serum albumin levels in the non-human animal are at least as high as serum albumin levels in a control non-human animal comprising a wild type albumin locus.

In some such non-human animal genomes, non-human animal cells, or non-human animals, the genome, cell, or animal is heterozygous for the humanized endogenous albumin locus. In some such non-human animal genomes, non-human animal cells, or non-human animals, the genome, cell, or animal is homozygous for the humanized endogenous albumin locus. In some such non-human animal genomes, non-human animal cells, or non-human animals, the genome, cell, or animal further comprises the coding sequence for an exogenous protein integrated into at least one allele of the humanized endogenous albumin locus in one or more cells of the non-human animal. Optionally, the coding sequence for the exogenous protein is integrated into intron 1 of the at least one allele of the humanized endogenous albumin locus (e.g., in the one or more cells of the non-human animal). In some such non-human animal genomes, non-human animal cells, or non-human animals, the genome, cell, or animal further comprises an inactivated endogenous locus that is not the endogenous albumin locus. Optionally, the non-human animal genome, non-human animal cell, or non-human animal further comprises the coding sequence for an exogenous protein integrated into at least one allele of the humanized endogenous albumin locus (e.g., in one or more cells of the non-human animal), wherein the exogenous protein replaces the function of the inactivated endogenous locus. Optionally, the inactivated endogenous locus is an inactivated F9 locus.

In another aspect, providing are targeting vectors for generating the non-human animal genomes, non-human animal cells, or non-human animals described above. Such targeting vectors can be for generating a humanized endogenous albumin locus in which a segment of the endogenous albumin locus has been deleted and replaced with a corresponding human albumin sequence, wherein the targeting vector comprises an insert nucleic acid comprising the corresponding human albumin sequence flanked by a 5' homology arm targeting a 5' target sequence at the endogenous albumin locus and a 3' homology arm targeting a 3' target sequence at the endogenous albumin locus.

In another aspect, provided are methods of assessing the activity of a human-albumin-targeting reagent in vivo. Some such methods comprise: (a) administering the human-albumin-targeting reagent to a non-human animal described above; and (b) assessing the activity of the human-albumin-targeting reagent in the non-human animal.

In some such methods, the administering comprises adeno-associated virus (AAV)-mediated delivery, lipid nanoparticle (LNP)-mediated delivery, or hydrodynamic delivery (HDD). Optionally, the administering comprises LNP-mediated delivery. Optionally, the LNP dose is between about 0.1 mg/kg and about 2 mg/kg. In some such methods, the administering comprises AAV8-mediated delivery.

In some such methods, step (b) comprises isolating a liver from the non-human animal and assessing activity of the human-albumin-targeting reagent in the liver.

In some such methods, the human-albumin-targeting reagent is a genome-editing agent, and the assessing comprises assessing modification of the humanized endogenous albumin locus. Optionally, the assessing comprises measuring the frequency of insertions or deletions within the humanized endogenous albumin locus.

In some such methods, the assessing comprises measuring expression of an albumin messenger RNA encoded by the humanized endogenous albumin locus. In some such methods, the assessing comprises measuring expression of an albumin protein encoded by the humanized endogenous albumin locus. Optionally, assessing expression of the albumin protein comprises measuring serum levels of the albumin protein in the non-human animal. Optionally, assessing expression of the albumin protein comprises measuring expression of the albumin protein in the liver of the non-human animal.

In some such methods, the human-albumin-targeting reagent comprises a nuclease agent designed to target a region of a human albumin gene. In some such methods, the human-albumin-targeting reagent comprises a nuclease agent or a nucleic acid encoding the nuclease agent, wherein the nuclease agent is designed to target a region of a human albumin gene. Optionally, the nuclease agent comprises a Cas protein and a guide RNA designed to target a guide RNA target sequence in the human albumin gene. Optionally, the guide RNA target sequence is in intron 1 of the human albumin gene. Optionally, the Cas protein is a Cas9 protein.

In some such methods, the human-albumin-targeting reagent comprises an exogenous donor nucleic acid, wherein the exogenous donor nucleic acid is designed to target the human albumin gene, and optionally wherein the exogenous donor nucleic acid is delivered via AAV. Optionally, the exogenous donor nucleic acid is a single-stranded oligodeoxynucleotide (ssODN). Optionally, the exogenous donor nucleic acid is capable of insertion into a humanized albumin locus by non-homologous end joining.

In some methods, the exogenous donor nucleic acid does not comprise homology arms. In some methods, the exogenous donor nucleic acid comprises an insert nucleic acid flanked by a 5' homology arm targeting a 5' target sequence at the humanized endogenous albumin locus and a 3' homology arm targeting a 3' target sequence at the humanized endogenous albumin locus. Optionally, each of the 5' target sequence and the 3' target sequence comprises a segment of intron 1 of the human albumin gene.

In some such methods, the exogenous donor nucleic acid encodes an exogenous protein. Optionally, the protein encoded by a humanized endogenous albumin locus that has been targeted with the exogenous donor nucleic acid is a heterologous protein comprising a human albumin signal peptide fused to the exogenous protein. Optionally, the exogenous protein is a factor IX protein. Optionally, the assessing comprises measuring serum levels of the factor IX protein in the non-human animal and/or comprises assessing activated partial thromboplastin time or performing a thrombin generation assay. Optionally, the non-human animal further comprises an inactivated F9 locus, and the assessing comprises measuring serum levels of the factor IX protein in the non-human animal and/or comprises assessing activated partial thromboplastin time or performing a thrombin generation assay. Optionally, the human-albumin-targeting reagent comprises (1) a nuclease agent designed to target a region of a human albumin gene and (2) an exogenous donor nucleic acid, the exogenous donor nucleic acid is designed to target the human albumin gene, the exogenous donor nucleic acid encodes an exogenous protein, and the protein encoded by a humanized endogenous albumin locus that has been targeted with the exogenous donor nucleic acid is a heterologous protein comprising a human albumin signal peptide fused to the exogenous protein. Optionally, the assessing comprises measuring expression of a messenger RNA encoded by the exogenous donor nucleic acid. Optionally, the assessing comprises measuring expression of the exogenous protein. Optionally, assessing expression of the heterologous protein comprises measuring serum levels of the heterologous protein in the non-human animal. Optionally, assessing expression of the heterologous protein comprises measuring expression in the liver of the non-human animal.

In another aspect, provided are methods of optimizing the activity of a human-albumin-targeting reagent in vivo. Some such methods comprise: (I) performing any of the above methods of assessing the activity of a human-albumin-targeting reagent in vivo a first time in a first non-human animal comprising in its genome a humanized endogenous albumin locus; (II) changing a variable and performing the method of step (I) a second time with the changed variable in a second non-human animal comprising in its genome a humanized endogenous albumin locus; and (III) comparing the activity of the human-albumin-targeting reagent in step (I) with the activity of the human-albumin-targeting reagent in step (II), and selecting the method resulting in the higher activity.

In some such methods, the changed variable in step (II) is the delivery method of introducing the human-albumin-targeting reagent into the non-human animal. Optionally, the administering comprises LNP-mediated delivery, and the changed variable in step (II) is the LNP formulation. In some such methods, the changed variable in step (II) is the route of administration of introducing the human-albumin-targeting reagent into the non-human animal. In some such methods, the changed variable in step (II) is the concentration or amount of the human-albumin-targeting reagent introduced into the non-human animal. In some such methods, the changed variable in step (II) is the form of the human-albumin-targeting reagent introduced into the non-human animal. In some such methods, the changed variable in step (II) is the human-albumin-targeting reagent introduced into the non-human animal.

In some such methods, the human-albumin-targeting reagent comprises a Cas protein and a guide RNA designed to target a guide RNA target sequence in a human albumin gene. In some such methods, the human-albumin-targeting reagent comprises a Cas protein or a nucleic acid encoding the Cas protein and a guide RNA or a DNA encoding the guide RNA, wherein the guide RNA is designed to target a guide RNA target sequence in a human albumin gene. Optionally, the changed variable in step (II) is the guide RNA sequence or the guide RNA target sequence. Optionally, the Cas protein and the guide RNA are each administered in the form of RNA, and the changed variable in step (II) is the ratio of Cas mRNA to guide RNA. Optionally, the changed variable in step (II) is guide RNA modifications. Optionally, the human-albumin-targeting reagent comprises a messenger RNA (mRNA) encoding the Cas protein and the guide RNA, and the changed variable in step (II) is the ratio of Cas mRNA to guide RNA.

In some such methods, the human-albumin-targeting reagent comprises an exogenous donor nucleic acid. Optionally, the changed variable in step (II) is the form of the exogenous donor nucleic acid. Optionally, the exogenous donor nucleic acid comprises an insert nucleic acid flanked by a 5' homology arm targeting a 5' target sequence at the humanized endogenous albumin locus and a 3' homology arm targeting a 3' target sequence at the humanized endogenous albumin locus, and the changed variable in step (II) is the sequence or length of the 5' homology arm and/or the sequence or length of the 3' homology arm.

In another aspect, provided are methods of making any of the above non-human animals. Some such methods comprise: (a) introducing into a non-human animal embryonic stem (ES) cell: (i) a nuclease agent that targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human ES cell comprising in its genome the humanized endogenous albumin locus comprising the human albumin sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous albumin locus comprising the human albumin sequence. In another aspect, provided are methods of making any of the above non-human animals. Some such methods comprise: (a) introducing into a non-human animal embryonic stem (ES) cell: (i) a nuclease agent or a nucleic acid encoding the nuclease agent, wherein the nuclease agent targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human ES cell comprising in its genome the humanized endogenous albumin locus comprising the human albumin sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous albumin locus comprising the human albumin sequence. Optionally, the targeting vector is a large targeting vector at least 10 kb in length or in which the sum total of the 5' and 3' homology arms is at least 10 kb in length.

Some such methods comprise: (a) introducing into a non-human animal one-cell stage embryo: (i) a nuclease agent that targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human one-cell stage embryo comprising in its genome the humanized endogenous albumin locus comprising the human albumin sequence; (b) gestating the genetically modified non-human animal one-cell stage embryo in a surrogate mother to produce a genetically modified F0 generation non-human animal comprising in its genome the humanized endogenous albumin locus comprising the human albumin sequence. Some such methods comprise: (a) introducing into a non-human animal one-cell stage embryo: (i) a nuclease agent or a nucleic acid encoding the nuclease agent, wherein the nuclease agent targets a target sequence in the endogenous albumin locus; and (ii) a targeting vector comprising a nucleic acid insert comprising the human albumin sequence flanked by a 5' homology arm corresponding to a 5' target sequence in the endogenous albumin locus and a 3' homology arm corresponding to a 3' target sequence in the endogenous albumin locus, wherein the targeting vector recombines with the endogenous albumin locus to produce a genetically modified non-human one-cell stage embryo comprising in its genome the humanized endogenous albumin locus comprising the human albumin sequence; (b) gestating the genetically modified non-human animal one-cell stage embryo in a surrogate mother to produce a genetically modified F0 generation non-human animal comprising in its genome the humanized endogenous albumin locus comprising the human albumin sequence.

In some such methods, the nuclease agent comprises a Cas protein and a guide RNA. Optionally, the Cas protein is a Cas9 protein. Optionally, step (a) further comprises introducing a second guide RNA that targets a second target sequence within the endogenous albumin locus.

In some such methods, the non-human animal is a mouse or a rat. Optionally, the non-human animal is a mouse.

In another aspect, provided are methods of making any of the above non-human animals. Some such methods comprise: (a) modifying the genome of a pluripotent non-human animal cell to comprise the humanized endogenous albumin locus; (b) identifying or selecting the genetically modified pluripotent non-human animal cell comprising the humanized endogenous albumin locus; (c) introducing the genetically modified pluripotent non-human animal cell into a non-human animal host embryo; and (d) gestating the non-human animal host embryo in a surrogate mother. Some such methods comprise: (a) modifying the genome of a non-human animal one-cell stage embryo to comprise the humanized endogenous albumin locus; (b) selecting the genetically modified non-human animal one-cell stage embryo comprising the humanized endogenous albumin locus; and (c) gestating the genetically modified non-human animal one-cell stage embryo in a surrogate mother.

BRIEF DESCRIPTION OF THE FIGURES

FIG. 1A (not to scale) shows a schematic of the humanized mouse albumin (Alb) locus with the neomycin selection cassette (MAID 7626). The sequences for junctions A, B, and C are set forth in SEQ ID NOS: 19-21, respectively.

FIG. 1B (not to scale) shows a schematic of the humanized mouse albumin (Alb) locus following removal of the neomycin selection cassette (MAID 7627). The sequences for junctions A and D are set forth in SEQ ID NOS: 19 and 22, respectively.

FIGS. 3A and 3B show an alignment of the mouse (mouse Alb), human (human ALB), and humanized (7626 HumIn Prot) albumin proteins. Boxed residues constitute the signal peptide. Dotted lines denote the serum albumin peptide sequence. Heavy solid line denotes the propeptide sequence. All residues in the humanized albumin protein are encoded by introduced human exons.

FIG. 10A shows a TGA-EA profile of human normal and Factor-IX-deficient plasma samples. FIG. 10B shows a TGA-EA profile of mouse plasma from AAV-hF9 insertion in ALB$^{m/hu}$×F9$^{-/-}$ mice.

DEFINITIONS

Figure 2:
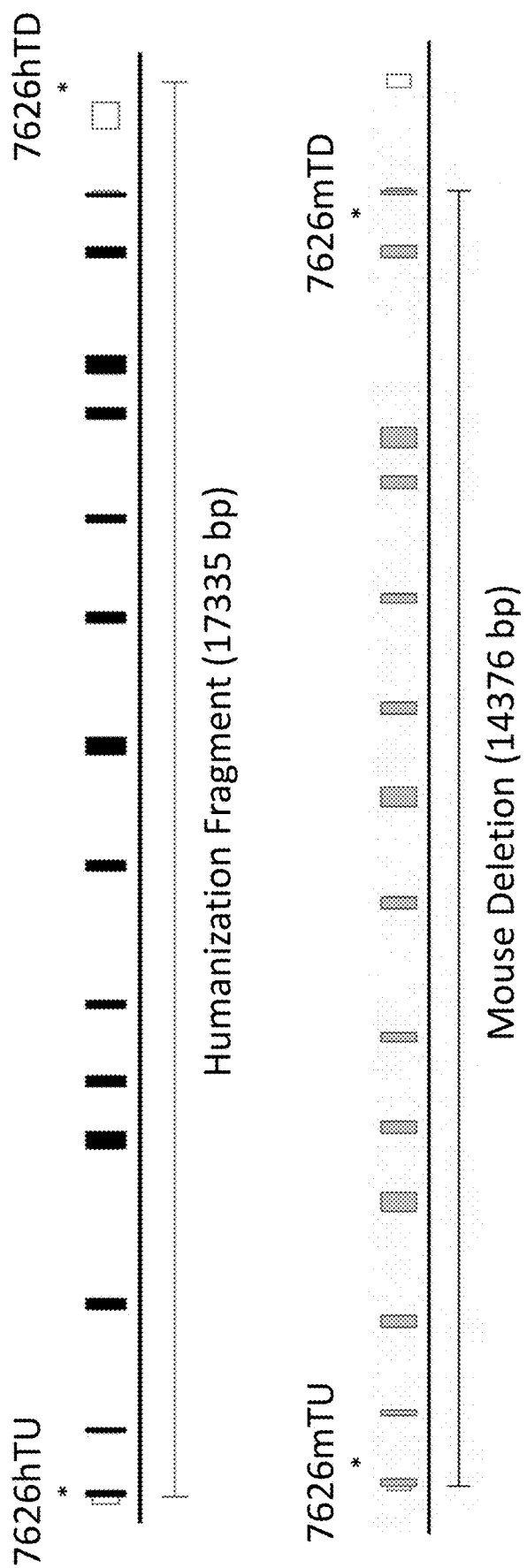
FIG. 2 (not to scale) shows the location of the TAQMAN® probes for screening humanization of the mouse albumin (Alb) locus. Gain-of-allele (GOA) probes include 7626hU and 7626hD. Loss-of-allele (*LOA*) probes include 7626mTU and 7626mTD.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to cells, tissues (e.g., liver samples), proteins, and nucleic acids includes cells, tissues (e.g., liver samples), proteins, and nucleic acids that are relatively purified with respect to other bacterial, viral, cellular, or other components that may normally be present in situ, up to and including a substantially pure preparation of the cells, tissues (e.g., liver samples), proteins, and nucleic acids. The term "isolated" also includes cells, tissues (e.g., liver samples), proteins, and nucleic acids that have no naturally occurring counterpart, have been chemically synthesized and are thus substantially uncontaminated by other cells, tissues (e.g., liver samples), proteins, and nucleic acids, or has been separated or purified from most other components (e.g., cellular components) with which they are naturally accompanied (e.g., other cellular proteins, polynucleotides, or cellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous albumin sequence of a non-human animal refers to a native albumin sequence that naturally occurs at the albumin locus in the non-human animal.

"Exogenous" molecules or sequences include molecules or sequences that are not normally present in a cell in that form or location (e.g., genomic locus). Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form and location in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "albumin locus" or "Alb locus" may refer to the specific location of an albumin (Alb) gene, albumin DNA sequence, albumin-encoding sequence, or albumin position on a chromosome of the genome of an organism that has been identified as to where such a sequence resides. An "albumin locus" may comprise a regulatory element of an albumin gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., $Tm=81.5+0.41(\% G+C)$, although other known Tm computations take into account nucleic acid structural characteristics.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides.

Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J Mol. Biol.* 215:403-410; Zhang and Madden (1997) *Genome Res.* 7:649-656, each of which is herein incorporated by reference in its entirety for all purposes) or by using the Gap program (Wisconsin Sequence Analysis Package, Version 8 for Unix, Genetics Computer Group, University Research Park, Madison Wis.), using default settings, which uses the algorithm of Smith and Waterman (1981) *Adv. Appl. Math.* 2:482-489, herein incorporated by reference in its entirety for all purposes.

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A fragment can be, for example, when referring to a nucleic acid fragment, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p<0.05$.

DETAILED DESCRIPTION

I. Overview

Disclosed herein are non-human animal genomes, non-human animal cells, and non-human animals comprising a humanized albumin (ALB) locus and methods of using such non-human animal cells and non-human animals. Non-human animal cells or non-human animals comprising a humanized albumin locus express a human albumin protein or a chimeric albumin protein comprising one or more fragments of a human albumin protein. Such non-human animal cells and non-human animals can be used to assess delivery or efficacy of human-albumin-targeting agents (e.g., CRISPR/Cas9 genome editing agents) in vitro, ex vivo, or in vivo and can be used in methods of optimizing the delivery of efficacy of such agents in vitro, ex vivo, or in vivo.

In some of the non-human animal cells and non-human animals disclosed herein, most or all of the human albumin genomic DNA is inserted into the corresponding orthologous non-human animal albumin locus. In some of the non-human animal cells and non-human animals disclosed herein, most or all of the non-human animal albumin genomic DNA is replaced one-for-one with corresponding orthologous human albumin genomic DNA. Compared to non-human animals with cDNA insertions, expression levels should be higher when the intron-exon structure and splicing machinery are maintained because conserved regulator elements are more likely to be left intact, and spliced transcripts that undergo RNA processing are more stable than cDNAs. In contrast, insertion of human albumin cDNA into a non-human animal albumin locus would abolish conserved regulatory elements such as those contained within the first exon and intron of the non-human animal albumin. Replacing the non-human animal genomic sequence with the corresponding orthologous human genomic sequence or inserting human albumin genomic sequence in the corresponding orthologous non-human albumin locus is more likely to result in faithful expression of the transgene from the endogenous albumin locus. Similarly, transgenic non-human animals with transgenic insertion of human-albumin-coding sequences at a random genomic locus rather than the endogenous non-human-animal albumin locus will not as accurately reflect the endogenous regulation of albumin expression. A humanized albumin allele resulting from replacing most or all of the non-human animal genomic DNA one-for-one with corresponding orthologous human genomic DNA or inserting human albumin genomic sequence in the corresponding orthologous non-human albumin locus will provide the true human target or a close approximation of the true human target of human-albumin-targeting reagents (e.g., CRISPR/Cas9 reagents designed to target human albumin), thereby enabling testing of the efficacy and mode of action of such agents in live animals as well as pharmacokinetic and pharmacodynamics studies in a setting where the humanized protein and humanized gene are the only version of albumin present.

II. Non-Human Animals Comprising a Humanized Albumin (ALB) Locus

The non-human animal genomes, non-human animal cells, and non-human animals disclosed herein comprise a humanized albumin (ALB) locus. Cells or non-human animals comprising a humanized albumin locus express a human albumin protein or a partially humanized, chimeric albumin protein in which one or more fragments of the native albumin protein have been replaced with corresponding fragments from human albumin. Also disclosed herein are humanized non-human animal albumin genes in which a segment of the non-human albumin gene has been deleted and replaced with a corresponding human albumin sequence.

The non-human animal genomes, non-human animal cells, and non-human animals disclosed herein can further comprise an inactivated (knocked out) endogenous gene that is not the albumin locus. Such non-human animal genomes, non-human animal cells, and non-human animals can be used, for example, to screen gene therapy reagents (e.g., transgenes) for insertion into the humanized albumin locus to replace the inactivated endogenous gene. The insertion into the humanized albumin locus to replace the inactivated endogenous gene can, for example, rescue the knockout. In one specific example, the non-human animal genomes, non-human animal cells, and non-human animals disclosed herein can further comprise an inactivated (knocked out) endogenous F9 gene (encodes coagulating factor IX). An inactivated (knocked out) endogenous F9 gene is one that does not express any coagulation factor IX (also known as Christmas factor, plasma thromboplastin component, or PTC). The wild type human coagulation factor IX protein has been assigned UniProt accession number P00740, and the human F9 gene has been assigned GeneID 2158. The wild type mouse coagulation factor IX protein has been assigned UniProt accession number P16294, and the mouse F9 gene has been assigned GeneID 14071. The wild type rat coagulation factor IX protein has been assigned UniProt accession number P16296, and the rat F9 gene has been assigned GeneID 24946.

The non-human animal genomes, non-human animal cells, and non-human animals disclosed herein can further comprise the coding sequence for an exogenous protein integrated into at least one allele of the humanized albumin locus (e.g., in one or more cells of the non-human animal such as in one or more liver cells in the non-human animal). The coding sequence can be integrated, for example, in intron 1, intron 12, or intron 13 of the humanized albumin locus. In some cases, expression of human albumin from the humanized albumin locus is maintained at the same level following integration of the coding sequence for the exogenous protein into at least one allele of the humanized albumin locus (e.g., in one or more cells of the non-human animal such as in one or more liver cells in the non-human animal). In one example, the non-human animal genome, cell, or animal further comprises an inactivated (knocked out) endogenous gene that is not the albumin locus, and the exogenous protein replaces the function of the inactivated endogenous gene (e.g., rescues the knockout). In one specific example, the exogenous protein is coagulation factor IX (e.g., human coagulation factor IX).

A. Albumin

The cells and non-human animals described herein comprise a humanized albumin (ALB) locus. Albumin is encoded by the ALB gene (also known as albumin, serum albumin, PRO0883, PRO0903, HSA, GIG20, GIG42, PRO1708, PRO2044, PRO2619, PRO2675, and UNQ696/PRO1341). Albumin is synthesized in the liver as preproalbumin, which has an N-terminal peptide that is removed before the nascent protein is released from the rough endoplasmic reticulum. The product, proalbumin, is in turn cleaved in the Golgi vesicles to produce the secreted albumin (serum albumin). Human serum albumin is the serum albumin found in human blood. It is the most abundant protein in human blood plasma; it constitutes about half of serum protein. It is produced in the liver. It is soluble in water and monomeric. Albumin transports hormones, fatty acids, and other compounds, buffers pH, and maintains oncotic pressure, among other functions. Human albumin concentrations in serum are typically approximately 35-50 g/L (3.5-5.0 g/dL). It has a serum half-life of approximately 20 days. It has a molecular mass of 66.5 kDa.

Albumin is considered to be a genomic safe harbor locus because of its very high expression level and the tractability of liver for gene delivery and in vivo editing relative to other tissues. Safe harbor loci include chromosomal loci where transgenes or other exogenous nucleic acid inserts can be stably and reliably expressed in all tissues of interest without overtly altering cell behavior or phenotype. Often, a safe harbor locus is one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

The albumin gene structure is suited for transgene targeting into intronic sequences because its first exon encodes a secretory peptide (signal peptide) that is cleaved from the final protein product. For example, integration of a promoterless cassette bearing a splice acceptor and a therapeutic transgene would support expression and secretion of many different proteins.

Human ALB maps to human 4q13.3 on chromosome 4 (NCBI RefSeq Gene ID 213; Assembly GRCh38.p 12 (GCF_000001405.38); location NC_000004.12 (73404239 . . . 73421484 (+))). The gene has been reported to have 15 exons. Of these, 14 of the exons are coding exon, and exon 15 is a non-coding exon that is part of the 3' untranslated region (UTR). The wild type human albumin protein has been assigned UniProt accession number P02768. At least three isoforms are known (P02768-1 through P02768-3). The sequence for one isoform, P02768-1 (identical to NCBI Accession No. NP_000468.1), is set forth in SEQ ID NO: 5. An mRNA (cDNA) encoding the canonical isoform is assigned NCBI Accession No. NM_000477.7 and is set forth in SEQ ID NO: 37. An exemplary coding sequence (CDS) is assigned CCDS ID CCDS3555.1 and is set forth in SEQ ID NO: 13. The full-length human albumin protein set forth in SEQ ID NO: 5 has 609 amino acids, including a signal peptide (amino acids 1-18), a propeptide (amino acids 19-24), and serum albumin (amino acids 25-609). Delineations between these domains are as designated in UniProt. Reference to human albumin includes the canonical (wild type) forms as well as all allelic forms and isoforms. Any other forms of human albumin have amino acids numbered for maximal alignment with the wild type form, aligned amino acids being designated the same number.

Mouse Alb maps to mouse 5 E1; 5 44.7 cM on chromosome 5 (NCBI RefSeq Gene ID 11657; Assembly GRCm38.p 4 (GCF_000001635.24); location NC_000071.6 (90,460,870 . . . 90,476,602 (+))). The gene has been reported to have 15 exons. Of these, 14 of the exons are coding exon, and exon 15 is a non-coding exon that is part of the 3' untranslated region (UTR). The wild type mouse albumin protein has been assigned UniProt accession number P07724. The sequence for mouse albumin (identical to NCBI Accession No. NP_033784.2), is set forth in SEQ ID NO: 1. An exemplary mRNA (cDNA) isoform encoding the canonical isoform is assigned NCBI Accession No. NM 009654.4 and is set forth in SEQ ID NO: 36. An exemplary coding sequence (CDS) (CCDS ID CCDS19412.1) is set forth in SEQ ID NO: 9. The canonical full-length mouse albumin protein set forth in SEQ ID NO: 1 has 608 amino acids, including a signal peptide (amino acids 1-18), a propeptide (amino acids 19-24) and serum albumin (amino acids 25-608). Delineations between these domains are as designated in UniProt. Reference to mouse albumin includes the canonical (wild type) forms as well as all allelic forms and isoforms. Any other forms of mouse albumin have amino acids numbered for maximal alignment with the wild type form, aligned amino acids being designated the same number.

Albumin sequences for many other non-human animals are also known. These include, for example, bovine (UniProt accession number P02769; NCBI RefSeq Gene ID 280717), rat (UniProt accession number P02770; NCBI RefSeq Gene ID 24186), chicken (UniProt accession number P19121), Sumatran orangutan (UniProt accession number Q5NVH5; NCBI RefSeq Gene ID 100174145), horse (UniProt accession number P35747; NCBI RefSeq Gene ID 100034206), cat (UniProt accession number P49064; NCBI RefSeq Gene ID 448843), rabbit (UniProt accession number P49065; NCBI RefSeq Gene ID 100009195), dog (UniProt accession number P49822; NCBI RefSeq Gene ID 403550), pig (UniProt accession number P08835; NCBI RefSeq Gene ID 396960), Mongolian gerbil (UniProt accession number O35090), rhesus macaque (UniProt accession number Q28522; NCBI RefSeq Gene ID 704892), donkey (UniProt accession number Q5XLE4; NCBI RefSeq Gene ID 106835108), sheep (UniProt accession number P14639; NCBI RefSeq Gene ID 443393), American bullfrog (UniProt accession number P21847), golden hamster (UniProt accession number A6YF56; NCBI RefSeq Gene ID 101837229), and goat (UniProt accession number P85295).

B. Humanized Albumin Loci

A humanized albumin locus is an albumin locus in which a segment of the endogenous albumin locus has been deleted and replaced with an orthologous human albumin sequence. A humanized albumin locus can be an albumin locus in which the entire albumin gene is replaced with the corresponding orthologous human albumin sequence, or it can be an albumin locus in which only a portion of the albumin gene is replaced with the corresponding orthologous human albumin sequence (i.e., humanized). For example, the entire albumin coding sequence at the endogenous albumin locus can be deleted and replaced with the corresponding human albumin sequence. A human albumin sequence corresponding to a particular segment of endogenous albumin sequence refers to the region of human albumin that aligns with the particular segment of endogenous albumin sequence when human albumin and the endogenous albumin are optimally aligned. Optimally aligned refers to the greatest number of perfectly matched residues. The corresponding orthologous human sequence can comprise, for example, complementary DNA (cDNA) or genomic DNA. Optionally, the corresponding orthologous human albumin sequence is modified to be codon-optimized based on codon usage in the non-human animal. Replaced or inserted (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, 8, 9, 10, 11, 12, 13, 14, or all 15 exons of the human albumin gene can be humanized. For example, exons corresponding to all exons (i.e., exons 1-15) of the human albumin gene can be humanized. As another example, exons corresponding to 1, 2, 3, 4, 5, 6, 7, 8, 9, 10, 11, 12, 13, or all 14 coding exons of the human albumin gene can be humanized. For example, exons corresponding to all coding exons (i.e., exons 1-14) of the human albumin gene can be humanized. Likewise, introns corresponding to 1, 2, 3, 4, 5, 6, 7, 8, 9, 10, 11, 12, 13, or all 14 introns of the human albumin gene can be humanized or can remain endogenous. For example, introns corresponding to all of the introns (i.e., introns 1-14) of the human albumin gene can be humanized. Likewise, introns corresponding to 1, 2, 3, 4, 5, 6, 7, 8, 9, 10, 11, 12, or all 13 of the introns between coding exons of the human albumin gene can be humanized or can remain endogenous. For example, introns corresponding to all of the introns between coding exons (i.e., introns 1-13) of the human albumin gene can be humanized. Flanking untranslated regions including regulatory sequences can also be humanized or remain endogenous. For example, the 5' untranslated region (UTR), the 3' UTR, or both the 5' UTR and the 3' UTR can be humanized, or the 5' UTR, the 3' UTR, or both the 5' UTR and the 3' UTR can remain endogenous. One or both of the human 5' and 3' UTRs can be inserted, and/or one or both of the endogenous 5' and 3' UTRs can be deleted. In a specific example, both the 5' UTR and the 3' UTR remain endogenous. In another specific example, the 5' UTR remains endogenous and the 3' UTR is humanized. Depending on the extent of replacement by orthologous sequences, regulatory sequences, such as a promoter, can be endogenous or supplied by the replacing human orthologous sequence. For example, the humanized albumin locus can include the endogenous non-human animal albumin promoter (i.e., the human albumin sequence can be operably linked to the endogenous non-human animal promoter).

One or more or all of the regions encoding the signal peptide, the propeptide, or the serum albumin can be humanized, or one or more of such regions can remain endogenous. Exemplary coding sequences for a mouse albumin signal peptide, propeptide, and serum albumin are set forth in SEQ ID NOS: 10-12, respectively. Exemplary coding sequences for a human albumin signal peptide, propeptide, and serum albumin are set forth in SEQ ID NOS: 14-16, respectively.

For example, all or part of the region of the albumin locus encoding the signal peptide can be humanized, and/or all or part of the region of the albumin locus encoding the propeptide can be humanized, and/or all or part of the region of the albumin locus encoding the serum albumin can be humanized. Alternatively or additionally, all or part of the region of the albumin locus encoding the signal peptide can remain endogenous, and/or all or part of the region of the albumin locus encoding the propeptide can remain endogenous, and/or all or part of the region of the albumin locus encoding the serum albumin can remain endogenous. In one example, all or part of the regions of the albumin locus encoding the signal peptide, propeptide, and serum albumin are humanized. Optionally, the CDS of the humanized region of the albumin locus comprises, consists essentially of, or consists of a sequence that is at least 85%, 90%, 95%, 96%, 97%, 98%, 99%, or 100% identical to SEQ ID NO: 13 (or degenerates thereof). Optionally, the CDS of the humanized region of the albumin locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 13 (or degenerates thereof). Optionally, the humanized region of the albumin locus comprises, consists essentially of, or consists of a sequence that is at least 85%, 90%, 95%, 96%, 97%, 98%, 99%, or 100% identical to SEQ ID NO: 35. Optionally, the humanized region of the albumin locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 35. Optionally, the humanized albumin locus encodes a protein that comprises, consists essentially of, or consists of a sequence that is at least 85%, 90%, 95%, 96%, 97%, 98%, 99%, or 100% identical to SEQ ID NO: 5. Optionally, the humanized albumin locus encodes a protein that comprises, consists essentially of, or consists of a sequence that is at least about 85%, at least about 90%, at least about 95%, at least about 96%, at least about 97%, at least about 98%, at least about 99%, or about 100% identical to SEQ ID NO: 5. Optionally, the humanized albumin locus comprises, consists essentially of, or consists of a sequence that is at least 85%, 90%, 95%, 96%, 97%, 98%, 99%, or 100% identical to SEQ ID NO: 17 or 18. Optionally, the humanized albumin locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 17 or 18.

The albumin protein encoded by the humanized albumin locus can comprise one or more domains that are from a human albumin protein and/or one or more domains that are from an endogenous (i.e., native) albumin protein. Exemplary amino acid sequences for a mouse albumin signal peptide, propeptide, and serum albumin are set forth in SEQ ID NOS: 2-4, respectively. Exemplary amino acid sequences for a human albumin signal peptide, propeptide, and serum albumin are set forth in SEQ ID NOS: 6-8, respectively.

The albumin protein can comprise one or more or all of a human albumin signal peptide, a human albumin propeptide, and a human serum albumin. Alternatively or additionally, the albumin protein can comprise one or more domains that are from the endogenous (i.e., native) non-human animal albumin protein. For example, the albumin protein can comprise a signal peptide from the endogenous (i.e., native) non-human animal albumin protein and/or a propeptide from the endogenous (i.e., native) non-human animal albumin protein and/or a serum albumin from the endogenous (i.e., native) non-human animal albumin protein and/or. As one example, the albumin protein can comprise a human signal peptide, propeptide, and serum albumin.

Domains in a chimeric albumin protein that are from a human albumin protein can be encoded by a fully humanized sequence (i.e., the entire sequence encoding that domain is replaced with the orthologous human albumin sequence) or can be encoded by a partially humanized sequence (i.e., some of the sequence encoding that domain is replaced with the orthologous human albumin sequence, and the remaining endogenous (i.e., native) sequence encoding that domain encodes the same amino acids as the orthologous human albumin sequence such that the encoded domain is identical to that domain in the human albumin protein). Likewise, domains in a chimeric protein that are from the endogenous albumin protein cay be encoded by a fully endogenous sequence (i.e., the entire sequence encoding that domain is the endogenous albumin sequence) or can be encoded by a partially humanized sequence (i.e., some of the sequence encoding that domain is replaced with the orthologous human albumin sequence, but the orthologous human albumin sequence encodes the same amino acids as the replaced endogenous albumin sequence such that the encoded domain is identical to that domain in the endogenous albumin protein).

As one example, the albumin protein encoded by the humanized albumin locus can comprise a human albumin signal peptide. Optionally, the human albumin signal peptide comprises, consists essentially of, or consists of a sequence that is at least 85%, 90%, 95%, 96%, 97%, 98%, 99%, or 100% identical to SEQ ID NO: 6. Optionally, the human albumin signal peptide comprises, consists essentially of, or consists of a sequence that is at least about 85%, at least about 90%, at least about 95%, at least about 96%, at least about 97%, at least about 98%, at least about 99%, or about 100% identical to SEQ ID NO: 6. As another example, the albumin protein encoded by the humanized albumin locus can comprise a human albumin propeptide. Optionally, the human albumin propeptide comprises, consists essentially of, or consists of a sequence that is at least 85%, 90%, 95%, 96%, 97%, 98%, 99%, or 100% identical to SEQ ID NO: 7. Optionally, the human albumin propeptide comprises, consists essentially of, or consists of a sequence that is at least about 85%, at least about 90%, at least about 95%, at least about 96%, at least about 97%, at least about 98%, at least about 99%, or about 100% identical to SEQ ID NO: 7. As another example, the albumin protein encoded by the humanized albumin locus can comprise a human serum albumin. Optionally, the human serum albumin comprises, consists essentially of, or consists of a sequence that is at least 85%, 90%, 95%, 96%, 97%, 98%, 99%, or 100% identical to SEQ ID NO: 8. Optionally, the human serum albumin comprises, consists essentially of, or consists of a sequence that is at least about 85%, at least about 90%, at least about 95%, at least about 96%, at least about 97%, at least about 98%, at least about 99%, or about 100% identical to SEQ ID NO: 8. For example, the albumin protein encoded by the humanized albumin locus can comprise, consist essentially of, or consist of a sequence that is at least 85%, 90%, 95%, 96%, 97%, 98%, 99%, or 100% identical to SEQ ID NO: 5. For example, the albumin protein encoded by the humanized albumin locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 5. Optionally, the albumin CDS encoded by the humanized albumin locus can comprise, consist essentially of, or consist of a sequence that is at least 85%, 90%, 95%, 96%, 97%, 98%, 99%, or 100% identical to SEQ ID NO: 13 (or degenerates thereof). Optionally, the albumin CDS encoded by the humanized albumin locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 13 (or degenerates thereof).

The humanized albumin protein can retain the activity of the native albumin protein and/or the human albumin protein.

Optionally, a humanized albumin locus can comprise other elements. Examples of such elements can include selection cassettes, reporter genes, recombinase recognition sites, or other elements. Alternatively, the humanized albumin locus can lack other elements (e.g., can lack a selection marker or selection cassette). Examples of suitable reporter genes and reporter proteins are disclosed elsewhere herein. Examples of suitable selection markers include neomycin phosphotransferase (neo_r), hygromycin B phosphotransferase (hyg_r), puromycin-N-acetyltransferase (puro_r), blasticidin S deaminase (bsr_r), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized albumin locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

One exemplary humanized albumin locus (e.g., a humanized mouse albumin locus) is one in which a region from the start codon through the stop codon is replaced with the corresponding human sequence. See FIGS. 1A and 1B and SEQ ID NOS: 17 and 18. In a specific example, a region from the ATG start codon through the stop codon (i.e., coding exons 1-14) can be deleted from the non-human animal (e.g., mouse) albumin (Alb) locus, and a corresponding region of the human albumin (ALB) from the ATG start codon to about 100 bp downstream of the stop codon can be inserted in place of the deleted endogenous region.

C. Non-Human Animal Genomes, Non-Human Animal Cells, and Non-Human Animals Comprising a Humanized Albumin (ALB) Locus Non-human animal genomes, non-human animal cells, and non-human animals comprising a humanized albumin (ALB) locus as described elsewhere herein are provided. The genomes, cells, or non-human animals can be male or female. The genomes, cells, or non-human animals can be heterozygous or homozygous for the humanized albumin locus. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized albumin locus can comprise the humanized endogenous albumin locus in its germline.

The non-human animal genomes or cells provided herein can be, for example, any non-human animal genome or cell comprising an albumin locus or a genomic locus homologous or orthologous to the human albumin locus. The genomes can be from or the cells can be eukaryotic cells, which include, for example, fungal cells (e.g., yeast), plant cells, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized albumin locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal wN, C57BL/6, C57BL/6J, C57BL/6ByJ, C57BL/6NJ, C57BL/10, C57BL/10ScSn, C57BL/10Cr, and C57BL/01a. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

Non-human animals (e.g., mice or rats) comprising a humanized albumin locus (e.g., a homozygous humanized albumin locus) can express albumin from the humanized albumin locus such that serum albumin levels (e.g., serum human albumin levels) are comparable to serum albumin levels in control wild type non-human animals. In one example, non-human animals comprising a humanized albumin locus (e.g., a homozygous humanized albumin locus) can have serum albumin levels (e.g., serum human albumin levels) that are at least about 75%, at least about 80%, at least about 85%, at least about 90%, at least about 95%, or at least about 100% of serum albumin levels in a control wild type non-human animal. In another example, non-human animals comprising a humanized albumin locus (e.g., a homozygous humanized albumin locus) can have serum albumin levels (e.g., serum human albumin levels) that are at least as high as serum albumin levels in a control wild type non-human animal. In another example, non-human animals comprising a humanized albumin locus (e.g., a homozygous humanized albumin locus) can have serum albumin levels (e.g., serum human albumin levels) that are higher than serum albumin levels in a control wild type non-human animal. For example, a non-human animal comprising a humanized albumin locus (e.g., a homozygous humanized albumin locus) can have serum albumin levels (e.g., serum human albumin levels) of at least about 1 mg/mL, at least about 2 mg/mL, at least about 3 mg/mL, at least about 4 mg/mL, at least about 5 mg/mL, at least about 6 mg/mL, at least about 7 mg/mL, at least about 8 mg/mL, at least about 9 mg/mL, at least about 10 mg/mL, at least about 11 mg/mL, at least about 12 mg/mL, at least about 13 mg/mL, at least about 14 mg/mL, or at least about 15 mg/mL. In a more specific example, the non-human animal comprising a humanized albumin locus (e.g., a homozygous humanized albumin locus) can be a mouse and can have serum albumin levels (e.g., serum human albumin levels) of at least about 1 mg/mL, at least about 2 mg/mL, at least about 3 mg/mL, at least about 4 mg/mL, at least about 5 mg/mL, at least about 6 mg/mL, at least about 7 mg/mL, at least about 8 mg/mL, at least about 9 mg/mL, at least about 10 mg/mL, at least about 11 mg/mL, at least about 12 mg/mL, at least about 13 mg/mL, at least about 14 mg/mL, or at least about 15 mg/mL. In a specific example, the non-human animal (e.g., a mouse) comprising a humanized albumin locus (e.g., a homozygous humanized albumin locus) can have serum albumin levels (e.g., serum human albumin levels) of between about 10 mg/mL and about 15 mg/mL. In any of the above examples, the albumin encoded by the humanized albumin locus can comprise, for example, a human albumin signal peptide. For example, in one example, the entire albumin coding sequence of the endogenous albumin locus has been deleted and replaced with the corresponding human albumin sequence or the region of the endogenous albumin locus from the start codon to the stop codon has been deleted and replaced with the corresponding human albumin sequence.

III. Methods of Using Non-Human Animals Comprising a Humanized Albumin Locus for Assessing Efficacy of Human-Albumin-Targeting Reagents In Vivo or Ex Vivo Various methods are provided for using the non-human animals comprising a humanized albumin locus as described elsewhere herein for assessing or optimizing delivery or efficacy of human-albumin-targeting reagents (e.g., therapeutic molecules or complexes) in vivo or ex vivo. Because the non-human animals comprise a humanized albumin locus, the non-human animals will more accurately reflect the efficacy of a human-albumin-targeting reagent. Such non-human animals are particularly useful for testing genome-editing reagents designed to target the human albumin gene because the non-human animals disclosed herein comprise humanized endogenous albumin loci rather than transgenic insertions of human albumin sequence at random genomic loci, and the humanized endogenous albumin loci can comprise orthologous human genomic albumin sequence from both coding and non-coding regions rather than an artificial cDNA sequence.

A. Methods of Testing Efficacy of Human-Albumin-Targeting Reagents In Vivo or Ex Vivo Various methods are provided for assessing delivery or efficacy of human-albumin-targeting reagents in vivo using non-human animals comprising a humanized albumin locus as described elsewhere herein. Such methods can comprise: (a) introducing into the non-human animal a human-albumin-targeting reagent (i.e., administering the human-albumin-targeting reagent to the non-human animal); and (b) assessing the activity of the human-albumin-targeting reagent.

The human-albumin-targeting reagent can be any biological or chemical agent that targets the human albumin locus (the human albumin gene), the human albumin mRNA, or the human albumin protein. Examples of human-albumin-targeting reagents are disclosed elsewhere herein and include, for example, genome-editing agents. For example, the human-albumin-targeting reagent can be an albumin-targeting nucleic acid (e.g., CRISPR/Cas guide RNAs, short hairpin RNAs (shRNAs), or small interfering RNAs (siRNAs)) or nucleic acid encoding an albumin-targeting protein (e.g., a Cas protein such as Cas9, a ZFN, or a TALEN). Alternatively, the human-albumin-targeting reagent can be an albumin-targeting antibody or antigen-binding protein, or any other large molecule or small molecule that targets human albumin. In one example, the human-albumin-targeting reagent is a genome-editing agent such as a nuclease agent and/or an exogenous donor nucleic acid (e.g., a targeting vector). In a particular example, the genome-editing agent can target intron 1, intron 12, or intron 13 of the human albumin gene. For example, the genome-editing agent can target intron 1 of the human albumin gene.

Such human-albumin-targeting reagents can be administered by any delivery method (e.g., AAV, LNP, or HDD) as disclosed in more detail elsewhere herein and by any route of administration. Means of delivering therapeutic complexes and molecules and routes of administration are disclosed in more detail elsewhere herein. In particular methods, the reagents delivered via AAV-mediated delivery. For example, AAV8 can be used to target the liver. In other particular methods, the reagents are delivered by LNP-mediated delivery. In other particular methods, the reagents are delivered by hydrodynamic delivery (HDD). The dose can be any suitable dose. For example, in some methods in which the reagents (e.g., Cas9 mRNA and gRNA) are delivered by LNP-mediated delivery, the dose can be between about 0.01 and about 10 mg/kg, about 0.01 and about 5 mg/kg, between about 0.01 and about 4 mg/kg, between about 0.01 and about 3 mg/kg, between about 0.01 and about 2 mg/kg, between about 0.01 and about 1 mg/kg, between about 0.1 and about 10 mg/kg, between about 0.1 and about 6 mg/kg; between about 0.1 and about 5 mg/kg, between about 0.1 and about 4 mg/kg, between about 0.1 and about 3 mg/kg, between about 0.1 and about 2 mg/kg, between about 0.1 and about 1 mg/kg, between about 0.3 and about 10 mg/kg, between about 0.3 and about 6 mg/kg; between about 0.3 and about 5 mg/kg, between about 0.3 and about 4 mg/kg, between about 0.3 and about 3 mg/kg, between about 0.3 and about 2 mg/kg, between about 0.3 and about 1 mg/kg, about 0.1 mg/kg, about 0.3 mg/kg, about 1 mg/kg, about 2 mg/kg, or about 3 mg/kg. In a specific example, the dose is between about 0.1 and about 6 mg/kg; between about 0.1 and about 3 mg/kg, or between about 0.1 and about 2 mg/kg.

Methods for assessing activity of the human-albumin-targeting reagent are well-known and are provided elsewhere herein. Assessment of activity can be in any cell type, any tissue type, or any organ type as disclosed elsewhere herein. In some methods, assessment of activity is in liver cells. If the albumin-targeting reagent is a genome editing reagent (e.g., a nuclease agent), such methods can comprise assessing modification of the humanized albumin locus. As one example, the assessing can comprise measuring non-homologous end joining (NHEJ) activity at the humanized albumin locus. This can comprise, for example, measuring the frequency of insertions or deletions within the humanized albumin locus. For example, the assessing can comprise sequencing the humanized albumin locus in one or more cells isolated from the non-human animal (e.g., next-generation sequencing). Assessment can comprise isolating a target organ or tissue (e.g., liver) or tissue from the non-human animal and assessing modification of humanized albumin locus in the target organ or tissue. Assessment can also comprise assessing modification of humanized albumin locus in two or more different cell types within the target organ or tissue. Similarly, assessment can comprise isolating a non-target organ or tissue (e.g., two or more non-target organs or tissues) from the non-human animal and assessing modification of humanized albumin locus in the non-target organ or tissue.

Such methods can also comprise measuring expression levels of the mRNA produced by the humanized albumin locus, or by measuring expression levels of the protein encoded by the humanized albumin locus. For example, protein levels can be measured in a particular cell, tissue, or organ type (e.g., liver), or secreted levels can be measured in the serum. Methods for assessing expression of albumin mRNA or protein expressed from the humanized albumin locus are provided elsewhere herein and are well-known. As one example, the BASESCOPE™ RNA in situ hybridization (ISH) assay can be used, for example, to quantify cell-specific edited transcripts.

In some methods, the human-albumin-targeting reagent comprises an exogenous donor nucleic acid (e.g., targeting vector). Such exogenous donor nucleic acids can encode an exogenous protein not encoded or expressed by a wild type endogenous albumin locus (e.g., can comprise an insert nucleic acid that encodes an exogenous protein). In one example, the exogenous protein can be a heterologous protein comprising a human albumin signal peptide fused to a protein not encoded or expressed by a wild type endogenous albumin locus. In one example, the exogenous protein encoded by the exogenous donor nucleic acid once integrated into the humanized albumin locus can be a heterologous protein comprising a human albumin signal peptide fused to a protein not encoded or expressed by a wild type endogenous albumin locus. In some methods, assessment can comprise measuring expression of a messenger RNA encoded by the exogenous donor nucleic acid. Assessment can also comprise measuring expression of the exogenous protein. For example, expression of the exogenous protein can be measured in the liver of the non-human animal, or serum levels of the exogenous protein can be measured.

In some methods, the non-human animals comprising a humanized albumin locus as described elsewhere herein further comprise an inactivated (knocked out) endogenous gene that is not the albumin locus, and optionally the human-albumin-targeting reagent comprises an exogenous donor nucleic acid (e.g., targeting vector) encoding an exogenous protein to replace the function of the inactivated endogenous gene. In a specific example, the inactivated endogenous gene is F9, and the exogenous protein is coagulation factor IX (e.g., human coagulation factor IX).

In some methods, the human-albumin-targeting reagent comprises (1) a nuclease agent designed to target a region of a human albumin gene and (2) an exogenous donor nucleic acid, wherein the exogenous donor nucleic acid is designed to target the human albumin gene. The exogenous donor nucleic acid can, for example, encode an exogenous protein, optionally wherein the protein encoded by a humanized endogenous albumin locus that has been targeted with the exogenous donor nucleic acid is a heterologous protein comprising a human albumin signal peptide fused to the exogenous protein.

As one specific example, if the human-albumin-targeting reagent is a genome editing reagent (e.g., a nuclease agent), percent editing (e.g., total number of insertions or deletions observed over the total number of sequences read in the PCR reaction from a pool of lysed cells) at the humanized albumin locus can be assessed (e.g., in liver cells).

The various methods provided above for assessing activity in vivo can also be used to assess the activity of human-albumin-targeting reagents ex vivo as described elsewhere herein.

In some methods, the human-albumin-targeting reagent is a nuclease agent, such as a CRISPR/Cas nuclease agent, that targets the human albumin gene. Such methods can comprise, for example: (a) introducing into the non-human animal a nuclease agent designed to cleave the human albumin gene (e.g., Cas protein such as Cas9 and a guide RNA designed to target a guide RNA target sequence in the human albumin gene); and (b) assessing modification of the humanized albumin locus.

In the case of a CRISPR/Cas nuclease, for example, modification of the humanized albumin locus will be induced when the guide RNA forms a complex with the Cas protein and directs the Cas protein to the humanized albumin locus, and the Cas/guide RNA complex cleaves the guide RNA target sequence, triggering repair by the cell (e.g., via non-homologous end joining (NHEJ) if no donor sequence is present).

Optionally, two or more guide RNAs can be introduced, each designed to target a different guide RNA target sequence within the human albumin gene. For example, two guide RNAs can be designed to excise a genomic sequence between the two guide RNA target sequences. Modification of the humanized albumin locus will be induced when the first guide RNA forms a complex with the Cas protein and directs the Cas protein to the humanized albumin locus, the second guide RNA forms a complex with the Cas protein and directs the Cas protein to the humanized albumin locus, the first Cas/guide RNA complex cleaves the first guide RNA target sequence, and the second Cas/guide RNA complex cleaves the second guide RNA target sequence, resulting in excision of the intervening sequence.

Additionally or alternatively, an exogenous donor nucleic acid (e.g., targeting vector) capable of recombining with and modifying a human albumin gene is also introduced into the non-human animal. Optionally, the nuclease agent or Cas protein can be tethered to the exogenous donor nucleic acid as described elsewhere herein. Modification of the humanized albumin locus will be induced, for example, when the guide RNA forms a complex with the Cas protein and directs the Cas protein to the humanized albumin locus, the Cas/guide RNA complex cleaves the guide RNA target sequence, and the humanized albumin locus recombines with the exogenous donor nucleic acid to modify the humanized albumin locus. The exogenous donor nucleic acid can recombine with the humanized albumin locus, for example, via homology-directed repair (HDR) or via NHEJ-mediated insertion. Any type of exogenous donor nucleic acid can be used, examples of which are provided elsewhere herein.

In some methods, the human-albumin-targeting reagent comprises an exogenous donor nucleic acid (e.g., targeting vector). Such exogenous donor nucleic acids can encode an exogenous protein not encoded or expressed by a wild type endogenous albumin locus (e.g., can comprise an insert nucleic acid that encodes an exogenous protein). In one example, the exogenous protein can be a heterologous protein comprising a human albumin signal peptide fused to a protein not encoded or expressed by a wild type endogenous albumin locus. For example, the exogenous donor nucleic acid can be a promoterless cassette comprising a splice acceptor, and the exogenous donor nucleic acid can be targeted to the first intron of human albumin.

B. Methods of Optimizing Delivery or Efficacy of Human-Albumin-Targeting Reagent In Vivo or Ex Vivo Various methods are provided for optimizing delivery of human-albumin-targeting reagents to a cell or non-human animal or optimizing the activity or efficacy of human-albumin-targeting reagents in vivo. Such methods can comprise, for example: (a) performing the method of testing the efficacy of a human-albumin-targeting reagent as described above a first time in a first non-human animal or first cell comprising a humanized albumin locus; (b) changing a variable and performing the method a second time in a second non-human animal (i.e., of the same species) or a second cell comprising a humanized albumin locus with the changed variable; and (c) comparing the activity of the human-albumin-targeting reagent in step (a) with the activity of the human-albumin-targeting reagent in step (b), and selecting the method resulting in the higher activity.

Methods of measuring delivery, efficacy, or activity of human-albumin-targeting reagents are disclosed elsewhere herein. For example, such methods can comprise measuring modification of the humanized albumin locus. More effective modification of the humanized albumin locus can mean different things depending on the desired effect within the non-human animal or cell. For example, more effective modification of the humanized albumin locus can mean one or more or all of higher levels of modification, higher precision, higher consistency, or higher specificity. Higher levels of modification (i.e., higher efficacy) of the humanized albumin locus refers to a higher percentage of cells is targeted within a particular target cell type, within a particular target tissue, or within a particular target organ (e.g., liver). Higher precision refers to more precise modification of the humanized albumin locus (e.g., a higher percentage of targeted cells having the same modification or having the desired modification without extra unintended insertions and deletions (e.g., NHEJ indels)). Higher consistency refers to more consistent modification of the humanized albumin locus among different types of targeted cells, tissues, or organs if more than one type of cell, tissue, or organ is being targeted (e.g., modification of a greater number of cell types within the liver). If a particular organ is being targeted, higher consistency can also refer to more consistent modification throughout all locations within the organ (e.g., the liver). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

The variable that is changed can be any parameter. As one example, the changed variable can be the packaging or the delivery method by which the human-albumin-targeting reagent or reagents are introduced into the cell or non-human animal. Examples of delivery methods, such as LNP, HDD, and AAV, are disclosed elsewhere herein. For example, the changed variable can be the AAV serotype. Similarly, the administering can comprise LNP-mediated delivery, and the changed variable can be the LNP formulation. As another example, the changed variable can be the route of administration for introduction of the human-albumin-targeting reagent or reagents into the cell or non-human animal. Examples of routes of administration, such as intravenous, intravitreal, intraparenchymal, and nasal instillation, are disclosed elsewhere herein.

As another example, the changed variable can be the concentration or amount of the human-albumin-targeting reagent or reagents introduced. As another example, the changed variable can be the concentration or the amount of one human-albumin-targeting reagent introduced (e.g., guide RNA, Cas protein, or exogenous donor nucleic acid) relative to the concentration or the amount another human-albumin-targeting reagent introduced (e.g., guide RNA, Cas protein, or exogenous donor nucleic acid).

As another example, the changed variable can be the timing of introducing the human-albumin-targeting reagent or reagents relative to the timing of assessing the activity or efficacy of the reagents. As another example, the changed variable can be the number of times or frequency with which the human-albumin-targeting reagent or reagents are introduced. As another example, the changed variable can be the timing of introduction of one human-albumin-targeting reagent introduced (e.g., guide RNA, Cas protein, or exogenous donor nucleic acid) relative to the timing of introduction of another human-albumin-targeting reagent introduced (e.g., guide RNA, Cas protein, or exogenous donor nucleic acid).

As another example, the changed variable can be the form in which the human-albumin-targeting reagent or reagents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth.

As another example, the changed variable can be the human-albumin-targeting reagent or reagents that are introduced. For example, if the human-albumin-targeting reagent comprises a guide RNA, the changed variable can be introducing a different guide RNA with a different sequence (e.g., targeting a different guide RNA target sequence). Likewise, if the human-albumin-targeting reagent comprises a Cas protein, the changed variable can be introducing a different Cas protein (e.g., introducing a different Cas protein with a different sequence, or a nucleic acid with a different sequence (e.g., codon-optimized) but encoding the same Cas protein amino acid sequence. Likewise, if the human-albumin-targeting reagent comprises an exogenous donor nucleic acid, the changed variable can be introducing a different exogenous donor nucleic acid with a different sequence (e.g., a different insert nucleic acid or different homology arms (e.g., longer or shorter homology arms or homology arms targeting a different region of the human albumin gene)).

In a specific example, the human-albumin-targeting reagent comprises a Cas protein and a guide RNA designed to target a guide RNA target sequence in a human albumin gene. In such methods, the changed variable can be the guide RNA sequence and/or the guide RNA target sequence. In some such methods, the Cas protein and the guide RNA can each be administered in the form of RNA, and the changed variable can be the ratio of Cas mRNA to guide RNA (e.g., in an LNP formulation). In some such methods, the changed variable can be guide RNA modifications (e.g., a guide RNA with a modification is compared to a guide RNA without the modification).

C. Human-Albumin-Targeting Reagents

A human-albumin-targeting reagent can be any reagent that targets a human albumin gene, a human albumin mRNA, or a human albumin protein. For example, it can be a genome-editing reagent such as a nuclease agent that cleaves a target sequence within the human albumin gene and/or an exogenous donor sequence that recombines with a human albumin gene, it can be an antisense oligonucleotide targeting a human albumin mRNA, it can be an antigen-binding protein targeting an epitope of a human albumin protein, or it can be a small molecule targeting human albumin. Human-albumin-targeting reagents in the methods disclosed herein can be known human-albumin-targeting reagents, can be putative-albumin-targeting reagents (e.g., candidate reagents designed to target human albumin), or can be reagents being screened for human-albumin-targeting activity.

(1) Nuclease Agents Targeting Human Albumin Gene

A human-albumin-targeting reagent can be a genome editing reagent such as a nuclease agent that cleaves a target sequence within the human albumin gene. A nuclease target sequence includes a DNA sequence at which a nick or double-strand break is induced by a nuclease agent. The target sequence for a nuclease agent can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell. In a particular example, the nuclease target sequence can be in intron 1, intron 12, or intron 13 of the human albumin gene. For example, the nuclease target sequence can be in intron 1 of the human albumin gene.

The length of the target sequence can vary, and includes, for example, target sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break at a desired target sequence can be used in the methods and compositions disclosed herein. A naturally occurring or native nuclease agent can be employed so long as the nuclease agent induces a nick or double-strand break in a desired target sequence. Alternatively, a modified or engineered nuclease agent can be employed. An "engineered nuclease agent" includes a nuclease that is engineered (modified or derived) from its native form to specifically recognize and induce a nick or double-strand break in the desired target sequence. Thus, an engineered nuclease agent can be derived from a native, naturally occurring nuclease agent or it can be artificially created or synthesized. The engineered nuclease can induce a nick or double-strand break in a target sequence, for example, wherein the target sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are well-known. See, e.g., Frendewey et al. (2010) *Methods in Enzymology* 476:295-307, which is incorporated by reference herein in its entirety for all purposes.

The target sequence of the nuclease agent can be positioned anywhere in or near the albumin locus. The target sequence can be located within a coding region of the albumin gene, or within regulatory regions that influence the expression of the gene. A target sequence of the nuclease agent can be located in an intron, an exon, a promoter, an enhancer, a regulatory region, or any non-protein coding region.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) PNAS 10.1073/pnas.1013133107; Scholze & Boch (2010) *Virulence* 1:428-432; Christian et al. Genetics (2010) 186:757-761; Li et al. (2010) *Nuc. Acids Res.* (2010) doi:10.1093/nar/gkq704; and Miller et al. (2011) *Nature Biotechnology* 29:143-148, each of which is herein incorporated by reference in its entirety.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety. In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) Trends in Biotechnology, 31(7):397-405, each of which is herein incorporated by reference.

Another type of nuclease agent is an engineered meganuclease. Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. Meganucleases are notable for their long target sequences, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples, a naturally occurring variant and/or engineered derivative meganuclease is used. Methods for modifying the kinetics, cofactor interactions, expression, optimal conditions, and/or target sequence specificity, and screening for activity are known. See, e.g., Epinat et al., (2003) *Nucleic Acids Res* 31:2952-62; Chevalier et al., (2002) *Mol Cell* 10:895-905; Gimble et al., (2003) *Mot Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346, each of which is herein incorporated by reference in its entirety.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-Ppol, PI-PspI, F-SceI, F-SceII, F-SuvI, F-TeeI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TeeI, I-TevII, I-TevIII, I-UarAP, I-UarHGPAIP, I-UarHGPA13P, I-VinIP, I-ZbiIP, PI-Mtul, PI-MtuHIP PI-MtuHIIP, PI-Pful, PI-Pfull, PI-Pkol, PI-Pkoll, PI-Rma43812IP, PI-SpBetaIP, PI-SceI, PI-TfuI, PI-TfuII, PI-Thyl, PI-TliI, PI-TliII, or any active variants or fragments thereof.

Meganucleases can recognize, for example, double-stranded DNA sequences of 12 to 40 base pairs. In some cases, the meganuclease recognizes one perfectly matched target sequence in the genome.

Some meganucleases are homing nucleases. One type of homing nuclease is a LAGLIDADG family of homing nucleases including, for example, I-SceI, I-CreI, and I-Dmol.

Nuclease agents can further comprise CRISPR/Cas systems as described in more detail below.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target sequence and hence retain nick or double-strand-break-inducing activity. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

The nuclease agent may be introduced into a cell or non-human animal by any known means. A polypeptide encoding the nuclease agent may be directly introduced into the cell or non-human animal. Alternatively, a polynucleotide encoding the nuclease agent can be introduced into the cell or non-human animal. When a polynucleotide encoding the nuclease agent is introduced, the nuclease agent can be transiently, conditionally, or constitutively expressed within the cell. The polynucleotide encoding the nuclease agent can be contained in an expression cassette and be operably linked to a conditional promoter, an inducible promoter, a constitutive promoter, or a tissue-specific promoter. Examples of promoters are discussed in further detail elsewhere herein. Alternatively, the nuclease agent can be introduced into the cell as an mRNA encoding the nuclease agent.

A polynucleotide encoding a nuclease agent can be stably integrated in the genome of a cell and operably linked to a promoter active in the cell. Alternatively, a polynucleotide encoding a nuclease agent can be in a targeting vector.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given eukaryotic cell of interest, including a human cell, a non-human cell, a mammalian cell, a rodent cell, a mouse cell, a rat cell or any other host cell of interest, as compared to the naturally occurring polynucleotide sequence.

(2) CRISPR/Cas Systems Targeting Human Albumin Gene

A particular type of human-albumin-targeting reagent can be a Clustered Regularly Interspersed Short Palindromic Repeats (CRISPR)/CRISPR-associated (Cas) system that targets the human albumin gene. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins and Polynucleotides Encoding Cas Proteins.

Cas proteins generally comprise at least one RNA recognition or binding domain that can interact with guide RNAs (gRNAs). Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales* bacterium, *Polaromonas naphthalenivorans, Polaromonas* sp., *Crocosphaera watsonii,* Cyanothece sp., *Microcystis aeruginosa, Synechococcus* sp *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni.*

Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number QOP897) is another exemplary Cas9 protein. See, e.g., Kim et al. (2017) Nat. Comm. 8:14500, herein incorporated by reference in its entirety for all purposes. SaCas9 is smaller than SpCas9, and CjCas9 is smaller than both SaCas9 and SpCas9. An exemplary Cas9 protein sequence can comprise, consist essentially of, or consist of SEQ ID NO: 38. An exemplary DNA encoding the Cas9 protein can comprise, consist essentially of, or consist of SEQ ID NO: 39.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) Cell 163(3): 759-771, herein incorporated by reference in its entirety for all purposes. Exemplary Cpf1 proteins are from *Francisella tularensis* 1, *Francisella tularensis* subsp. *novicida, Prevotella albensis,* Lachnospiraceae bacterium MC2017 1, *Butyrivibrio proteoclasticus,* Peregrinibacteria bacterium GW2011 GWA2_33_10, Parcubacteria bacterium GW2011_GWC2_44_17, Smithella sp. SCADC, Acidaminococcus sp. BV3L6, Lachnospiraceae bacterium MA2020, *Candidatus Methanoplasma termitum, Eubacterium eligens, Moraxella bovoculi* 237, *Leptospira inadai,* Lachnospiraceae bacterium ND2006, *Porphyromonas* crevioricanis 3, *Prevotella disiens,* and *Porphyromonas macacae.* Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) Nature 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) Science 351(6268):84-88, herein incorporated by reference in its entirety for all purposes. Other SpCas9 variants include K855A and K810A/K1003A/R1060A.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) Science 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), Lachnospiraceae bacterium ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins (e.g., nuclease-active Cas proteins or nuclease-inactive Cas proteins) can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) J Biol. Chem. 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas proteins can also be tethered to exogenous donor nucleic acids or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) Mini Rev. Med. Chem. 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor nucleic acid or labeled nucleic acid can be tethered to the C-terminus, the N-terminus, or to an internal region within the Cas protein. In one example, the exogenous donor nucleic acid or labeled nucleic acid is tethered to the C-terminus or the N-terminus of the Cas protein. Likewise, the Cas protein can be tethered to the 5' end, the 3' end, or to an internal region within the exogenous donor nucleic acid or labeled nucleic acid. That is, the exogenous donor nucleic acid or labeled nucleic acid can be tethered in any orientation and polarity. For example, the Cas protein can be tethered to the 5' end or the 3' end of the exogenous donor nucleic acid or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs.

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 40). Any of the DNA-targeting segments disclosed herein can be joined to the 5' end of SEQ ID NO: 40 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of

```
                                    (SEQ ID NO: 41)
AGCAUAGCAAGUUAAAAUAAGGCUAGUCCGUUAUCAACUUGAAAAAGUGG

CACCGAGUCGGUGCUUU.
```

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from S. pyogenes, a typical DNA-targeting segment is between 16 and 20 nucleotides in length or between 17 and 20 nucleotides in length. For Cas9 from S. aureus, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from S. pyogenes include 171-nucleotide, 89-nucleotide, 75-nucleotide, and 65-nucleotide versions. See, e.g., Deltcheva et al. (2011) Nature 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment joined to a scaffold sequence (i.e., the protein-binding or Cas-binding sequence of the guide RNA). For example, such guide RNAs can have a 5' DNA-targeting segment and a 3' scaffold sequence. Exemplary scaffold sequences comprise, consist essentially of, or consist of:

```
                              (version 1; SEQ ID NO: 42)
GUUUUAGAGCUAGAAAUAGCAAGUUAAAAUAAGGCUAGUCCGUUAUCAAC

UUGAAAAAGUGGCACCGAGUCGGUGCU;

(version 2; SEQ ID NO: 43)
GUUGGAACCAUUCAAAACAGCAUAGCAAGUUAAAAUAAGGCUAGUCCGUU

AUCAACUUGAAAAAGUGGCACCGAGUCGGUGC;

(version 3; SEQ ID NO: 44)
GUUUUAGAGCUAGAAAUAGCAAGUUAAAAUAAGGCUAGUCCGUUAUCAAC

UUGAAAAAGUGGCACCGAGUCGGUGC;
``` and

```
                              (version 4; SEQ ID NO: 45)
GUUUAAGAGCUAUGCUGGAAACAGCAUAGCAAGUUUAAAUAAGGCUAGUC

CGUUAUCAACUUGAAAAAGUGGCACCGAGUCGGUGC.
```

Guide RNAs targeting any guide RNA target sequence can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of SEQ ID NOS: 42-45 to form a single guide RNA (chimeric guide RNA). Guide RNA versions 1, 2, 3, and 4 as disclosed elsewhere herein refer to DNA-targeting segments (i.e., guide sequences or guides) joined with scaffold versions 1, 2, 3, and 4, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Reports* 22:1-9, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) Nat. Biotech. 35(12): 1179-1187, herein incorporated by reference in its entirety for all purposes. Other examples of modified guide RNAs are provided, e.g., in WO 2018/107028 A1, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., $-20°$ C., $4°$ C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

Guide RNA Target Sequences.

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both. In a particular example, the guide RNA target sequence can be in intron 1, intron 12, or intron 13 of the human albumin gene. For example, the guide RNA target sequence can be in intron 1 of the human albumin gene.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-N$_1$GG-3', where N$_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CCN2-3', where N2 is any DNA nucleotide and is immediately 5' of the sequence to which the DNA-targeting segment of the guide RNA hybridizes on the complementary strand of the target DNA. In some such cases, N$_1$ and N$_2$ can be complementary and the N$_1$-N$_2$ base pair can be any base pair (e.g., N$_1$=C and N$_2$=G; N$_1$=G and N$_2$=C; N$_1$=A and N$_2$=T; or N$_1$=T, and N$_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are GN$_{19}$NGG (SEQ ID NO: 46) or N$_{20}$NGG (SEQ ID NO: 47). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., GGN$_{20}$NGG; SEQ ID NO: 48) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 46-48, including the 5' G or GG and the 3' GG or NGG. Yet other guide RNA target sequences PAMs can have between 14 and 20 nucleotides in length of SEQ ID NOS: 46-48.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

(3) Exogenous Donor Nucleic Acids Targeting Human Albumin Gene

The methods and compositions disclosed herein can utilize exogenous donor nucleic acids to modify the humanized albumin locus following cleavage of the humanized albumin locus with a nuclease agent or independent of cleavage of the humanized albumin locus with a nuclease agent. In such methods using a nuclease agent, the nuclease agent protein cleaves the humanized albumin locus to create a single-strand break (nick) or double-strand break, and the exogenous donor nucleic acid recombines the humanized albumin locus via non-homologous end joining (NHEJ)-mediated ligation or through a homology-directed repair event. Optionally, repair with the exogenous donor nucleic acid removes or disrupts the nuclease target sequence so that alleles that have been targeted cannot be re-targeted by the nuclease agent.

The exogenous donor nucleic acid can target any sequence in the human albumin gene. Some exogenous donor nucleic acids comprise homology arms. Other exogenous donor nucleic acids do not comprise homology arms. The exogenous donor nucleic acids can be capable of insertion into a humanized albumin locus by homology-directed repair, and/or they can be capable of insertion into a humanized albumin locus by non-homologous end joining. In one example, the exogenous donor nucleic acid (e.g., a targeting vector) can target intron 1, intron 12, or intron 13 of the human albumin gene. For example, the exogenous donor nucleic acid can target intron 1 of the human albumin gene.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) *Nat. Commun.* 7:10431, herein incorporated by reference in its entirety for all purposes. Exogenous donor nucleic acids can be naked nucleic acids or can be delivered by viruses, such as AAV. In a specific example, the exogenous donor nucleic acid can be delivered via AAV and can be capable of insertion into a humanized albumin locus by non-homologous end joining (e.g., the exogenous donor nucleic acid can be one that does not comprise homology arms).

An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE® 700).

Exogenous donor nucleic acids can also comprise nucleic acid inserts including segments of DNA to be integrated at the humanized albumin locus. Integration of a nucleic acid insert at a humanized albumin locus can result in addition of a nucleic acid sequence of interest to the humanized albumin locus, deletion of a nucleic acid sequence of interest at the humanized albumin locus, or replacement of a nucleic acid sequence of interest at the humanized albumin locus (i.e., deletion and insertion). Some exogenous donor nucleic acids are designed for insertion of a nucleic acid insert at the humanized albumin locus without any corresponding deletion at the humanized albumin locus. Other exogenous donor nucleic acids are designed to delete a nucleic acid sequence of interest at the humanized albumin locus without any corresponding insertion of a nucleic acid insert. Yet other exogenous donor nucleic acids are designed to delete a nucleic acid sequence of interest at the humanized albumin locus and replace it with a nucleic acid insert.

The nucleic acid insert or the corresponding nucleic acid at the humanized albumin locus being deleted and/or replaced can be various lengths. An exemplary nucleic acid insert or corresponding nucleic acid at the humanized albumin locus being deleted and/or replaced is between about 1 nucleotide to about 5 kb in length or is between about 1 nucleotide to about 1,000 nucleotides in length. For example, a nucleic acid insert or a corresponding nucleic acid at the humanized albumin locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the humanized albumin locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the humanized albumin locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the humanized albumin locus. Optionally, such point mutations can result in a conservative amino acid substitution (e.g., substitution of aspartic acid [Asp, D] with glutamic acid [Glu, E]) in the encoded polypeptide.

Some exogenous donor nucleic acids can encode an exogenous protein not encoded or expressed by a wild type endogenous albumin locus (e.g., can comprise an insert nucleic acid that encodes an exogenous protein). In one example, a humanized albumin locus targeted by the exogenous donor nucleic acid can encode a heterologous protein comprising a human albumin signal peptide fused to a protein not encoded or expressed by a wild type endogenous albumin locus. For example, the exogenous donor nucleic acid can be a promoterless cassette comprising a splice acceptor, and the exogenous donor nucleic acid can be targeted to the first intron of human albumin.

Donor Nucleic Acids for Non-Homologous-End-Joining-Mediated Insertion.

Some exogenous donor nucleic acids are capable of insertion into a humanized albumin locus by non-homologous end joining. In some cases, such exogenous donor nucleic acids do not comprise homology arms. For example, such exogenous donor nucleic acids can be inserted into a blunt end double-strand break following cleavage with a nuclease agent. In a specific example, the exogenous donor nucleic acid can be delivered via AAV and can be capable of insertion into a humanized albumin locus by non-homologous end joining (e.g., the exogenous donor nucleic acid can be one that does not comprise homology arms). In a specific example, the exogenous donor nucleic acid can be inserted via homology-independent targeted integration. For example, the insert sequence in the exogenous donor nucleic acid to be inserted into a humanized albumin locus can be flanked on each side by a target site for a nuclease agent (e.g., the same target site as in the humanized albumin locus, and the same nuclease agent being used to cleave the target site in the humanized albumin locus). The nuclease agent can then cleave the target sites flanking the insert sequence. In a specific example, the exogenous donor nucleic acid is delivered AAV-mediated delivery, and cleavage of the target sites flanking the insert sequence can remove the inverted terminal repeats (ITRs) of the AAV. In some methods, the target site in the humanized albumin locus (e.g., a gRNA target sequence including the flanking protospacer adjacent motif) is no longer present if the insert sequence is inserted into the humanized albumin locus in the correct orientation but it is reformed if the insert sequence is inserted into the humanized albumin locus in the opposite orientation. This can help ensure that the insert sequence is inserted in the correct orientation for expression.

Other exogenous donor nucleic acids have short single-stranded regions at the 5' end and/or the 3' end that are complementary to one or more overhangs created by nuclease-mediated cleavage at the humanized albumin locus. These overhangs can also be referred to as 5' and 3' homology arms. For example, some exogenous donor nucleic acids have short single-stranded regions at the 5' end and/or the 3' end that are complementary to one or more overhangs created by nuclease-mediated cleavage at 5' and/or 3' target sequences at the humanized albumin locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the humanized albumin locus or only at the 3' end complementary to an overhang created at a 3' target sequence at the humanized albumin locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by nuclease-mediated cleavage at the humanized albumin locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Preferably, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) Cell 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

Donor Nucleic Acids for Insertion by Homology-Directed Repair.

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the humanized albumin locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a nuclease agent is used in combination with an exogenous donor nucleic acid, the 5' and 3' target sequences are preferably located in sufficient proximity to the nuclease cleavage site (e.g., within sufficient proximity to a the nuclease target sequence) so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the targeted locus that correspond to the 5' and 3' homology arms of the exogenous donor nucleic acid are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor nucleic acid can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor nucleic acid and the nuclease cleavage site can vary. For example, target sequences can be located 5' to the nuclease cleavage site, target sequences can be located 3' to the nuclease cleavage site, or the target sequences can flank the nuclease cleavage site.

(4) Other Human-Albumin-Targeting Reagents

The activity of any other known or putative human-albumin-targeting reagent can also be assessed using the non-human animals disclosed herein. Similarly, any other molecule can be screened for human-albumin-targeting activity using the non-human animals disclosed herein.

Examples of other human-albumin-targeting reagents include antisense oligonucleotides (e.g., siRNAs or shRNAs) that act through RNA interference (RNAi). Antisense oligonucleotides (ASOs) or antisense RNAs are short synthetic strings of nucleotides designed to prevent the expression of a targeted protein by selectively binding to the RNA that encodes the targeted protein and thereby preventing translation. These compounds bind to RNA with high affinity and selectivity through well characterized Watson-Crick base pairing (hybridization). RNA interference (RNAi) is an endogenous cellular mechanism for controlling gene expression in which small interfering RNAs (siRNAs) that are bound to the RNA-induced silencing complex (RISC) mediate the cleavage of target messenger RNA (mRNA).

Other human-albumin-targeting reagents include antibodies or antigen-binding proteins designed to specifically bind a human albumin epitope. Other human-albumin-targeting reagents include small-molecule reagents.

D. Administering Human-Albumin-Targeting Reagents to Non-Human Animals or Cells

The methods disclosed herein can comprise introducing into a non-human animal or cell various molecules (e.g., human-albumin-targeting reagents such as therapeutic molecules or complexes), including, for example, nucleic acids, proteins, nucleic-acid-protein complexes, or protein complexes. "Introducing" includes presenting to the cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs) introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a molecule (e.g., a nucleic acid or protein) into a cell or non-human animal. Methods for introducing molecules into various cell types are known and include, for example, stable transfection methods, transient transfection methods, and virus-mediated methods.

Transfection protocols as well as protocols for introducing molecules into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of molecules (e.g., nucleic acids or proteins) into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing molecules (e.g., nucleic acid or proteins) into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4):694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediate AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as 5010, 5024, 5027, 5031, or 5033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) Cell Reports 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) Cell Reports 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), di stearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-di stearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. The Cas9 mRNA can be in a 1:2 ratio by weight to the guide RNA.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by MEW molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-Albumin-Targeting Reagents In Vivo or Ex Vivo The methods disclosed herein can further comprise detecting or measuring activity of human-albumin-targeting reagents. For example, if the human-albumin-targeting reagent is a genome editing reagent (e.g., CRISPR/Cas designed to target the human albumin locus), the measuring can comprise assessing the humanized albumin locus for modifications.

Various methods can be used to identify cells having a targeted genetic modification. The screening can comprise a quantitative assay for assessing modification-of-allele (MOA) of a parental chromosome. See, e.g., US 2004/0018626; US 2014/0178879; US 2016/0145646; WO 2016/081923; and Frendewey et al. (2010)*Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the humanized albumin locus in a non-human animal can be in any cell type from any tissue or organ. For example, the assessment can be in multiple cell types from the same tissue or organ or in cells from multiple locations within the tissue or organ. This can provide information about which cell types within a target tissue or organ are being targeted or which sections of a tissue or organ are being reached by the human-albumin-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

If the reagent is designed to inactivate the humanized albumin locus, affect expression of the humanized albumin locus, prevent translation of the humanized albumin mRNA, or clear the humanized albumin protein, the measuring can comprise assessing humanized albumin mRNA or protein expression. This measuring can be within the liver or particular cell types or regions within the liver, or it can involve measuring serum levels of secreted humanized albumin protein.

If the reagent is an exogenous donor nucleic acid encoding an exogenous protein not encoded or expressed by a wild type endogenous albumin locus, the measuring can comprise assessing expression of the mRNA encoded by the exogenous donor nucleic acid or assessing expression of the exogenous protein. This measuring can be within the liver or particular cell types or regions within the liver, or it can involve measuring serum levels of secreted exogenous protein. In a specific example, the exogenous protein is a factor IX protein. Optionally, the assessing comprises measuring serum levels of the factor IX protein in the non-human animal and/or comprises assessing activated partial thromboplastin time or performing a thrombin generation assay. Optionally, the non-human animal further comprises an inactivated F9 locus, and the assessing comprises measuring serum levels of the factor IX protein in the non-human animal and/or comprises assessing activated partial thromboplastin time (aPTT) or performing a thrombin generation assay (TGA). These assays are described in more detail in the examples.

One example of an assay that can be used is the BASESCOPE™ RNA in situ hybridization (ISH) assay, which a method that can quantify cell-specific edited transcripts, including single nucleotide changes, in the context of intact fixed tissue. The BASESCOPE™ RNA ISH assay can complement NGS and qPCR in characterization of gene editing. Whereas NGS/qPCR can provide quantitative average values of wild type and edited sequences, they provide no information on heterogeneity or percentage of edited cells within a tissue. The BASESCOPE™ ISH assay can provide a landscape view of an entire tissue and quantification of wild type versus edited transcripts with single-cell resolution, where the actual number of cells within the target tissue containing the edited mRNA transcript can be quantified. The BASESCOPE™ assay achieves single-molecule RNA detection using paired oligo ("ZZ") probes to amplify signal without non-specific background. However, the BASESCOPE™ probe design and signal amplification system enables single-molecule RNA detection with a ZZ probe, and it can differentially detect single nucleotide edits and mutations in intact fixed tissue.

Production and secretion of the humanized albumin protein or exogenous protein can be assessed by any known means. For example, expression can be assessed by measuring levels of the encoded mRNA in the liver of the non-human animal or levels of the encoded protein in the liver of the non-human animal using known assays. Secretion of the humanized albumin protein or exogenous protein can be assessed by measuring or plasma levels or serum levels of the encoded humanized albumin protein or exogenous protein in the non-human animal using known assays.

IV. Methods of Making Non-Human Animals Comprising a Humanized Albumin Locus

Various methods are provided for making a non-human animal genome, non-human animal cell, or non-human animal comprising a humanized albumin (ALB) locus as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted albumin locus.

For example, the method of producing a non-human animal comprising a humanized albumin locus can comprise: (1) modifying the genome of a pluripotent cell to comprise the humanized albumin locus; (2) identifying or selecting the genetically modified pluripotent cell comprising the humanized albumin locus; (3) introducing the genetically modified pluripotent cell into a non-human animal host embryo; and (4) implanting and gestating the host embryo in a surrogate mother. For example, the method of producing a non-human animal comprising a humanized albumin locus can comprise: (1) modifying the genome of a pluripotent cell to comprise the humanized albumin locus; (2) identifying or selecting the genetically modified pluripotent cell comprising the humanized albumin locus; (3) introducing the genetically modified pluripotent cell into a non-human animal host embryo; and (4) gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized albumin locus.

The methods can further comprise identifying a cell or animal having a modified target genomic locus. Various methods can be used to identify cells and animals having a targeted genetic modification.

The step of modifying the genome can, for example, utilize exogenous donor nucleic acids (e.g., targeting vectors) to modify an albumin locus to comprise a humanized albumin locus disclosed herein. As one example, the targeting vector can be for generating a humanized albumin gene at an endogenous albumin locus (e.g., endogenous non-human animal albumin locus), wherein the targeting vector comprises a 5' homology arm targeting a 5' target sequence at the endogenous albumin locus and a 3' homology arm targeting a 3' target sequence at the endogenous albumin locus. Exogenous donor nucleic acids can also comprise nucleic acid inserts including segments of DNA to be integrated in the albumin locus. Integration of a nucleic acid insert in the albumin locus can result in addition of a nucleic acid sequence of interest in the albumin locus, deletion of a nucleic acid sequence of interest in the albumin locus, or replacement of a nucleic acid sequence of interest in the albumin locus (i.e., deletion and insertion). The homology arms can flank an insert nucleic acid comprising human albumin sequence to generate the humanized albumin locus (e.g., for deleting a segment of the endogenous albumin locus and replacing with an orthologous human albumin sequence).

The exogenous donor nucleic acids can be for non-homologous-end-joining-mediated insertion or homologous recombination. Exogenous donor nucleic acids can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN).

Exogenous donor nucleic acids can also comprise a heterologous sequence that is not present at an untargeted endogenous albumin locus. For example, an exogenous donor nucleic acids can comprise a selection cassette, such as a selection cassette flanked by recombinase recognition sites.

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the albumin locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. In some targeting vectors, the intended mutation in the endogenous albumin locus is included in an insert nucleic acid flanked by the homology arms.

In cells other than one-cell stage embryos, the exogenous donor nucleic acid can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites, wherein the insert nucleic acid comprises a human albumin sequence to generate a humanized albumin locus; and (b) identifying at least one cell comprising in its genome the insert nucleic acid integrated at the endogenous albumin locus (i.e., identifying at least one cell comprising the humanized albumin locus). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized albumin locus; and (b) identifying at least one cell comprising in its genome the insert nucleic acid integrated at the target genomic locus.

Alternatively, the modified pluripotent cell can be generated by (a) introducing into the cell: (i) a nuclease agent, wherein the nuclease agent induces a nick or double-strand break at a target site within the endogenous albumin locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises a human albumin sequence to generate a humanized albumin locus; and (c) identifying at least one cell comprising in its genome the insert nucleic acid integrated at the endogenous albumin locus (i.e., identifying at least one cell comprising the humanized albumin locus). Alternatively, the modified pluripotent cell can be generated by (a) introducing into the cell: (i) a nuclease agent or a nucleic acid encoding the nuclease agent, wherein the nuclease agent induces a nick or double-strand break at a target site within the endogenous albumin locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises a human albumin sequence to generate a humanized albumin locus; and (c) identifying at least one cell comprising in its genome the insert nucleic acid integrated at the endogenous albumin locus (i.e., identifying at least one cell comprising the humanized albumin locus). Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized albumin locus; and (c) identifying at least one cell comprising a modification (e.g., integration of the insert nucleic acid) at the target genomic locus. Any nuclease agent that induces a nick or double-strand break into a desired recognition site can be used. Alternatively, the modified pluripotent cell can be generated by (a) introducing into the cell: (i)

a nuclease agent or a nucleic acid encoding the nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized albumin locus; and (c) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized albumin locus using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the humanized albumin locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized albumin locus. It is recognized that depending on the method used to generate the F0 animal, the number of cells within the F0 animal that have the humanized albumin locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized albumin locus or can be homozygous for the humanized albumin locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Mouse Albumin Protein (P07724.3; NP_033784.2) |
| 2 | Protein | Mouse Albumin Protein - Signal Peptide |
| 3 | Protein | Mouse Albumin Protein - Propeptide |
| 4 | Protein | Mouse Albumin Protein - Serum Albumin |
| 5 | Protein | Human Albumin Protein (P02768.2; NP_000468.1) |
| 6 | Protein | Human Albumin Protein - Signal Peptide |
| 7 | Protein | Human Albumin Protein - Propeptide |
| 8 | Protein | Human Albumin Protein - Serum Albumin |
| 9 | DNA | Mouse Alb CDS |
| 10 | DNA | Mouse Alb CDS - Signal Peptide |
| 11 | DNA | Mouse Alb CDS - Propeptide |
| 12 | DNA | Mouse Alb CDS - Serum Albumin |
| 13 | DNA | Human ALB CDS |
| 14 | DNA | Human ALB CDS - Signal Peptide |
| 15 | DNA | Human ALB CDS - Propeptide |
| 16 | DNA | Human ALB CDS - Serum Albumin |
| 17 | DNA | MAID 7626 Allele (ALB Humanized Region with Neo Self-Deleting Cassette) |
| 18 | DNA | MAID 7627 Allele (ALB Humanized Region, Cassette-Deleted) |
| 19 | DNA | A - 5' Mouse/5' Human Junction |
| 20 | DNA | B - Human/XhoI/LoxP Cassette Junction |
| 21 | DNA | C - Cassette loxP/I-CeuI/NheI/Mouse Junction |
| 22 | DNA | D - Human/XhoI/LoxP/I-CeuI/NheI/Mouse Junction |
| 23 | DNA | 7626hTU - Fwd |
| 24 | DNA | 7626hTU - Probe |
| 25 | DNA | 7626hTU - Rev |
| 26 | DNA | 7626hTD - Fwd |
| 27 | DNA | 7626hTD - Probe |
| 28 | DNA | 7626hTD - Rev |
| 29 | DNA | 7626mTU - Fwd |
| 30 | DNA | 7626mTU - Probe |
| 31 | DNA | 7626mTU - Rev |
| 32 | DNA | 7626mTD - Fwd |
| 33 | DNA | 7626mTD - Probe |
| 34 | DNA | 7626mTD - Rev |
| 35 | DNA | Human Albumin Sequence in MAID 7626 and MAID 7627 Alleles |
| 36 | DNA | Mouse Albumin mRNA (NM_009654.4) |
| 37 | DNA | Human Albumin mRNA (NM_000477.7) |
| 38 | Protein | Cas9 |
| 39 | DNA | Cas9 |
| 40 | RNA | crRNA Tail |
| 41 | RNA | TracrRNA |
| 42 | RNA | Guide RNA Scaffold v1 |
| 43 | RNA | Guide RNA Scaffold v2 |
| 44 | RNA | Guide RNA Scaffold v3 |
| 45 | RNA | Guide RNA Scaffold v4 |
| 46 | DNA | Guide RNA Target Sequence Plus PAM v1 |
| 47 | DNA | Guide RNA Target Sequence Plus PAM v1 |
| 48 | DNA | Guide RNA Target Sequence Plus PAM v1 |
| 49 | RNA | G009844 Guide Sequence |
| 50 | RNA | G009852 Guide Sequence |
| 51 | RNA | G009857 Guide Sequence |
| 52 | RNA | G009859 Guide Sequence |
| 53 | RNA | G009860 Guide Sequence |
| 54 | RNA | G009874 Guide Sequence |
| 55 | RNA | G012752 Guide Sequence |
| 56 | RNA | G012753 Guide Sequence |
| 57 | RNA | G012761 Guide Sequence |
| 58 | RNA | G012764 Guide Sequence |
| 59 | RNA | G012765 Guide Sequence |
| 60 | RNA | G012766 Guide Sequence |
| 61 | RNA | G009864 Guide Sequence |
| 62 | RNA | G000666 Guide Sequence |
| 63 | DNA | Bidirectional hF9 Insertion Template |
| 64 | DNA | CAGG-hF9 Construct |

EXAMPLES

Example 1. Generation of Mice Comprising a Humanized Albumin (ALB) Locus

A large targeting vector (LTVEC) comprising a 5' homology arm comprising 20 kb of the mouse albumin (Alb) locus (from bMQ-127G8) and 3' homology arm comprising 127 kb of the mouse albumin (Alb) locus (from bMQ-127G8) was generated to replace a region of 14.4 kb (14,376 bp) from the mouse albumin (Alb) gene with 17.3 kb (17,335 bp) of the corresponding human sequence of albumin (ALB) (from RP11-31P12). Information on mouse and human albumin is provided in Table 3. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

human 3' UTR, with a buffer of 100 bp of 3' human sequence after the 3' UTR just before the remaining loxP site. This is the MAID 7627 allele. See FIG. 1B.

Sequences for the mouse albumin signal peptide, propeptide, and serum albumin are set forth in SEQ ID NOS: 2-4, respectively, with the corresponding coding sequences set forth in SEQ ID NOS: 10-12, respectively. Sequences for the human albumin signal peptide, propeptide, and serum albumin are set forth in SEQ ID NOS: 6-8, respectively, with the corresponding coding sequences set forth in SEQ ID NOS: 14-16, respectively. The expected encoded humanized albumin protein is identical to the human albumin protein. See FIGS. 1A and 1B. An alignment of the mouse and human albumin proteins along with the humanized albumin protein is provided in FIGS. 3A-3B. The mouse and human Alb/ALB coding sequences are set forth in SEQ ID NOS: 9 and 13, respectively. The mouse and human albumin protein sequences are set forth in SEQ ID NOS: 1 and 5, respectively. The sequences for the expected humanized ALB coding sequence and the expected humanized albumin protein are set forth in SEQ ID NOS: 13 and 5, respectively.

To generate the mutant allele, the large targeting vector described above was introduced into F1H4 mouse embryonic stem cells. F1H4 mouse ES cells were derived from

TABLE 3

Mouse and Human Albumin (ALB).

| | Official Symbol | NCBI Gene ID | Primary Source | RefSeq mRNA ID | UniProt ID | Genomic Assembly | Location |
|---|---|---|---|---|---|---|---|
| Mouse | Alb | 11657 | MGI:87991 | NM_009654 | P07724 | GRCm38.p4 | Chr 5: 90,460,870 . . . 90,476,602 (+) |
| Human | ALB | 213 | HGNC:399 | NM_000477 | P02768 | GRCh38.p12 | Chr 4: 73404239 . . . 73421484 (+) |

Specifically, a region from the ATG start codon through the stop codon (i.e., coding exons 1-14) was deleted from the mouse albumin (Alb) locus. A corresponding region of the human albumin (ALB) from the ATG start codon to 100 bp downstream of the stop codon was inserted in place of the deleted mouse region. AloxP-mPrml-Crei-pA-hUbl-em7-Neo-pA-loxP cassette (4,766 bp) was inserted downstream of the human 3' UTR, with a buffer of −100 bp of 3' human sequence after the 3' UTR just before the cassette. This is the MAID 7626 allele. See FIG. 1A. After cassette deletion, loxP and cloning sites (38 bp) remained downstream of the hybrid embryos produced by crossing a female C57BL/6NTac mouse to a male 12956/SvEvTac mouse. See, e.g., US 2015-0376651 and WO 2015/200805, each of which is herein incorporated by reference in its entirety for all purposes. Following antibiotic selection, colonies were picked, expanded, and screened by<sup>TAQMAN</sup>®. See FIG. 2. Loss-of-allele assays were performed to detect loss of the endogenous mouse allele, and gain-of-allele assays were performed to detect gain of the humanized allele using the primers and probes set forth in Table 4.

TABLE 4

Screening Assays.

| Assay | Description | Primer/Probe | | Sequence |
|---|---|---|---|---|
| 7626hTU | Upstream Human Insertion | Fwd Probe Rev | (MGB) | GTAACCTTTATTTCCCTTCTTTTTCTCTT (SEQ ID NO: 23) AGCTCGGCTTATTC (SEQ ID NO: 24) CGTGCATCTCGACGAAACAC (SEQ ID NO: 25) |
| 7626hTD | Downstream Human Insertion | Fwd Probe Rev | (MGB) | GCAGAACCAAAGTAAGACTAAGCAAA (SEQ ID NO: 26) AGAACAAATTACCTGATTTC (SEQ ID NO: 27) TGTTTCGGTGACTATGGCCTTAT (SEQ ID NO: 28) |
| 7626mTU | Upstream Mouse LOA | Fwd Probe Rev | (MGB) | GCCGAGAAGCACGTAAGAGTTT (SEQ ID NO: 29) ATGTTTTTTCATCTCTGCTTGT (SEQ ID NO: 30) AATACCAGGCTTCCATTACTAGAAAAA (SEQ ID NO: 31) |

TABLE 4-continued

Screening Assays.

| Assay | Description | Primer/Probe | Sequence |
|---|---|---|---|
| 7626mTD | Downstream Mouse LOA | Fwd | CCCTCCCATGGCCTAACAAC (SEQ ID NO: 32) |
| | | Probe (BHQ) | TTGGGCACAACAGATGTCAGAGAGC (SEQ ID NO: 33) |
| | | Rev | ACGTGCCTTGCATTGCTTA (SEQ ID NO: 34) |

Modification-of-allele (MOA) assays including loss-of-allele (*LOA*) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the *LOA* assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

F0 mice were generated from the modified ES cells using the VELOCIMOUSE® method. Specifically, mouse ES cell clones comprising the humanized albumin locus described above that were selected by the MOA assay described above were injected into 8-cell stage embryos using the VELOCIMOUSE® method. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE® method, targeted mouse embryonic stem (ES) cells are injected through laser-assisted injection into pre-morula stage embryos, e.g., eight-cell-stage embryos, which efficiently yields F0 generation mice that are fully ES-cell-derived. In the VELOCIMOUSE® method, the injected pre-morula stage embryos were cultured to the blastocyst stage, and the blastocyst-stage embryos are introduced into and gestated in surrogate mothers to produce the F0 generation mice. When starting with mouse ES cell clones homozygous for the targeted modification, F0 mice homozygous for the targeted modification are produced. When starting with mouse ES cell clones heterozygous for the targeted modification, subsequent breeding can be performed to produce mice homozygous for the targeted modification.

Example 2. Validation of Mice Comprising a Humanized Albumin (ALB) Locus

Figure 4:
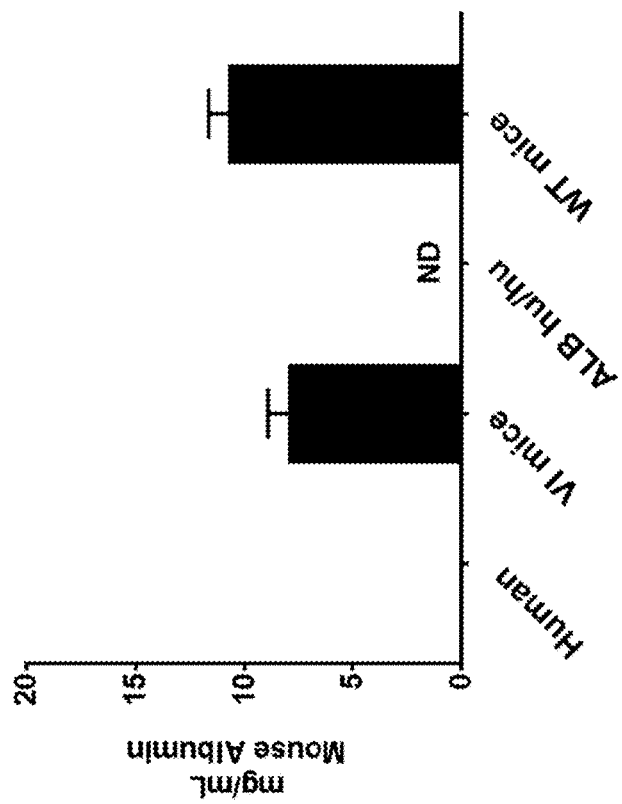
FIG. 4 shows human albumin levels in plasma samples from humanized albumin mice (ALB$^{hu/hu}$) and wild type (WT) mice. Pooled normal human plasma (George King-Biomedical Inc.) was used as a positive control. VelocImmune (VI) mice were used as a negative control.
Figure 5:
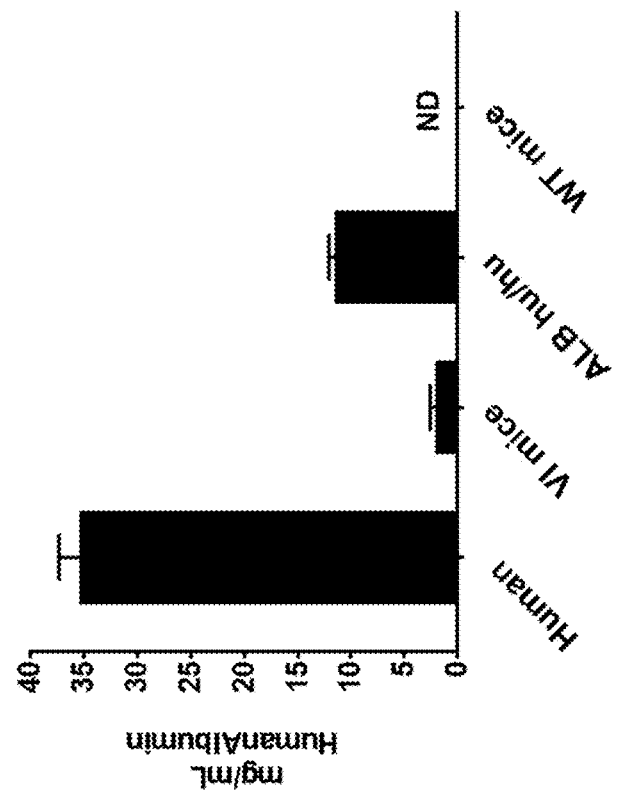
FIG. 5 shows mouse albumin levels in plasma samples from humanized albumin mice (ALB$^{hu/hu}$) and wild type (WT) mice. Pooled normal human plasma (George King-Biomedical Inc.) was used as a negative control. VI mice were used as a positive control.

To validate the humanized albumin mice, mouse and human albumin levels were measured in plasma samples using human and mouse serum albumin ELISA kits (Abcam ab179887 and ab207620, respectively). The humanized mice used for the validation were F1 mice in which the self-deleting selection cassette was self-deleted. Human albumin protein was detected in normal human plasma and humanized albumin mouse plasma samples but not in wild type (WT) mouse or VelocImmune (VI) mouse plasma samples. See FIG. 4. Mouse albumin protein was detected in wild type mouse plasma samples and VI mouse plasma samples but not in humanized albumin mice plasma samples. See FIG. 5. In particular, pooled normal human plasma (purchased from George King-Biomedical Inc.) had about 30-40 mg/mL of human albumin. Humanized albumin mice plasma had about 10-15 mg/mL of human albumin, but mouse albumin was not detectable. Normal VI and WT mouse plasma had about 7-13 mg/mL of mouse albumin.

Example 3. Validation of Mice Comprising a Humanized Albumin (ALB) Locus—Guide RNAs Targeting Human Albumin for F9 Insertion To further validate the humanized albumin mice, the humanized albumin mice were used to evaluate the use of CRISPR/Cas9 technology to integrate a F9 transgene into the albumin locus. Specifically, we tested integration and expression of integrated human F9 Padua variant (hF9-R338L) in homozygous humanized albumin mice. Various guide RNAs were designed against intron 1 of the human albumin locus. Two separate mouse experiments were set up using the ALB$^{hu/hu}$ mice to screen a total of 11 guide RNAs, each targeting the first intron of the human albumin locus. All mice were weighed and injected via tail vein at day 0 of the experiment. Blood was collected at weeks 1, 3, 4, and 6 via tail bleed, and plasma was separated. Mice were terminated at week 7. Blood was collected via the vena cava, and plasma was separated. Livers and spleens were dissected as well. The guide sequences (DNA-targeting segments) of these guide RNAs are provided in Table 5.

TABLE 5

Human Albumin gRNA Sequences and Chromosomal Coordinates.

| Guide ID | Guide Sequence | Human Genomic Coordinates (hg38) | SEQ ID NO: |
|---|---|---|---|
| G009844 | GAGCAACCUCACUCUUGUCU | chr4: 73405113-73405133 | 49 |
| G009852 | UGCAUUUGUUUCAAAAUAUU | chr4: 73404999-73405019 | 50 |
| G009857 | AUUUAUGAGAUCAACAGCAC | chr4: 73404761-73404781 | 51 |
| G009859 | UUAAAUAAAGCAUAGUGCAA | chr4: 73404727-73404747 | 52 |
| G009860 | UAAAGCAUAGUGCAAUGGAU | chr4: 73404722-73404742 | 53 |
| G009874 | UAAUAAAAUUCAAACAUCCU | chr4: 73404561-73404581 | 54 |
| G012752 | UGACUGAAACUUCACAGAAU | chr4: 73404664-73404684 | 55 |
| G012753 | GACUGAAACUUCACAGAAUA | chr4: 73404665-73404685 | 56 |
| G012761 | AGUGCAAUGGAUAGGUCUUU | chr4: 73404714-73404734 | 57 |
| G012764 | CCUCACUCUUGUCUGGGCAA | chr4: 73405107-73405127 | 58 |
| G012765 | ACCUCACUCUUGUCUGGGCA | chr4: 73405108-73405128 | 59 |
| G012766 | UGAGCAACCUCACUCUUGUC | chr4: 73405114-73405134 | 60 |

In the first experiment, the LNPs comprising Cas9 mRNAs and each of the following six guide RNAs separately were tested: G009852, G009859, G009860, G009864, G009874, and G012764. LNPs were diluted to 0.3 mg/kg (using an average weight of 30 grams) and co-injected with AAV8 packaged with a bi-directional hF9 insertion template (SEQ ID NO: 63; ITR-splice acceptor-hF9 (exons 2-8)-bGH-SV40 polyA-codon optimized hF9-pLac-pMB-splice acceptor-Kan resistance) at a dose of 3E11 viral genomes per mouse. Five ALB$^{hu/hu}$ male mice between 12 and 14 weeks old were injected per group. Five mice from same cohort were injected with AAV8 packaged with a CAGG promoter operably linked to hF9 (SEQ ID NO: 64; CAGG-ITR-hF9-WPRE-bGH-ITR-pLac-pMB-Amp resistance), which leads to episomal expression of hF9 (at 3E11 viral genomes per mouse). There were three negative control groups with three mice per group that were injected with buffer alone, AAV8 packaged with the bi-directional hF9 insertion template alone, or LNP-G009874 alone.

In the second experiment, the LNPs comprising Cas9 mRNAs and each of the following six guide RNAs separately were tested: G009860, G012764, G009844, G009857, G012752, G012753, and G012761. LNPs were diluted to 0.3 mg/kg (using an average weight of 40 grams) and co-injected with AAV8 packaged with the bi-directional hF9 insertion template (SEQ ID NO: 63) at a dose of 3E11 viral genomes per mouse. Five ALB$^{hu/hu}$ male mice 30 weeks old were injected per group. Five mice from same cohort were injected with AAV8 packaged with a CAGG promoter operably linked to hF9 (SEQ ID NO: 64), which leads to episomal expression of hF9 (at 3E11 viral genomes per mouse). There were three negative control groups with three mice per group that were injected with buffer alone, AAV8 packaged with the bi-directional hF9 insertion template alone, or LNP-G009874 alone.

Figure 6A:
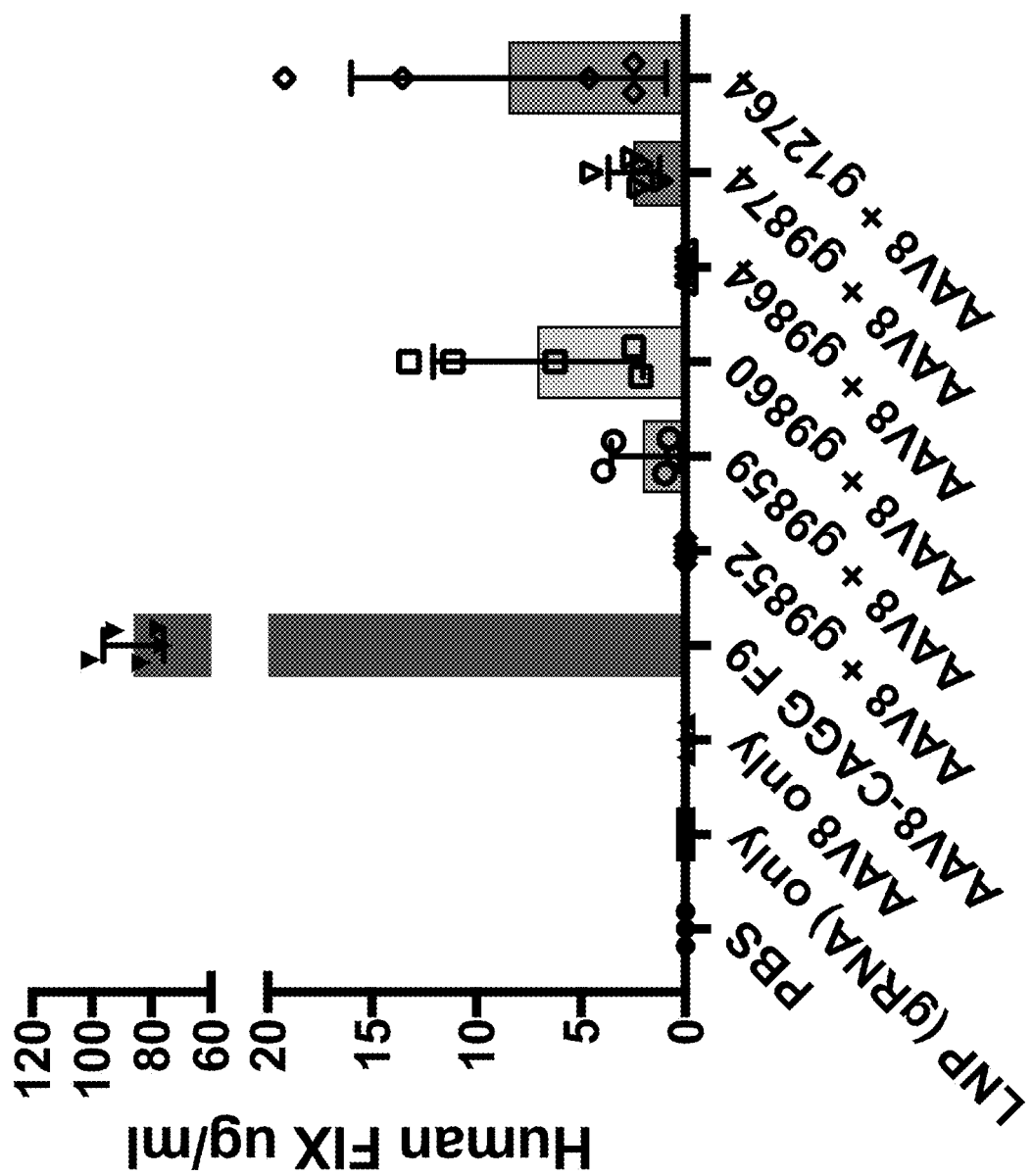
FIGS. 6A and 6B show human Factor IX plasma levels from AAV-hF9 insertion in humanized albumin mice.
Figure 6B:
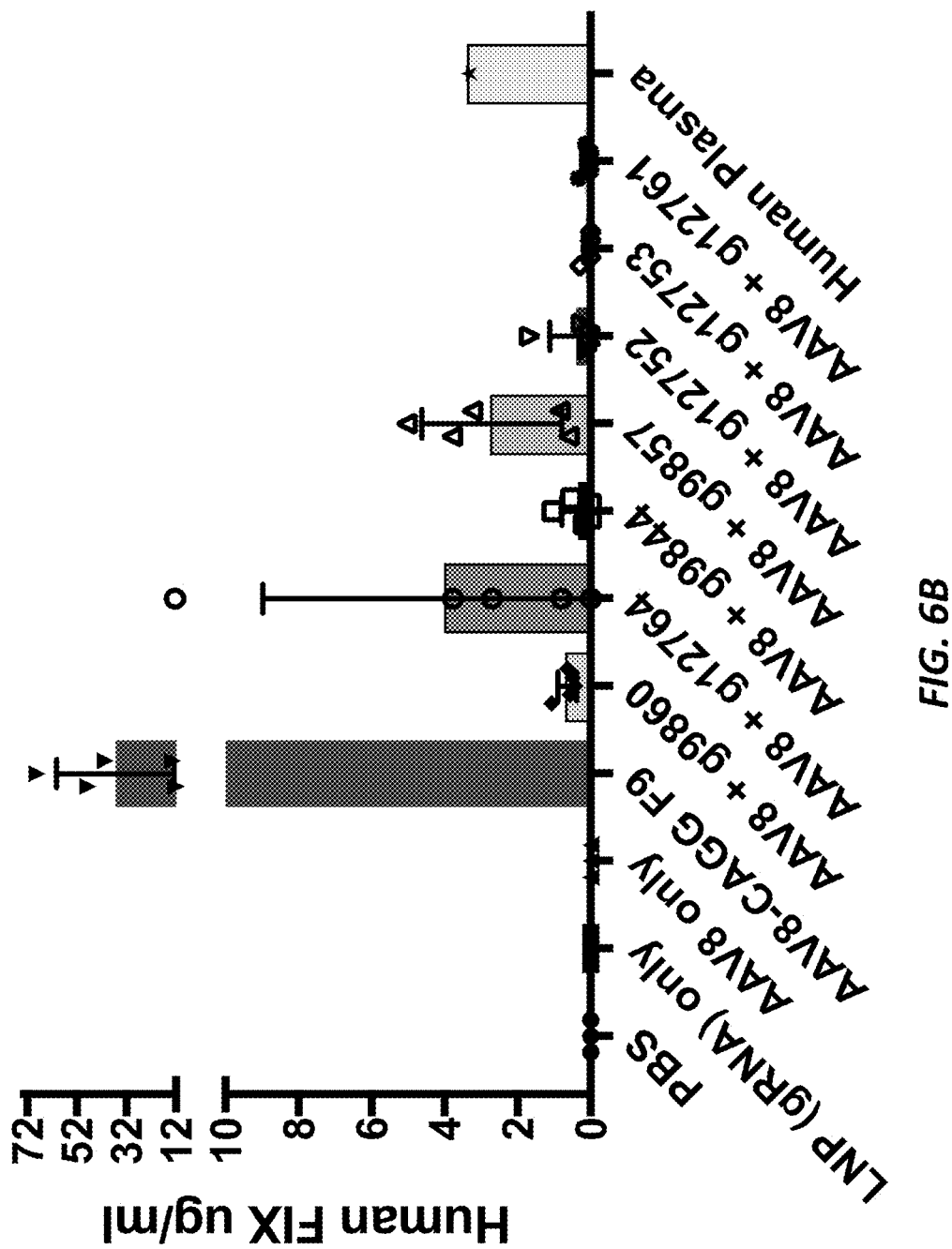

For analysis, an ELISA was performed to measure levels of hFIX circulating in the mice at each timepoint. Human Factor IX ELISA Kits (ab188393) were used for this purpose, and all plates were run with human pooled normal plasma from George King Bio-Medical as a positive assay control. Human Factor IX expression levels in the plasma samples in each group at week 6 post-injection are shown in FIGS. 6A and 6B. Consistent with the in vitro insertion data, low to no Factor IX serum levels were not detected when guide RNA G009852 was used. Consistent with the lack of an adjacent PAM sequence in human albumin, Factor IX serum levels were not detectable when guide RNA G009864 was used. The guide sequence (DNA-targeting segment) of G009864 is (SEQ ID NO: 61)
UACUUUGCACUUUCCUUAGU, and it targets cyno genomic coordinates (mf5) chr5: 61199187-61199207. Factor IX expression in the serum was observed for several of the other guide RNAs, including G009857, G009859, G009860, G009874, and G012764.

Spleens and a portion of the left lateral lobe of all livers were submitted for next-generation sequencing (NGS) analysis. NGS was used to assess the percentage of liver cells with insertions/deletions (indels) at the humanized albumin locus at week 7 post-injection with AAV-hF9 donor and LNP-CRISPR/Cas9. Consistent with the lack of an adjacent PAM sequence in human albumin, no editing was detectable in the liver when guide RNA G009864 was used. Editing in the liver was observed for the groups using guide RNAs G009859, G009860, G009874, and G012764 (data not shown).

Figure 7:
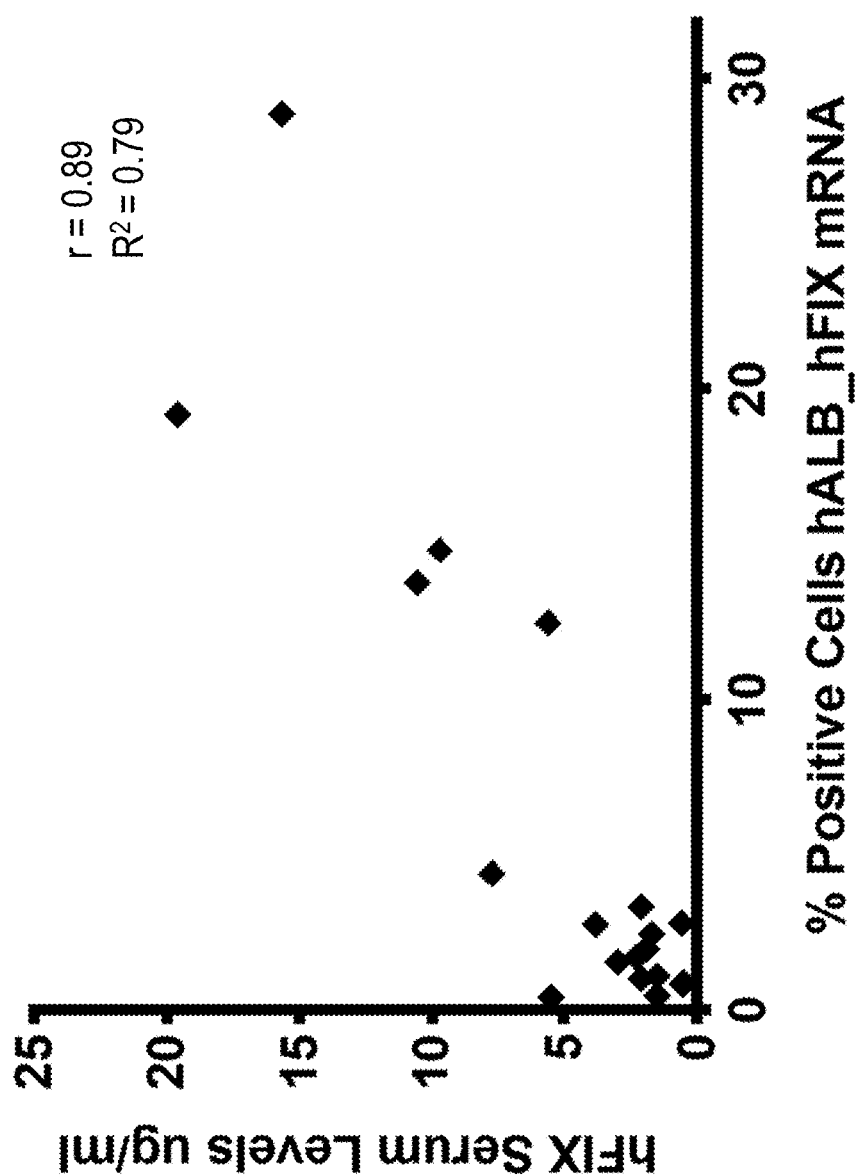
FIG. 7 shows human Factor IX plasma levels at week 7 post-injection with AAV-hF9 donor and LNP-CRISPR/Cas9 plotted against the percentage of cells positive for hALB-hFIX mRNA as determined by BASESCOPE™.

The remaining liver was fixed for 24 hours in 10% neutral buffered formalin and then transferred to 70% ethanol. Four to five samples from separate lobes were cut and shipped to HistoWisz and were processed and embedded in paraffin blocks. Five-micron sections were then cut from each paraffin block, and BASESCOPE™ was performed on the Ventana Ultra Discovery (Roche) using the universal BASESCOPE™ procedure and reagents by Advanced Cell Diagnostics and a custom designed probe that targets the unique mRNA junction formed between the human albumin signal sequence from the first intron of the ALB$^{hu/hu}$ albumin locus and the hF9 transgene when successful integration and transcription is achieved. HALO imaging software (Indica Labs) was then used to quantify the percentage of positive cells in each sample. The average of percentage positive cells across the multiple lobes for each animal was then correlated to the hFIX levels in the serum at week 7. The results are shown in FIG. 7 and Table 6. The week 7 serum levels and the % positive cells for the hALB-hFIX mRNA strongly correlated (r=0.89; R²=0.79).

TABLE 6

Week 7 hFIX and BASESCOPE ™ Data.

| Mouse | Guide | hFIX ug/mL (Week 7) | % mRNA Probe (4-5 Sections) | STD % mRNA Probe | Total Cells Counted |
|---|---|---|---|---|---|
| 1 | Buffer | ND | 0.09 | 0.03 | 152833 |
| 4 | AAV Only | ND | 0.53 | 0.67 | 351084 |
| 7 | LNP Only | ND | 0.48 | 0.33 | 75160 |
| 10 | CAG F9 | 211.8 | 0.20 | 0.22 | 190277 |
| 15 | G009852 | ND | 0.30 | 0.09 | 144518 |
| 20 | G009859 | 0.5 | 0.82 | 0.45 | 143817 |
| 21 | G009859 | 0.5 | 0.88 | 0.43 | 160172 |
| 22 | G009859 | 2.3 | 1.71 | 1.54 | 26015 |
| 23 | G009859 | 3.8 | 2.74 | 0.59 | 183085 |
| 24 | G009859 | 0.6 | 2.78 | 1.96 | 152424 |
| 25 | G009860 | 5.6 | 12.46 | 5.80 | 78935 |
| 26 | G009860 | 10.6 | 13.76 | 5.32 | 112252 |
| 27 | G009860 | 9.7 | 14.80 | 5.45 | 201592 |
| 28 | G009860 | 2.1 | 3.32 | 0.76 | 84710 |
| 29 | G009860 | 3.0 | 1.52 | 0.35 | 203277 |
| 30 | G009864 | ND | 1.94 | 1.78 | 145807 |
| 35 | G009874 | 1.7 | 2.42 | 1.14 | 126665 |
| 36 | G009874 | 1.5 | 1.08 | 0.53 | 195861 |
| 37 | G009874 | 2.1 | 1.02 | 1.29 | 181679 |
| 38 | G009874 | 5.5 | 0.40 | 0.43 | 175359 |
| 39 | G009874 | 1.5 | 0.44 | 0.18 | 205417 |
| 40 | G012764 | 15.7 | 28.85 | 7.11 | 167824 |
| 41 | G012764 | 19.6 | 19.17 | 8.23 | 70081 |
| 42 | G012764 | 1.9 | 1.95 | 1.79 | 154742 |
| 43 | G012764 | 7.7 | 4.38 | 0.68 | 114060 |
| 44 | G012764 | 3.0 | 1.64 | 1.04 | 238623 |
| 43 | DapB (−) | — | 0.12 | 0.07 | 144730 |

Example 4. Validation of Mice Comprising a Humanized Albumin (ALB) Locus-F9 Insertion in F9 KO Mice To further validate the humanized albumin mice, the humanized albumin mice were crossed with F9 knockout mice to create ALB$^{m/hu}$×F9$^{-/-}$ mice (heterozygous for humanization of albumin locus and homozygous F9 knockout) to be used to evaluate the use of CRISPR/Cas9 technology to integrate a F9 transgene into the albumin locus.

The humanized albumin F9 KO mice were then used to test insertion of a human F9 Padua variant (hF9-R338L) transgene into intron 1 of the humanized albumin locus. All mice were weighed and injected via tail vein at day 0 of the experiment. Blood was collected at weeks 1 and 3 via tail bleed, and plasma was separated. Mice were terminated at week 4. Blood was collected via the vena cava, and plasma was separated. Livers and spleens were dissected as well.

LNPs comprising Cas9 mRNA and the following two guide RNAs separately were tested: G009860 (targeting the first intron of the human albumin locus) and G000666 (targeting the first intron of the mouse albumin locus). The guide sequence (DNA-targeting segment) of G009860 is provided in Table 5. The guide sequence of G000666 is (SEQ ID NO: 62)
CACUCUUGUCUGUGGAAACA, and it targets mouse genomic coordinates (mm10) chr5: 90461709-90461729. G009860 was diluted to 0.3 mg/kg, and G000666 was diluted to 1.0 mg/kg (using an average weight of 31.2 grams), and both were co-injected with AAV8 packaged with a bi-directional hF9 insertion template (SEQ ID NO: 63) at a dose of 3E11 viral genomes per mouse. Five ALB$^{ms/hu}$×F9$^{-/-}$ male mice (16 weeks old) were injected per group. Five mice from same cohort were injected with AAV8 packaged with a CAGG promoter operably linked to hF9 (SEQ ID NO: 64), which leads to episomal expression of hF9 (at 3E11 viral genomes per mouse). There were six negative control animals with one mouse per group that was injected with buffer alone or AAV8 packaged with the bi-directional hF9 insertion template alone, and two mice per group that were injected with LNP-G009860 or LNP-G000666 alone at 0.3 mg/kg and 1.0 mg/kg, respectively.

For analysis, an ELISA was performed to measure levels of hFIX circulating in the mice at each timepoint. Human Factor IX ELISA Kits (ab188393) were used for this purpose, and all plates were run with human pooled normal plasma from George King Bio-Medical as a positive assay control. Spleens and a portion of the left lateral lobe of all livers were submitted for NGS analysis.

Figure 8:
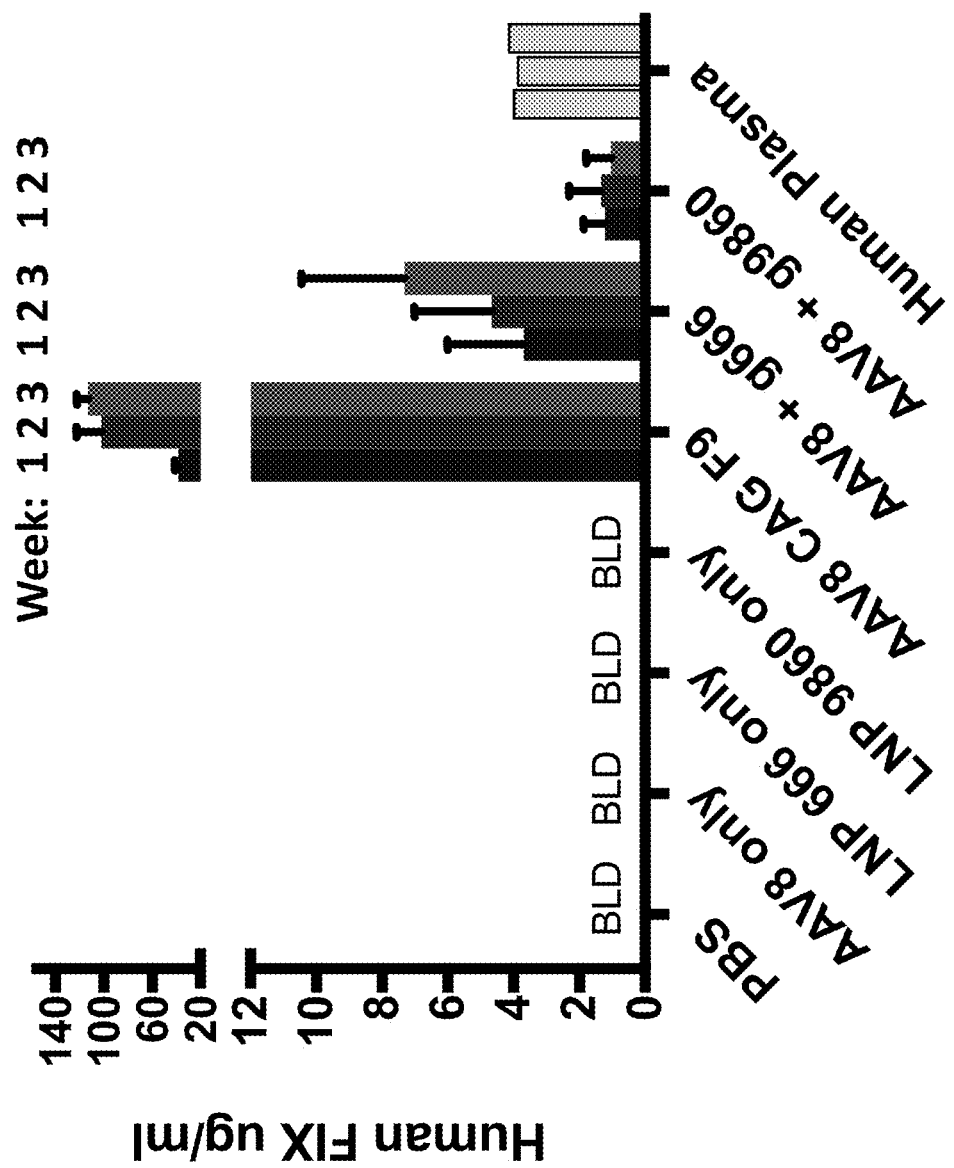
FIG. 8 shows human Factor IX plasma levels from AAV-hF9 insertion in ALB$^{m/hu}$×F9$^{-/-}$ mice.

Human Factor IX expression levels in the plasma samples in each group at weeks 1, 2, and 4 post-injection are shown in FIG. 8 and in Table 7. In addition, NGS results showing insertion and deletion (indel) levels at the albumin locus in the liver and spleen are shown in Table 7. As shown in FIG. 8 and Table 7, hFIX was detected in the plasma of treated A/b$^{+/hu}$/F9$^{-/-}$ mice at 1, 3, and 4 weeks, with ELISA showing expression values of 0.5-10 µg/mL at 1, 3 and 4 weeks.

TABLE 7

Human FIX Plasma Levels and NGS Results.

| Sample | Week 1 (µg/mL) | Week 3 (µg/mL) | Week 4 (µg/mL) | INDEL Liver | INDEL Spleen |
|---|---|---|---|---|---|
| S1 PBS | BLD | BLD | BLD | ND | 0.12 |
| S18 AAV8 only | BLD | BLD | BLD | 0.73 | 0.10 |
| S2 G000666 only | BLD | BLD | BLD | 37.48 | 0.92 |
| S4 G000666 only | BLD | BLD | BLD | 30.67 | 1.17 |
| S19 G009860 only | BLD | BLD | BLD | 12.25 | 0.31 |
| S20 G009860 only | BLD | BLD | BLD | 10.73 | 0.45 |
| S10 CAG | 42.60 | 129.83 | 117.74 | 1.45 | 0.12 |
| S14 CAG | 35.55 | 82.25 | 100.95 | 0.08 | 0.11 |
| S15 CAG | 37.30 | 115.51 | 107.26 | 0.10 | 0.05 |
| S16 CAG | 36.39 | 81.27 | 116.24 | 0.05 | 0.10 |
| S17 CAG | 40.50 | 101.38 | 124.15 | 0.16 | 0.06 |
| S5 AAV8 + G000666 | 2.90 | 5.00 | 8.79 | 41.46 | 1.43 |
| S6 AAV8 + G000666 | 4.67 | 6.11 | 10.29 | 33.81 | 1.59 |
| S7 AAV8 + G000666 | 2.88 | 3.15 | 3.01 | 33.47 | 1.04 |
| S8 AAV8 + G000666 | 0.94 | 1.61 | No sample | 36.54 | 1.34 |
| S9 AAV8 + G000666 | 7.14 | 7.53 | 7.23 | 30.63 | 1.38 |
| S11 AAV8 + G009860 | 0.73 | 0.62 | 0.86 | 11.15 | 0.52 |
| S12 AAV8 + G009860 | 0.52 | 0.43 | 0.47 | 7.05 | 0.39 |
| S13 AAV8 + G009860 | 1.71 | 1.89 | 0.93 | 18.38 | 0.57 |
| S21 AAV8 + G009860 | 1.21 | 2.79 | 0.59 | 13.44 | 0.22 |
| S22 AAV8 + G009860 | 2.06 | 1.03 | 2.37 | 18.06 | 0.19 |
| Human | 4.00 | 3.91 | 4.12 | N/A | N/A |

The remaining liver was fixed for 24 hours in 10% neutral buffered formalin and then transferred to 70% ethanol. Four to five samples from separate lobes were cut and shipped to HistoWiz and were processed and embedded in paraffin blocks. Five-micron sections were then cut from each paraffin block for analysis via BASESCOPE™ on the Ventana Ultra Discovery (Roche) using the universal BASESCOPE™ procedure and reagents by Advanced Cell Diagnostics and a custom designed probe that targets the unique mRNA junction formed between either the human or the mouse albumin signal sequence from the first intron of each respective albumin locus in the ALB$^{ms/hu}$ mice and the hF9 transgene when successful integration and transcription is achieved. HALO imaging software (Indica Labs) is used to quantify the percentage of positive cells in each sample.

Next, terminal blood was used for assessment of functional coagulation activity by activated partial thromboplastin time (aPTT) and Thrombin Generation Assay (TGA). Activated partial thromboplastin time (aPTT) is a clinical measurement of intrinsic pathway clotting activity in plasma. Plasma is induced to clot by the addition of ellagic acid or kaolin, both of which activate coagulation factor XII in the intrinsic pathway (as known as the contact pathway) of coagulation, that subsequently results in the generation of fibrin from fibrinogen once thrombin is activated. The aPTT assay provides an estimation of an individual's ability to generate a clot, and this information can be used to determine risk of bleeding or thrombosis. To test aPTT, a semi-automated benchtop system (Diagnostica Stago STart 4) with an electro-mechanical clot detection method (viscosity-based detection system) was used to assess clotting in plasma. To each cuvette with a steel ball, 50 µL of citrated plasma was added and incubated at 37° C. for 5 min, and then clotting was triggered with the addition of 50 µL of ellagic acid (final concentration of 30 µM) at 37° C. for 300 seconds. Following final activation of clotting by adding 50 µL of 0.025 M calcium chloride (final concentration of 8 mM) to each cuvette, the steal ball began to oscillate back and forth between the two drive coils. The movement of the ball was detected by the receiver coil. The generation of fibrin increased plasma viscosity until the ball ceased to move, which was recorded as the clotting time. The only parameter measured was clotting time. Runs were conducted in duplicate.

Thrombin generation assay (TGA) is a non-clinical assessment of the kinetics of thrombin generation in activated plasma. Thrombin generation is an essential process of coagulation because thrombin is responsible for activation of other coagulation factors and propagation of additional thrombin (via FXI activation) for the conversion of fibrinogen to fibrin. Thrombin generation assay provides an estimation of an individual's ability to generate thrombin, and this information can be used to determine risk of bleeding or thrombosis. To perform the TGA, a calibrated automated thrombogram was used to assess thrombin generation levels in a spectrophotometer (Thrombinograph™, Thermo Scientific). For high throughput experimentation, 96-well plates (Immulon II FIB) were used. To each well, 55 µL of citrated plasma (4× diluted with saline for mouse plasma) was added and incubated at 37° C. for 30 min. Thrombin generation is triggered with the addition of 15 µL of 2 µM ellagic acid (final concentration of 0.33 µM) at 37° C. for 45 min. Thrombin generation was determined following the automated injection of 15 µL of the fluorogenic substrate with 16 mM CaCl$_2$) (FluCa; Thrombinoscope BV) into each well. The fluorogenic substrate reacted with the generated thrombin, which was measured continuously in the plasma every 33 sec for 90 min at 460 nm. The fluorescence intensity was proportional to the proteolytic activity of thrombin. The main parameters measured in the tracing were lag time, peak thrombin generation, time to peak thrombin generation, and endogenous thrombin potential (ETP). The lag time provides an estimation of time required for initial detection of thrombin in plasma. The peak is the maximum amount of thrombin generated at a given time after activation. Time to peak thrombin generation is time from initiation of the coagulation cascade to the peak generation of thrombin. ETP is the total amount of thrombin generated during the 60 minutes measured. Runs were conducted in duplicate.

Figure 9:
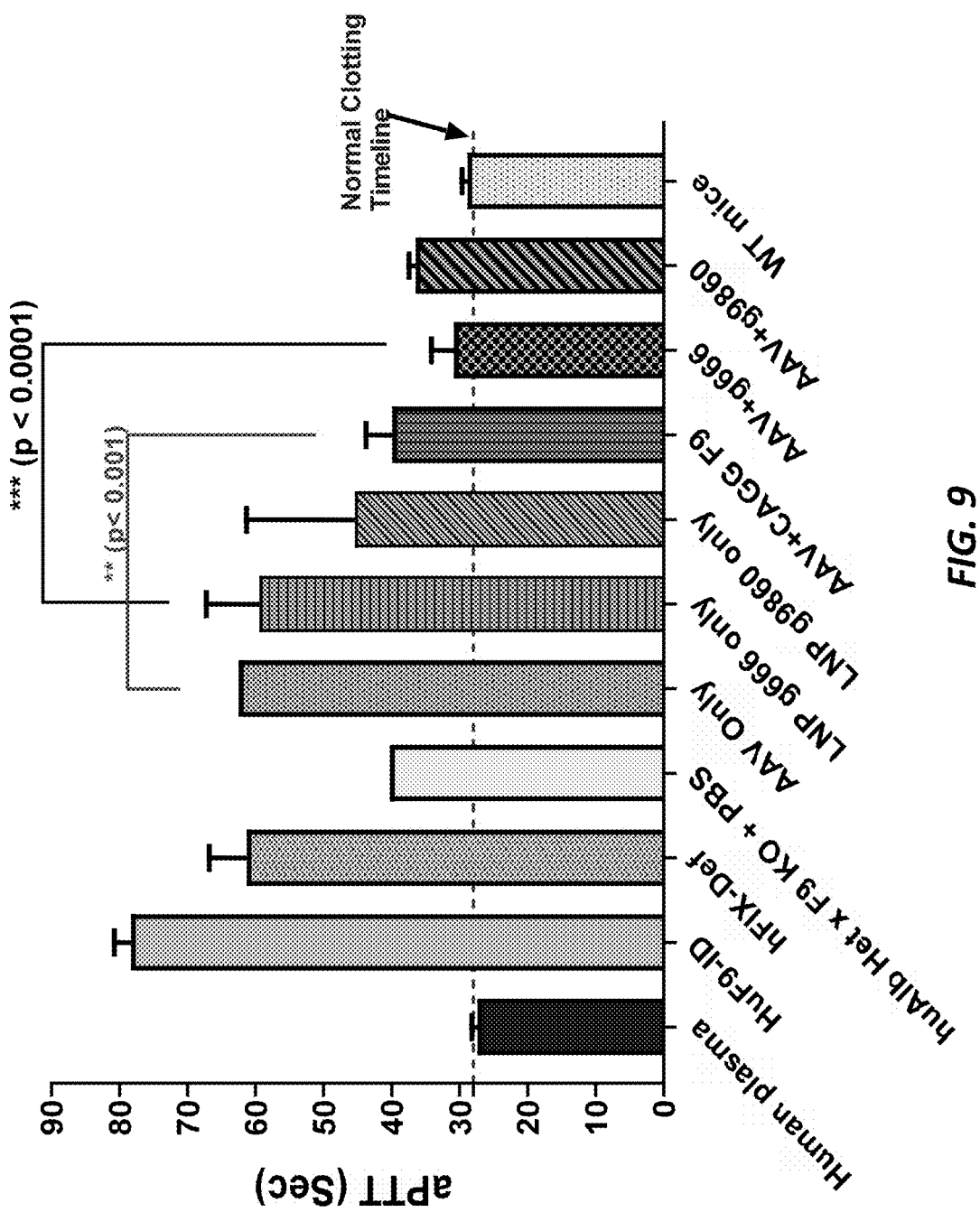
FIG. 9 shows aPTT effects in human and mouse plasma samples from AAV-hF9 insertion in ALB$^{m/hu}$×F9$^{-/-}$ mice.

As shown in FIG. 9 and Table 8, insertion of the hF9 transgene using either the mouse albumin gRNA or the human albumin gRNA showed recovered clotting function in the aPTT assay. Saline, AAV only, and LNP only negative control samples showed prolonged aPTT times of 45-60 seconds. The positive control CAGG and test samples (AAV8+LNP) were closer to the normal human aPTT of 28-34 seconds.

TABLE 8 aPTT and TGA-EA.

| Sample # | I.V. Injection | Week 4 F9 µg/m L | Average aPTT (sec) | TGA-EA Peak (nM) |
|---|---|---|---|---|
| 1 | PBS | BLD | 40.2 | 11.13 |
| 18 | AAV Only | BLD | 62.5 | −1 |
| 2 | LNP G000666 only | BLD | 53.9 | −1 |
| 4 | LNP G000666 only | BLD | 65.0 | 2.45 |
| 19 | LNP G009860 only | BLD | 34.1 | 42.83 |
| 20 | LNP G009860 only | BLD | 56.7 | 18.07 |
| 10 | AAV + CAGG F9 | 117.74 | 41.1 | 42.65 |
| 14 | AAV + CAGG F9 | 100.95 | 34.1 | 49.96 |
| 15 | AAV + CAGG F9 | 107.26 | 42.2 | 49.49 |
| 16 | AAV + CAGG F9 | 116.24 | 37.9 | 44.46 |
| 17 | AAV + CAGG F9 | 124.15 | 44.1 | 38.02 |
| 5 | AAV + G000666 | 8.79 | 31.3 | 72.11 |
| 6 | AAV + G000666 | 10.29 | 32.6 | 90.14 |
| 7 | AAV + G000666 | 3.01 | 33.5 | 58.33 |
| 8 | AAV + G000666 | no sample | NA | NA |
| 9 | AAV + G000666 | 7.23 | 25.9 | 67.23 |

TABLE 8-continued aPTT and TGA-EA.

| Sample # | I.V. Injection | Week 4 F9 µg/m L | Average aPTT (sec) | TGA-EA Peak (nM) |
|---|---|---|---|---|
| 11 | AAV + G009860 | 0.86 | 36.8 | 56.92 |
| 12 | AAV + G009860 | 0.47 | 37.7 | 45.16 |
| 13 | AAV + G009860 | 0.93 | 35.3 | 60.45 |
| 21 | AAV + G009860 | 0.59 | 36.1 | 47.44 |
| 22 | AAV + G009860 | 2.37 | >300 | Clots in tube |

Figure 10A:
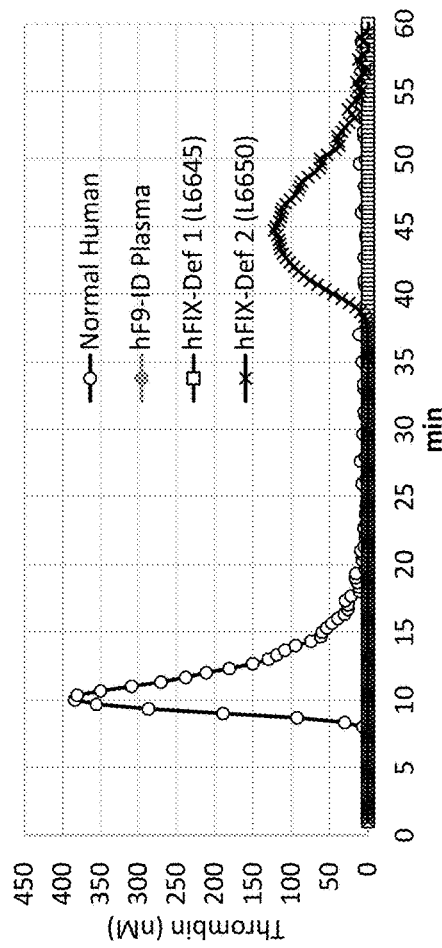
FIGS. 10A and 10B show TGA-EA profiles.
Figure 10B:
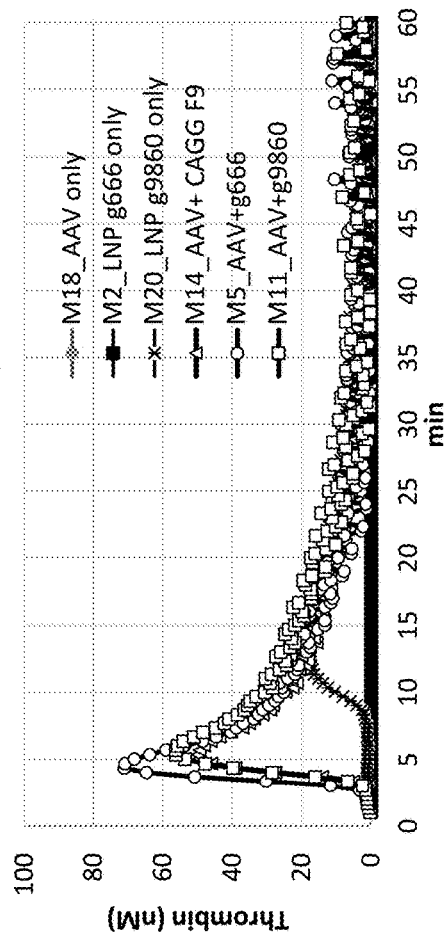
Figure 11:
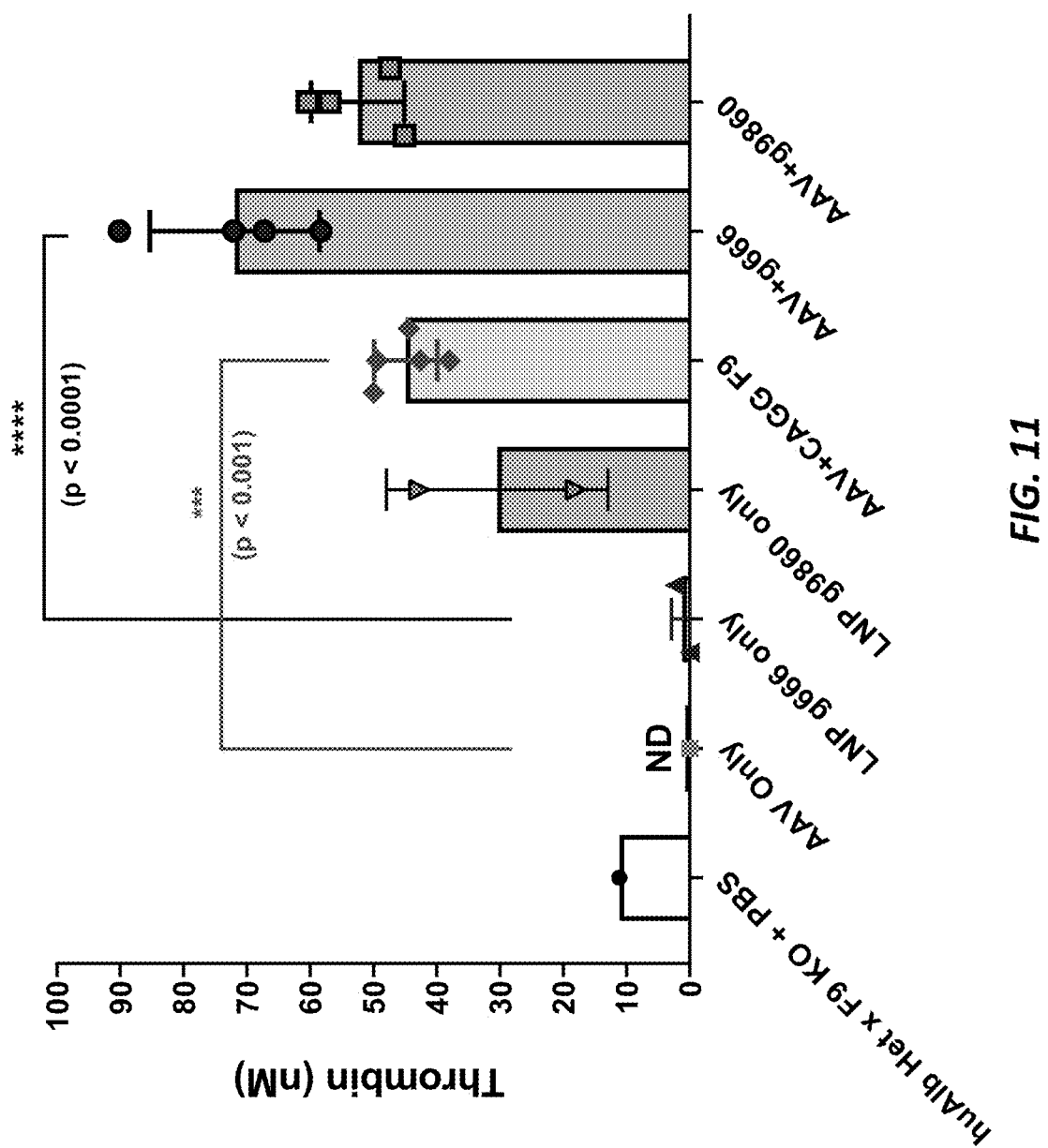
FIG. 11 shows thrombin generation in mouse plasma samples from AAV-hF9 insertion in ALB$^{m/hu}$×F9$^{-/-}$ mice.

As shown in FIGS. 10A, 10B, and 11 and in Table 8, insertion of the hF9 transgene using either the mouse albumin gRNA or the human albumin gRNA showed increased thrombin generation in TGA-EA analysis. Thrombin concentrations were higher in the positive control CAGG and AAV8+LNP as compared to the negative control samples.

In conclusion, hFIX was detected in the plasma of $Alb^{+/hu}/F9^{-/-}$ mice at 1, 3, and 4 weeks, and the expressed hFIX-R338L was found to be functional since thrombin was generated in a TGA assay, and aPTT clotting time was improved.

We claim:

1. A genetically modified mouse whose genome comprises a humanized albumin gene in which the region from the start codon to the stop codon of an endogenous albumin gene is replaced with a human nucleic acid sequence encoding human albumin and a human albumin signal peptide, wherein the human nucleic acid sequence is operably linked to an endogenous albumin promoter and comprises the region from the start codon to the stop codon of a human albumin gene, and wherein the mouse functionally expresses human albumin and has a serum level of human albumin that is at least as high as the serum level of mouse albumin in a wild type mouse.

2. The genetically modified mouse of claim 1, wherein the humanized albumin gene comprises a human albumin 3' untranslated region.

3. The genetically modified mouse of claim 1, wherein the humanized albumin gene comprises the nucleic acid sequence of SEQ ID NO: 17, 18, or 35 or encodes the protein of SEQ ID NO: 5.

4. The genetically modified mouse of claim 1, wherein the humanized albumin gene further comprises a selection cassette.

5. The genetically modified mouse of claim 1, wherein the mouse is homozygous for the humanized albumin gene.

6. The genetically modified mouse of claim 1, wherein the mouse is heterozygous for the humanized albumin gene.

7. The genetically modified mouse of claim 1, wherein the mouse comprises serum albumin levels of at least about 10 mg/mL.

8. The genetically modified mouse of claim 1, wherein the mouse further comprises an inactivated factor 9 (F9) gene.

9. A cell isolated from the genetically modified mouse of claim 1.

10. A genetically modified mouse embryonic stem (ES) cell whose genome comprises a humanized albumin gene in which the region from the start codon to the stop codon of an endogenous albumin gene is replaced with a human nucleic acid sequence encoding human albumin and a human albumin signal peptide,
wherein the human nucleic acid sequence is operably linked to an endogenous albumin promoter and comprises the region from the start codon to the stop codon of a human albumin gene, and
wherein a mouse derived from the mouse ES cell is capable of functionally expressing human albumin and having a serum level of human albumin that is at least as high as the serum level of mouse albumin in a wild-type mouse.

11. A targeting vector for generating a genetically modified mouse whose genome comprises a humanized albumin gene, wherein the vector:
comprises a human nucleic acid sequence encoding human albumin and a human albumin signal peptide flanked by homology arms that target a mouse albumin gene, and
is capable of generating a genetically modified mouse whose genome comprises a humanized albumin gene in which the region from the start codon to the stop codon of an endogenous albumin gene is replaced with the human nucleic acid sequence,
wherein the human nucleic acid sequence is operably linked to an endogenous albumin promoter in the humanized albumin gene and comprises the region from the start codon to the stop codon of a human albumin gene, and
wherein the mouse is capable of functionally expressing human albumin and having a serum level of human albumin that is at least as high as the serum level of mouse albumin in a wild-type mouse.

12. A method of making a genetically modified mouse that expresses human albumin, the method comprising:
(a) obtaining a genetically modified mouse embryonic stem (ES) cell whose genome comprises a humanized albumin gene;
(b) injecting the mouse ES cell into a mouse embryo;
(c) transplanting the mouse embryo into a recipient female; and
(d) obtaining a genetically modified mouse from the transplanted mouse embryo, wherein the mouse has a genome comprising the humanized albumin gene in which the region from the start codon to the stop codon of an endogenous albumin gene is replaced with a human nucleic acid sequence encoding human albumin and a human albumin signal peptide,
wherein the human nucleic acid sequence is operably linked to an endogenous albumin promoter and comprises the region from the start codon to the stop codon of a human albumin gene, and
wherein the mouse functionally expresses human albumin and has a serum level of human albumin that is at least as high as the serum level of mouse albumin in a wild-type mouse.

\* \* \* \* \*

UNITED STATES PATENT AND TRADEMARK OFFICE
CERTIFICATE OF CORRECTION

PATENT NO. : 11,622,547 B2
APPLICATION NO. : 16/894302
DATED : April 11, 2023
INVENTOR(S) : Qing Fang et al.

It is certified that error appears in the above-identified patent and that said Letters Patent is hereby corrected as shown below:

On the Title Page

Item (73) Assignee:
Delete "Regeneran" and replace it with --Regeneron--

Signed and Sealed this
Thirteenth Day of June, 2023

Katherine Kelly Vidal
Director of the United States Patent and Trademark Office

SEQUENCE LISTING

<160> NUMBER OF SEQ ID NOS: 64

<210> SEQ ID NO 1
<211> LENGTH: 608
<212> TYPE: PRT
<213> ORGANISM: Mus musculus
<220> FEATURE:
<221> NAME/KEY: MISC_FEATURE
<222> LOCATION: (1)..(18)
<223> OTHER INFORMATION: Signal Peptide
<220> FEATURE:
<221> NAME/KEY: MISC_FEATURE
<222> LOCATION: (19)..(24)
<223> OTHER INFORMATION: Propeptide
<220> FEATURE:
<221> NAME/KEY: MISC_FEATURE
<222> LOCATION: (25)..(608)
<223> OTHER INFORMATION: Serum Albumin

<400> SEQUENCE: 1

Met Lys Trp Val Thr Phe Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala
    50                  55                  60

Lys Leu Val Gln Glu Val Thr Asp Phe Ala Lys Thr Cys Val Ala Asp
65                  70                  75                  80

Glu Ser Ala Ala Asn Cys Asp Lys Ser Leu His Thr Leu Phe Gly Asp
                85                  90                  95

Lys Leu Cys Ala Ile Pro Asn Leu Arg Glu Asn Tyr Gly Glu Leu Ala
            100                 105                 110

Asp Cys Cys Thr Lys Gln Glu Pro Glu Arg Asn Glu Cys Phe Leu Gln
        115                 120                 125

His Lys Asp Asp Asn Pro Ser Leu Pro Pro Phe Glu Arg Pro Glu Ala
    130                 135                 140

```
Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
            165                 170                 175

Glu Leu Leu Tyr Tyr Ala Glu Gln Tyr Asn Glu Ile Leu Thr Gln Cys
        180                 185                 190

Cys Ala Glu Ala Asp Lys Glu Ser Cys Leu Thr Pro Lys Leu Asp Gly
            195                 200                 205

Val Lys Glu Lys Ala Leu Val Ser Ser Val Arg Gln Arg Met Lys Cys
        210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
            245                 250                 255

Lys Leu Ala Thr Asp Leu Thr Lys Val Asn Lys Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Thr Ile Ser Ser Lys Leu Gln Thr Cys Cys Asp
290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
            325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
        370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
            405                 410                 415

Asp Leu Tyr Glu Lys Leu Gly Glu Tyr Gly Phe Gln Asn Ala Ile Leu
        420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
        450                 455                 460

Pro Glu Asp Gln Arg Leu Pro Cys Val Glu Asp Tyr Leu Ser Ala Ile
465                 470                 475                 480

Leu Asn Arg Val Cys Leu Leu His Glu Lys Thr Pro Val Ser Glu His
            485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Glu Lys Glu
        530                 535                 540

Lys Gln Ile Lys Lys Gln Thr Ala Leu Ala Glu Leu Val Lys His Lys
545                 550                 555                 560
```

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
            580                 585                 590

Ser Thr Glu Gly Pro Asn Leu Val Thr Arg Cys Lys Asp Ala Leu Ala
        595                 600                 605

<210> SEQ ID NO 2
<211> LENGTH: 18
<212> TYPE: PRT
<213> ORGANISM: Mus musculus

<400> SEQUENCE: 2

Met Lys Trp Val Thr Phe Leu Leu Leu Phe Val Ser Gly Ser Ala
1               5                   10                  15

Phe Ser

<210> SEQ ID NO 3
<211> LENGTH: 6
<212> TYPE: PRT
<213> ORGANISM: Mus musculus

<400> SEQUENCE: 3

Arg Gly Val Phe Arg Arg
1               5

<210> SEQ ID NO 4
<211> LENGTH: 584
<212> TYPE: PRT
<213> ORGANISM: Mus musculus

<400> SEQUENCE: 4

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

-continued

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
            245                 250                 255

Arg Ala Glu Leu Ala Lys Tyr Met Cys Glu Asn Gln Ala Thr Ile Ser
        260                 265                 270

Ser Lys Leu Gln Thr Cys Cys Asp Lys Pro Leu Leu Lys Lys Ala His
    275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
            580

<210> SEQ ID NO 5
<211> LENGTH: 609
<212> TYPE: PRT
<213> ORGANISM: Homo sapiens
<220> FEATURE:

<221> NAME/KEY: MISC_FEATURE
<222> LOCATION: (1)..(18)
<223> OTHER INFORMATION: Signal Peptide
<220> FEATURE:
<221> NAME/KEY: MISC_FEATURE
<222> LOCATION: (19)..(24)
<223> OTHER INFORMATION: Propeptide
<220> FEATURE:
<221> NAME/KEY: MISC_FEATURE
<222> LOCATION: (25)..(609)
<223> OTHER INFORMATION: Serum Albumin

<400> SEQUENCE: 5

```
Met Lys Trp Val Thr Phe Ile Ser Leu Leu Phe Leu Phe Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350
```

```
Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 6
<211> LENGTH: 18
<212> TYPE: PRT
<213> ORGANISM: Homo sapiens

<400> SEQUENCE: 6

Met Lys Trp Val Thr Phe Ile Ser Leu Leu Phe Leu Phe Ser Ser Ala
1               5                   10                  15

Tyr Ser

<210> SEQ ID NO 7
<211> LENGTH: 6
<212> TYPE: PRT
<213> ORGANISM: Homo sapiens

<400> SEQUENCE: 7

Arg Gly Val Phe Arg Arg
1               5

<210> SEQ ID NO 8
<211> LENGTH: 585
<212> TYPE: PRT
```

<213> ORGANISM: Homo sapiens

<400> SEQUENCE: 8

| | | | | | | | | | | | | | | |
|---|---|---|---|---|---|---|---|---|---|---|---|---|---|---|
| Asp | Ala | His | Lys | Ser | Glu | Val | Ala | His | Arg | Phe | Lys | Asp | Leu | Gly | Glu |
| 1 | | | | 5 | | | | | 10 | | | | | 15 | |
| Glu | Asn | Phe | Lys | Ala | Leu | Val | Leu | Ile | Ala | Phe | Ala | Gln | Tyr | Leu | Gln |
| | | | 20 | | | | | 25 | | | | | 30 | | |
| Gln | Cys | Pro | Phe | Glu | Asp | His | Val | Lys | Leu | Val | Asn | Glu | Val | Thr | Glu |
| | | 35 | | | | | 40 | | | | | 45 | | | |
| Phe | Ala | Lys | Thr | Cys | Val | Ala | Asp | Glu | Ser | Ala | Glu | Asn | Cys | Asp | Lys |
| | 50 | | | | | 55 | | | | | 60 | | | | |
| Ser | Leu | His | Thr | Leu | Phe | Gly | Asp | Lys | Leu | Cys | Thr | Val | Ala | Thr | Leu |
| 65 | | | | | 70 | | | | | 75 | | | | | 80 |
| Arg | Glu | Thr | Tyr | Gly | Glu | Met | Ala | Asp | Cys | Cys | Ala | Lys | Gln | Glu | Pro |
| | | | | 85 | | | | | 90 | | | | | 95 | |
| Glu | Arg | Asn | Glu | Cys | Phe | Leu | Gln | His | Lys | Asp | Asp | Asn | Pro | Asn | Leu |
| | | | 100 | | | | | 105 | | | | | 110 | | |
| Pro | Arg | Leu | Val | Arg | Pro | Glu | Val | Asp | Val | Met | Cys | Thr | Ala | Phe | His |
| | | 115 | | | | | 120 | | | | | 125 | | | |
| Asp | Asn | Glu | Glu | Thr | Phe | Leu | Lys | Lys | Tyr | Leu | Tyr | Glu | Ile | Ala | Arg |
| | 130 | | | | | 135 | | | | | 140 | | | | |
| Arg | His | Pro | Tyr | Phe | Tyr | Ala | Pro | Glu | Leu | Leu | Phe | Phe | Ala | Lys | Arg |
| 145 | | | | | 150 | | | | | 155 | | | | | 160 |
| Tyr | Lys | Ala | Ala | Phe | Thr | Glu | Cys | Cys | Gln | Ala | Ala | Asp | Lys | Ala | Ala |
| | | | | 165 | | | | | 170 | | | | | 175 | |
| Cys | Leu | Leu | Pro | Lys | Leu | Asp | Glu | Leu | Arg | Asp | Glu | Gly | Lys | Ala | Ser |
| | | | 180 | | | | | 185 | | | | | 190 | | |
| Ser | Ala | Lys | Gln | Arg | Leu | Lys | Cys | Ala | Ser | Leu | Gln | Lys | Phe | Gly | Glu |
| | | 195 | | | | | 200 | | | | | 205 | | | |
| Arg | Ala | Phe | Lys | Ala | Trp | Ala | Val | Ala | Arg | Leu | Ser | Gln | Arg | Phe | Pro |
| | 210 | | | | | 215 | | | | | 220 | | | | |
| Lys | Ala | Glu | Phe | Ala | Glu | Val | Ser | Lys | Leu | Val | Thr | Asp | Leu | Thr | Lys |
| 225 | | | | | 230 | | | | | 235 | | | | | 240 |
| Val | His | Thr | Glu | Cys | Cys | His | Gly | Asp | Leu | Leu | Glu | Cys | Ala | Asp | Asp |
| | | | | 245 | | | | | 250 | | | | | 255 | |
| Arg | Ala | Asp | Leu | Ala | Lys | Tyr | Ile | Cys | Glu | Asn | Gln | Asp | Ser | Ile | Ser |
| | | | 260 | | | | | 265 | | | | | 270 | | |
| Ser | Lys | Leu | Lys | Glu | Cys | Cys | Glu | Lys | Pro | Leu | Leu | Glu | Lys | Ser | His |
| | | 275 | | | | | 280 | | | | | 285 | | | |
| Cys | Ile | Ala | Glu | Val | Glu | Asn | Asp | Glu | Met | Pro | Ala | Asp | Leu | Pro | Ser |
| | 290 | | | | | 295 | | | | | 300 | | | | |
| Leu | Ala | Ala | Asp | Phe | Val | Glu | Ser | Lys | Asp | Val | Cys | Lys | Asn | Tyr | Ala |
| 305 | | | | | 310 | | | | | 315 | | | | | 320 |
| Glu | Ala | Lys | Asp | Val | Phe | Leu | Gly | Met | Phe | Leu | Tyr | Glu | Tyr | Ala | Arg |
| | | | | 325 | | | | | 330 | | | | | 335 | |
| Arg | His | Pro | Asp | Tyr | Ser | Val | Val | Leu | Leu | Leu | Arg | Leu | Ala | Lys | Thr |
| | | | 340 | | | | | 345 | | | | | 350 | | |
| Tyr | Glu | Thr | Thr | Leu | Glu | Lys | Cys | Cys | Ala | Ala | Ala | Asp | Pro | His | Glu |
| | | 355 | | | | | 360 | | | | | 365 | | | |
| Cys | Tyr | Ala | Lys | Val | Phe | Asp | Glu | Phe | Lys | Pro | Leu | Val | Glu | Glu | Pro |
| | 370 | | | | | 375 | | | | | 380 | | | | |
| Gln | Asn | Leu | Ile | Lys | Gln | Asn | Cys | Glu | Leu | Phe | Glu | Gln | Leu | Gly | Glu |
| 385 | | | | | 390 | | | | | 395 | | | | | 400 |

```
Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 9
<211> LENGTH: 1827
<212> TYPE: DNA
<213> ORGANISM: Mus musculus
<220> FEATURE:
<221> NAME/KEY: misc_feature
<222> LOCATION: (1)..(72)
<223> OTHER INFORMATION: Signal Peptide
<220> FEATURE:
<221> NAME/KEY: misc_feature
<222> LOCATION: (73)..(90)
<223> OTHER INFORMATION: Propeptide
<220> FEATURE:
<221> NAME/KEY: misc_feature
<222> LOCATION: (91)..(1824)
<223> OTHER INFORMATION: Serum Albumin

<400> SEQUENCE: 9
atgaagtggg taacctttct cctcctcctc ttcgtctccg gctctgcttt ttccagggggt      60 gtgtttcgcc gagaagcaca caagagtgag atcgcccatc ggtataatga tttgggagaa     120
caacatttca aaggcctagt cctgattgcc ttttcccagt atctccagaa atgctcatac     180
gatgagcatg ccaaattagt gcaggaagta acagactttg caaagacgtg tgttgccgat     240
gagtctgccg ccaactgtga caaatcccctt cacactcttt ttggagataa gttgtgtgcc     300
attccaaacc tccgtgaaaa ctatggtgaa ctggctgact gctgtacaaa acaagagccc     360
gaaagaaacg aatgtttcct gcaacacaaa gatgacaacc ccagcctgcc accatttgaa     420
aggccagagg ctgaggccat gtgcacctcc tttaaggaaa acccaaccac ctttatggga     480
cactatttgc atgaagttgc cagaagacat cctatttcct atgccccaga acttctttac     540
tatgctgagc agtacaatga gattctgacc cagtgttgtg cagaggctga caaggaaagc     600
tgcctgaccc cgaagcttga tggtgtgaag gagaaagcat tggtctcatc tgtccgtcag     660
agaatgaagt gctccagtat gcagaagttt ggagagagag cttttaaagc atgggcagta     720
```

```
gctcgtctga gccagacatt ccccaatgct gactttgcag aaatcaccaa attggcaaca      780
gacctgacca aagtcaacaa ggagtgctgc catggtgacc tgctggaatg cgcagatgac      840
agggcggaac ttgccaagta catgtgtgaa aaccaggcga ctatctccag caaactgcag      900
acttgctgcg ataaaccact gttgaagaaa gcccactgtc ttagtgaggt ggagcatgac      960
accatgcctg ctgatctgcc tgccattgct gctgattttg ttgaggacca ggaagtgtgc     1020
aagaactatg ctgaggccaa ggatgtcttc ctgggcacgt tcttgtatga atattcaaga     1080
agacaccctg attactctgt atccctgttg ctgagacttg ctaagaaata tgaagccact     1140
ctggaaaagt gctgcgctga agccaatcct cccgcatgct acggcacagt gcttgctgaa     1200
tttcagcctc ttgtagaaga gcctaagaac ttggtcaaaa ccaactgtga tctttacgag     1260
aagcttggag aatatggatt ccaaaatgcc attctagttc gctacaccca gaaagcacct     1320
caggtgtcaa ccccaactct cgtggaggct gcaagaaacc taggaagagt gggcaccaag     1380
tgttgtacac ttcctgaaga tcagagactg ccttgtgtgg aagactatct gtctgcaatc     1440
ctgaaccgtg tgtgtctgct gcatgagaag accccagtga gtgagcatgt taccaagtgc     1500
tgtagtggat ccctggtgga aaggcggcca tgcttctctg ctctgacagt tgatgaaaca     1560
tatgtcccca agagtttaa agctgagacc ttcaccttcc actctgatat ctgcacactt     1620
ccagagaagg agaagcagat taagaaacaa acggctcttg ctgagctggt gaagcacaag     1680
cccaaggcta cagcggagca actgaagact gtcatggatg actttgcaca gttcctggat     1740
acatgttgca aggctgctga caaggacacc tgcttctcga ctgagggtcc aaaccttgtc     1800
actagatgca aagacgcctt agcctaa                                         1827

<210> SEQ ID NO 10
<211> LENGTH: 72
<212> TYPE: DNA
<213> ORGANISM: Mus musculus

<400> SEQUENCE: 10
atgaagtggg taacctttct cctcctcctc ttcgtctccg gctctgcttt ttccagggg      60 gtgtttcgcc ga                                                         72

<210> SEQ ID NO 11
<211> LENGTH: 18
<212> TYPE: DNA
<213> ORGANISM: Mus musculus

<400> SEQUENCE: 11
gaagcacaca agagtgag                                                   18

<210> SEQ ID NO 12
<211> LENGTH: 1734
<212> TYPE: DNA
<213> ORGANISM: Mus musculus

<400> SEQUENCE: 12
atcgcccatc ggtataatga tttgggagaa caacatttca aaggcctagt cctgattgcc      60 tttttcccagt atctccagaa atgctcatac gatgagcatg ccaaattagt gcaggaagta    120
acagactttg caaagacgtg tgttgccgat gagtctgccg ccaactgtga caaatcccttt    180 cacactcttt ttggagataa gttgtgtgcc attccaaacc tccgtgaaaa ctatggtgaa    240
ctggctgact gctgtacaaa acaagagccc gaaagaaacg aatgtttcct gcaacacaaa    300
```

-continued

| | |
|---|---|
| gatgacaacc ccagcctgcc accatttgaa aggccagagg ctgaggccat gtgcacctcc | 360 |
| tttaaggaaa acccaaccac ctttatggga cactatttgc atgaagttgc cagaagacat | 420 |
| ccttatttct atgccccaga acttctttac tatgctgagc agtacaatga gattctgacc | 480 |
| cagtgttgtg cagaggctga caaggaaagc tgcctgaccc cgaagcttga tggtgtgaag | 540 |
| gagaaagcat tggtctcatc tgtccgtcag agaatgaagt gctccagtat gcagaagttt | 600 |
| ggagagagag cttttaaagc atgggcagta gctcgtctga ccagacatt ccccaatgct | 660 |
| gactttgcag aaatcaccaa attggcaaca gacctgacca agtcaacaa ggagtgctgc | 720 |
| catggtgacc tgctggaatg cgcagatgac agggcggaac ttgccaagta catgtgtgaa | 780 |
| aaccaggcga ctatctccag caaactgcag acttgctgcg ataaaccact gttgaagaaa | 840 |
| gcccactgtc ttagtgaggt ggagcatgac accatgcctg ctgatctgcc tgccattgct | 900 |
| gctgattttg ttgaggacca ggaagtgtgc aagaactatg ctgaggccaa ggatgtcttc | 960 |
| ctgggcacgt tcttgtatga atattcaaga agacaccctg attactctgt atccctgttg | 1020 |
| ctgagacttg ctaagaaata tgaagccact ctggaaaagt gctgcgctga agccaatcct | 1080 |
| cccgcatgct acggcacagt gcttgctgaa tttcagcctc ttgtagaaga gcctaagaac | 1140 |
| ttggtcaaaa ccaactgtga tctttacgag aagcttggag aatatggatt ccaaaatgcc | 1200 |
| attctagttc gctacaccca gaaagcacct caggtgtcaa ccccaactct cgtggaggct | 1260 |
| gcaagaaacc taggaagagt gggcaccaag tgttgtacac ttcctgaaga tcagagactg | 1320 |
| ccttgtgtgg aagactatct gtctgcaatc ctgaaccgtg tgtgtctgct gcatgagaag | 1380 |
| accccagtga gtgagcatgt taccaagtgc tgtagtggat ccctggtgga aaggcggcca | 1440 |
| tgcttctctg ctctgacagt tgatgaaaca tatgtcccca agagtttaa agctgagacc | 1500 |
| ttcaccttcc actctgatat ctgcacactt ccagagaagg agaagcagat taagaaacaa | 1560 |
| acggctcttg ctgagctggt gaagcacaag cccaaggcta cagcggagca actgaagact | 1620 |
| gtcatggatg actttgcaca gttcctggat acatgttgca aggctgctga caaggacacc | 1680 |
| tgcttctcga ctgagggtcc aaaccttgtc actagatgca aagacgcctt agcc | 1734 |

<210> SEQ ID NO 13
<211> LENGTH: 1830
<212> TYPE: DNA
<213> ORGANISM: Homo sapiens
<220> FEATURE:
<221> NAME/KEY: misc_feature
<222> LOCATION: (1)..(72)
<223> OTHER INFORMATION: Signal Peptide
<220> FEATURE:
<221> NAME/KEY: misc_feature
<222> LOCATION: (73)..(90)
<223> OTHER INFORMATION: Propeptide
<220> FEATURE:
<221> NAME/KEY: misc_feature
<222> LOCATION: (91)..(1827)
<223> OTHER INFORMATION: Serum albumin

<400> SEQUENCE: 13

| | |
|---|---|
| atgaagtggg taacctttat ttcccttctt tttctcttta gctcggctta ttccaggggt | 60 |
| gtgtttcgtc gagatgcaca caagagtgag gttgctcatc ggtttaaaga tttgggagaa | 120 |
| gaaaatttca agccttggt gttgattgcc tttgctcagt atcttcagca gtgtccattt | 180 |
| gaagatcatg taaaattagt gaatgaagta actgaatttg caaaaacatg tgttgctgat | 240 |
| gagtcagctg aaaattgtga caaatcactt catacccttt ttggagacaa attatgcaca | 300 |
| gttgcaactc ttcgtgaaac ctatggtgaa atggctgact gctgtgcaaa acaagaacct | 360 |

```
gagagaaatg aatgcttctt gcaacacaaa gatgacaacc caaacctccc ccgattggtg      420
agaccagagg ttgatgtgat gtgcactgct tttcatgaca atgaagagac attttttgaaa    480 aaatacttat atgaaattgc cagaagacat ccttactttt atgccccgga actccttttc     540
tttgctaaaa ggtataaagc tgcttttaca gaatgttgcc aagctgctga taaagctgcc     600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga ccagagatt tcccaaagct gagtttgcag aagtttccaa gttagtgaca     780
gatcttacca aagtccacac ggaatgctgc catggagatc tgcttgaatg tgctgatgac     840
agggcggacc ttgccaagta tatctgtgaa aatcaagatt cgatctccag taaactgaag     900
gaatgctgtg aaaaacctct gttggaaaaa tcccactgca ttgccgaagt ggaaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttgag     1260 cagcttggag agtacaaatt ccagaatgcg ctattagttc gttacaccaa gaaagtaccc    1320
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagctcgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttataa                                       1830

<210> SEQ ID NO 14
<211> LENGTH: 72
<212> TYPE: DNA
<213> ORGANISM: Homo sapiens

<400> SEQUENCE: 14
atgaagtggg taacctttat ttcccttctt tttctcttta gctcggctta ttccaggggt      60
gtgtttcgtc ga                                                          72

<210> SEQ ID NO 15
<211> LENGTH: 18
<212> TYPE: DNA
<213> ORGANISM: Homo sapiens

<400> SEQUENCE: 15
gatgcacaca agagtgag                                                    18

<210> SEQ ID NO 16
<211> LENGTH: 1737
<212> TYPE: DNA
<213> ORGANISM: Homo sapiens
```

<400> SEQUENCE: 16

```
gttgctcatc ggtttaaaga tttgggagaa gaaaatttca aagccttggt gttgattgcc    60
tttgctcagt atcttcagca gtgtccattt gaagatcatg taaaattagt gaatgaagta   120
actgaatttg caaaaacatg tgttgctgat gagtcagctg aaaattgtga caaatcactt   180
catacccttt ttggagacaa attatgcaca gttgcaactc ttcgtgaaac ctatggtgaa   240
atggctgact gctgtgcaaa acaagaacct gagagaaatg aatgcttctt gcaacacaaa   300
gatgacaacc caaacctccc ccgattggtg agaccagagg ttgatgtgat gtgcactgct   360
tttcatgaca atgaagagac atttttgaaa aaatacttat atgaaattgc cagaagacat   420
ccttactttt atgccccgga actccttttc tttgctaaaa ggtataaagc tgcttttaca   480
gaatgttgcc aagctgctga taaagctgcc tgcctgttgc caaagctcga tgaacttcgg   540
gatgaaggga aggcttcgtc tgccaaacag agactcaagt gtgccagtct ccaaaaattt   600
ggagaaagag ctttcaaagc atgggcagta gctcgcctga ccagagatt tcccaaagct   660
gagtttgcag aagtttccaa gttagtgaca gatcttacca aagtccacac ggaatgctgc   720
catggagatc tgcttgaatg tgctgatgac agggcggacc ttgccaagta tatctgtgaa   780
aatcaagatt cgatctccag taaactgaag gaatgctgtg aaaaacctct gttggaaaaa   840
tcccactgca ttgccgaagt ggaaaatgat gagatgcctg ctgacttgcc ttcattagct   900
gctgattttg ttgaaagtaa ggatgttttgc aaaaactatg ctgaggcaaa ggatgtcttc   960
ctgggcatgt ttttgtatga atatgcaaga aggcatcctg attactctgt cgtgctgctg  1020
ctgagacttg ccaagacata tgaaaccact ctagagaagt gctgtgccgc tgcagatcct  1080
catgaatgct atgccaaagt gttcgatgaa tttaaacctc ttgtggaaga gcctcagaat  1140
ttaatcaaac aaaattgtga gctttttgag cagcttggag agtacaaatt ccagaatgcg  1200
ctattagttc gttacaccaa gaaagtaccc caagtgtcaa ctccaactct tgtagaggtc  1260
tcaagaaacc taggaaaagt gggcagcaaa tgttgtaaac atcctgaagc aaaaagaatg  1320
ccctgtgcag aagactatct atccgtggtc ctgaaccagt tatgtgtgtt gcatgagaaa  1380
acgccagtaa gtgacagagt caccaaatgc tgcacagaat ccttggtgaa caggcgacca  1440
tgcttttcag ctctggaagt cgatgaaaca tacgttccca aagagtttaa tgctgaaaca  1500
ttcaccttcc atgcagatat atgcacactt tctgagaagg agagacaaat caagaaacaa  1560
actgcacttg ttgagctcgt gaaacacaag cccaaggcaa caaagagca actgaaagct  1620
gttatggatg atttcgcagc ttttgtagag aagtgctgca aggctgacga taaggagacc  1680
tgctttgccg aggagggtaa aaaacttgtt gctgcaagtc aagctgcctt aggctta    1737
```

<210> SEQ ID NO 17
<211> LENGTH: 23484
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(46)
<223> OTHER INFORMATION: Mouse Sequence
<220> FEATURE:
<221> NAME/KEY: misc_feature
<222> LOCATION: (47)..(17381)
<223> OTHER INFORMATION: Human Sequence
<220> FEATURE:
<221> NAME/KEY: misc_feature
<222> LOCATION: (17382)..(17387)
<223> OTHER INFORMATION: XhoI

```
<220> FEATURE:
<221> NAME/KEY: misc_feature
<222> LOCATION: (17388)..(17421)
<223> OTHER INFORMATION: LoxP
<220> FEATURE:
<221> NAME/KEY: misc_feature
<222> LOCATION: (17422)..(18108)
<223> OTHER INFORMATION: Prm1
<220> FEATURE:
<221> NAME/KEY: misc_feature
<222> LOCATION: (18109)..(19249)
<223> OTHER INFORMATION: Crei
<220> FEATURE:
<221> NAME/KEY: misc_feature
<222> LOCATION: (19250)..(19545)
<223> OTHER INFORMATION: SV40 PolyA
<220> FEATURE:
<221> NAME/KEY: misc_feature
<222> LOCATION: (19546)..(20758)
<223> OTHER INFORMATION: hUbi
<220> FEATURE:
<221> NAME/KEY: misc_feature
<222> LOCATION: (20759)..(20825)
<223> OTHER INFORMATION: em7
<220> FEATURE:
<221> NAME/KEY: misc_feature
<222> LOCATION: (20826)..(21629)
<223> OTHER INFORMATION: Neo
<220> FEATURE:
<221> NAME/KEY: misc_feature
<222> LOCATION: (21630)..(22119)
<223> OTHER INFORMATION: PGK PolyA
<220> FEATURE:
<221> NAME/KEY: misc_feature
<222> LOCATION: (22120)..(22153)
<223> OTHER INFORMATION: LoxP
<220> FEATURE:
<221> NAME/KEY: misc_feature
<222> LOCATION: (22160)..(22185)
<223> OTHER INFORMATION: I-CeuI
<220> FEATURE:
<221> NAME/KEY: misc_feature
<222> LOCATION: (22186)..(22191)
<223> OTHER INFORMATION: NheI
<220> FEATURE:
<221> NAME/KEY: misc_feature
<222> LOCATION: (22192)..(23484)
<223> OTHER INFORMATION: Mouse Sequence

<400> SEQUENCE: 17
tgcacacaga tcacctttcc tatcaacccc actagcctct ggcaaaatga agtgggtaac      60
ctttatttcc cttcttttc tctttagctc ggcttattcc aggggtgtgt ttcgtcgaga     120
tgcacgtaag aaatccattt ttctattgtt caactttat tctatttcc cagtaaaata      180 aagttttagt aaactctgca tctttaaaga attattttgg catttatttc taaaatggca     240
tagtattttg tatttgtgaa gtcttacaag gttatcttat taataaaatt caaacatcct    300
aggtaaaaaa aaaaaaaggt cagaattgtt tagtgactgt aattttcttt tgcgcactaa    360
ggaaagtgca aagtaactta gagtgactga aacttcacag aatagggttg aagattgaat    420
tcataactat cccaaagacc tatccattgc actatgcttt atttaaaaac cacaaaacct    480
gtgctgttga tctcataaat agaacttgta tttatattta ttttcatttt agtctgtctt    540
cttggttgct gttgatagac actaaaagag tattagatat tatctaagtt tgaatataag    600
gctataaata tttaataatt tttaaaatag tattcttggt aattgaatta ttcttctgtt    660
taaaggcaga agaaataatt gaacatcatc ctgagttttt ctgtaggaat cagagcccaa    720 tatttgaaa caaatgcata atctaagtca aatggaaaga aatataaaaa gtaacattat     780
tacttcttgt tttcttcagt atttaacaat cctttttttt cttcccttgc ccagacaaga    840
```

```
gtgaggttgc tcatcggttt aaagatttgg gagaagaaaa tttcaaagcc ttgtaagtta      900
aaatattgat gaatcaaatt taatgtttct aatagtgttg tttattattc taaagtgctt      960
atatttcctt gtcatcaggg ttcagattct aaaacagtgc tgcctcgtag agttttctgc     1020
gttgaggaag atattctgta tctgggctat ccaataaggt agtcactggt cacatggcta     1080
ttgagtactt caaatatgac aagtgcaact gagaaacaaa aacttaaatt gtatttaatt     1140
gtagttaatt tgaatgtata tagtcacatg tggctaatgg ctactgtatt ggacagtaca     1200
gctctggaac ttgcttggtg gaaaggactt taatataggt ttcctttggt ggcttaccca     1260
ctaaatcttc tttacatagc aagcattcct gtgcttagtt gggaatattt aattttttt     1320 ttttttaag acagggtctc gctctgtcgc ccaggctgga gtgcagtggc gcaatctcgg     1380
ctcactgcaa actccgcctc ccgggttcac gccattctcc tgcctcagcc tcccgagtag     1440
ctgggactac aggcgcccgc catcacgccc ggctaatctt ttgtattttt agtagagatg     1500
gggtttcacc gtgtgccagg atggtctcaa tctcctgaca tcgtgatctg cccacctcgg     1560
cctcccaaag tgctgggatt acaggagtga gccaccgcgc ccggcctatt taaatgtttt     1620
ttaatctagt aaaaaatgag aaaattgttt ttttaaaagt ctacctaatc ctacaggcta     1680
attaaagacg tgtgtgggga tcaggtgcgg tggttcacac ctgtaatccc agcactttgg     1740
aaggctgatg caggaggatt gcttgagccc aggagttcaa gaccagcctg ggcaagtctc     1800
tttaaaaaaa acaaaacaaa caaacaaaaa aattaggcat ggtggcacat gcctgtagtc     1860
ctagctactt aggaggctga cgtaggagga tcgtttggac ctgagaggtc aaggctacag     1920
tgagccatga ttgtgccact gcactccagc ctgggtgaca gagtgagact ctgtctcaaa     1980
aaagaaaaag gaaatctgtg gggtttgttt tagttttaag taattctaag gactttaaaa     2040
atgcctagtc ttgacaatta gatctatttg gcatacaatt tgcttgctta atctatgtgt     2100
gtgcatagat ctactgacac acgcatacat ataaacatta gggaactacc attctctttg     2160
cgtaggaagc cacatatgcc tatctaggcc tcagatcata cctgatatga ataggctttc     2220
tggataatgg tgaagaagat gtataaaaga tagaacctat acccatacat gatttgttct     2280
ctagcgtagc aacctgttac atattaaagt tttattatac tacatttttc tacatccttt     2340
gtttcagggt gttgattgcc tttgctcagt atcttcagca gtgtccattt gaagatcatg     2400
taaaattagt gaatgaagta actgaatttg caaaaacatg tgttgctgat gagtcagctg     2460
aaaattgtga caaatcactt gtaagtacat tctaattgtg gagattcttt cttctgtttg     2520
aagtaatccc aagcatttca aaggaatttt ttttaagttt tctcaattat tattaagtgt     2580
cctgatttgt aagaaacact aaaaagttgc tcatagactg ataagccatt gtttctttg     2640 tgatagagat gctttagcta tgtccacagt tttaaaatca tttctttatt gagaccaaac     2700
acaacagtca tggtgtattt aaatggcaat tgtcattta taaacacctc ttttaaaat     2760 ttgaggtttg gtttcttttt gtagaggcta tagggatat gatagcatgt atttatttat     2820
ttatttatct tattttatta tagtaagaac ccttaacatg agatctaccc tgttatattt     2880
ttaagtgtac aatccattat tgttaactac gggtacactg ttgtatagct tactcatctt     2940
gctgtattaa aactttgtgc ccattgatta gtaaccctc gtttcgtcct cccccagcca     3000
ctggcaacca gcattatact ctttgattct atgagtttga ctactttagc taccttatat     3060
aagtggtatt atgtactgtt tatcttttta tgactgactt attccccttta gcatagtgca     3120 ttcaaagtcc aaccatgttg ttgcctattg cagaatttcc ttcttttcaa ggctgaataa     3180
tattccagtg catgtgtgta ccacattttc tttatccatt aatttgttga ttgatagaca     3240
```

```
tttaggttgg ttttctacat cttgactatc atgaatagtg ttgcaatgaa cacaggagag   3300
ctactatctc ttagagatga tatcatggtt tttatcatca gaaacaccc actgatttct    3360 atgctaattt tgttacctgg gtggaataat agtacagcta tatattcctc attttagata   3420
tctttgtatt tctacataca ataaaaaagc agagtactta gtcatgttga agaactttaa   3480
acttttagta tttccagatc aatcttcaaa acaaggacag gtttatcttt ctctcaccac   3540
tcaatctata tatacctctt gtgggcaagg ccagttttta tcactggagc ctttcccctt   3600
tttattatgt acctctccct cacagcagag tcaggacttt aactttacac aatactatgg   3660
ctctacatat gaaatcttaa aaatacataa aaattaataa attctgtcta gagtagtata   3720
ttttccctgg ggttacagtt actttcataa taaaaattag agataaggaa aggactcatt   3780
tattggaaag tgattttagg taacatttct ggaagaaaaa tgtctatatc ttaatagtca   3840
cttaatatat gatggattgt gttactcctc agttttcaat ggcatatact aaaacatggc   3900
cctctaaaaa gggggcaaat gaatgagaaa actctctgaa tgttttctc ccctaggtga    3960 attcacctgc tgcttagaag cttatttct cttgatttct gttataatga ttgctcttac    4020
cctttagttt taagtttcaa ataggagtc atataacttt ccttaaagct attgactgtc    4080
tttttgtcct gttttattca ccatgagtta tagtgtgaca gttaattctt atgaaaatta   4140
tatagagatg gttaaatcat cagaaactgt aaacctcgat tgggagggga agcggatttt   4200
taaatgattt cctgaccaag cttaaccagt atattaaatc ctttgtactg ttcttttggct  4260 ataaagaaaa aaggtactgt ccagcaactg aaacctgctt tcttccattt agcataccct   4320
ttttggagac aaattatgca cagttgcaac tcttcgtgaa acctatggtg aaatggctga   4380
ctgctgtgca aaacaagaac ctgagagaaa tgaatgcttc ttgcaacaca agatgacaa    4440 cccaaacctc ccccgattgg tgagaccaga ggttgatgtg atgtgcactg cttttcatga   4500
caatgaagag acattttttga aaagtaagt aatcagatgt ttatagttca aaattaaaaa   4560
gcatggagta actccatagg ccaacactct ataaaaatta ccataacaaa atattttca    4620 acattaagac ttggaagttt tgttatgatg attttttaaa gaagtagtat ttgataccac   4680
aaaattctac acagcaaaaa atatgatcaa agatattttg aagtttattg aaacaggata   4740
caatctttct gaaaaattta agatagacaa attatttaat gtattacgaa gatatgtata   4800
tatggttgtt ataattgatt tcgttttagt cagcaacatt atattgccaa aatttaacca   4860
tttatgcaca cacacacaca cacacacaca cttaaccctt ttttccacat acttaaagaa   4920
tgacagagac aagaccatca tgtgcaaatt gagcttaatt ggttaattag atatctttgg   4980
aatttggagg ttctggggag aatgtcgatt acaattattt ctgtaatatt gtctgctata   5040
gaaaagtgac tgttttttctt tttcaaaatt tagatactta tatgaaattg ccagaagaca   5100
tccttacttt tatgccccgg aactcctttt ctttgctaaa aggtataaag ctgcttttac   5160
agaatgttgc caagctgctg ataaagctgc ctgcctgttg ccaaaggtat tatgcaaaag   5220
aatagaaaaa aagagttcat tatccaacct gattttgtcc attttgtggc tagatttagg   5280
gaacctgagt gtctgataca aactttccga catggtcaaa aaagccttcc ttttatctgt   5340
cttgaaaatc tttcatcttt gaaggcctac actctcgttt cttcttttaa gatttgccaa   5400
tgatgatctg tcagaggtaa tcactgtgca tgtgtttaaa gatttcacca cttttttatgg  5460 tggtgatcac tatagtgaaa tactgaaact tgtttgtcaa attgcacagc aaggggccac   5520
agttcttgtt tatcttttca tgataatttt tagtagggag ggaattcaaa gtagagaatt   5580
```

-continued

```
ttactgcatc tagatgcctg agttcatgca ttcattccat aaatatatat tatggaatgc     5640
tttattttct tttctgagga gtttactgat gttggtggag gagagactga aatgaattat     5700
acacaaaatt taaaaattag caaaattgca gcccctggga tattagcgta ctctttctct     5760
gacttttctc ccacttttaa ggctctttt cctggcaatg tttccagttg gtttctaact     5820
acatagggaa ttccgctgtg accagaatga tcgaatgatc tttccttttc ttagagagca     5880
aaatcattat tcgctaaagg gagtacttgg gaatttaggc ataaattatg ccttcaaaat     5940
ttaatttggc acagtctcat ctgagcttat ggaggggtgt ttcatgtaga attttttcttc    6000
taattttcat caaattattc cttttttgtag ctcgatgaac ttcgggatga agggaaggct    6060
tcgtctgcca aacagagact caagtgtgcc agtctccaaa aatttggaga aagagctttc     6120
aaagcatggt aaatactttt aaacatagtt ggcatcttta taacgatgta aatgataatg     6180
cttcagtgac aaattgtaca ttttatgta ttttgcaaag tgctgtcaaa tacatttctt      6240
tggttgtcta acaggtagaa ctctaataga ggtaaaaatc agaatatcaa tgacaatttg    6300
acattatttt taatcttttc ttttctaaat agttgaataa tttagaggac gctgtccttt     6360
ttgtcctaaa aaagggaca gatatttaag ttctatttat ttataaaatc ttggactctt      6420
attctaatgg ttcattattt ttatagagct gtaggcatgg ttctttatt aattttttaa     6480
agttatttt aattttgtg gatacagagt aggtatacat atttacgggg tatatgagat      6540
attttgatat aagtatacaa catatataat cccttttattt aattttatct tcccccaat    6600
gatctaaaac tatttgcttg tccttttatg tcttatagtt aaattcagtc accaactaag    6660
ttgaagttac ttcttatttt tgcatagctc cagctctgat cttcatctca tgtttttgcc    6720
tgagcctctg ttttcatatt acttagttgg ttctgggagc atactttaat agccgagtca    6780
agaaaaatac tagctgcccc gtcacccaca ctcctcacct gctagtcaac agcaaatcaa    6840
cacaacagga aataaaatga aaataataga cattatgcat gctctctaga aactgtcaat   6900
tgaactgtat ttgctcatca ttcctaccat ctacaccacc aaaatcaacc aaatttatga    6960
aaaaaaacag ccccaacata aaattataca cagataaaca ggctatgatt ggttttggga    7020
aagaagtcac cttacctga tttaggcaac tgtgaaatga ctagagaatg aagaaaatta     7080
gacgtttaca tcttgtcata gagtttgaag atagtgctgg atctttcttt ttataagtaa    7140
gatcaataaa aactccctca ttctgtagaa gttatgattt cttttctaag agacctttag    7200
aagtcagaaa aaatgtgttt caattgagaa aaaagataac tggagtttgt gtagtacttc    7260
ccagattata aaatgctttt gtatgtatta tctaatttaa tcctcaaaac ttcttcaatt    7320
tagcatgttg tcatgacact gcagaggctg aagctcagag aggctgagcc ctctgctaac    7380
aagtcctact gctaacaagt gataaagcca gagctggaag tcacatctgg actccaaacc    7440
tgatgcttct cagcctgttg cccctttag agttcctttt taatttctgc ttttatgact     7500
tgctagattt ctacctacca cacacactct taaatggata attctgccct aaggataagt    7560
gattaccatt tggttcagaa ctagaactaa tgaattttaa aaattatttc tgtatgtcca    7620
ttttgaattt tcttatgaga aatagtattt gcctagtgtt ttcatataaa atatcgcatg    7680
ataataccat tttgattggc gattttcttt ttagggcagt agctcgcctg agccagagat    7740
ttcccaaagc tgagtttgca gaagtttcca agttagtgac agatcttacc aaagtccaca    7800
cggaatgctg ccatggagat ctgcttgaat gtgctgatga cagggtaaag agtcgtcgat    7860
atgcttttg gtagcttgca tgctcaagtt ggtagaatgg atgcgtttgg tatcattggt     7920
gatagctgac agtgggttga gattgtcttc tgtgctttcg tctgtcctat cttcaatctt    7980
```

```
tccctgccta tggtggtggt acctttctgt ttttaacctg gctataaatt accagataaa   8040
cccattcact gatttgtaac tcctttcagt catgctctaa ctgtaaatga aggcttaaac   8100
tgaagtagaa cagttacaag gttttacttg gcagaacatc ttgcaaggta gatgtctaag   8160 aagattttt tttctttttt taagacagag tttcgctctt gtttcccagg ctggggtgca   8220
atggtgtgat cttggctcag cgcaacctct gcctcctggg ttcaagtgat tctcatgcct   8280
cagcctccca agtagctggg attacaggca tgcgccacca cacctggcta attttgtatt   8340
tttagtagag gcggggtttc accatattgt ccagactggt ctcgaactcc tgacctcagg   8400
tgatccaccc gccttggcct cccaaagtgc tgggattaca ggcatgagcc accttgccca   8460
gcctaagaag attttttgag ggaggtaggt ggacttggag aaggtcacta cttgaagaga   8520
tttttggaaa tgatgtattt ttcttctcta tattccttcc cttaattaac tctgtttgtt   8580
agatgtgcaa atatttggaa tgatatctct tttctcaaaa cttataatat tttctttctc   8640
cctttcttca agattaaact tatgggcaaa tactagaatc ctaatctctc atggcacttt   8700
ctggaaaatt taaggcggtt attttatata tgtaagcagg gcctatgact atgatcttga   8760 ctcattttc aaaaatcttc tatattttat ttagttattt ggtttcaaaa ggcctgcact   8820
taatttgggg ggattatttg gaaaaacagc attgagtttt aatgaaaaaa acttaaatgc   8880
cctaacagta gaaacataaa attaataaat aactgagctg agcacctgct actgattagt   8940
ctattttaat taagtgggaa tgttttttgta gtcctatcta catctccagg tttaggagca   9000
aacagagtat gttcatagaa ggaatatgtg tatggtctta gaatacaatg aatatgttct   9060
gccaacttaa taaaggtctg aggagaaagt gtagcaatgt caattcgtgt tgaacaattt   9120
ccaccaactt acttataggc ggaccttgcc aagtatatct gtgaaaatca agattcgatc   9180
tccagtaaac tgaaggaatg ctgtgaaaaa cctctgttgg aaaaatccca ctgcattgcc   9240
gaagtggaaa atgatgagat gcctgctgac ttgccttcat tagctgctga ttttgttgaa   9300
agtaaggatg tttgcaaaaa ctatgctgag gcaaaggatg tcttcctggg catgtaagta   9360
gataagaaat tattcttta tagctttggc atgacctcac aacttaggag gatagcctag   9420
gcttttctgt ggagttgcta caatttccct gctgcccaga atgtttcttc atccttccct   9480
ttcccaggct ttaacaattt ttgaaatagt taattagttg aatacattgt cataaaataa   9540
tacatgttca tggcaaagct caacattcct tactccttag gggtatttct gaaaatacgt   9600
ctagaaacat tttgtgtata tataaattat gtatacttca gtcattcatt ccaagtgtat   9660
ttcttgaaca tctataatat atgtgtgtga ctatgtattg cctgtctatc taactaatct   9720
aatctaatct agtctatcta tctaatctat gcaatgatag caaagaagta taaaagaaa   9780 tatagagtct gacaccaggt gctttatatt tggtgaaaag accagaagtt cagtataatg   9840
gcaatatggt aggcaactca attacaaaat aaatgtttac atattgtcag aagttgtggt   9900
gataaactgc attttgttg ttggattatg ataatgcact aaataatatt tcctaaaatt   9960
atgtacccta caagatttca ctcatacaga gaagaaagag aatattttaa gaacatatct  10020
ctgcccatct atttatcaga atcctttga gatgtagttt aaatcaaaca aaatgttaat  10080
aaaaataaca agtatcattc atcaaagact tcatatgtgc caagcagtgt gtgctttgtg  10140
tagattatgt catatagttc tcataatcca ccttccgaga cagatactat ttattttttg  10200
agacagagtt ttactcttgt tgcccaggct ggagtgcaat ggtgccatct cggctcacca  10260
caacctccgc ctcccaggtt caagcgattc tcctgcctca gcctcctggg attacaggca  10320
```

```
tgcaccacca tgcctggcta attttgtatt tttagtagag atggggtttc accatgttgg   10380
tcagactggt ctcaaactcc tgacctctgg tgatatgcct gcctcagcct cctaaagtgc   10440
tgggattaca ggcatgagcc actgtgccca gccgacagat actattatta tttccattct   10500
accgagaagg agactaaggc tctgatcatt taaataagtt gcctaaggtg atgcagtgat   10560
ataagtagca gagctaggaa ttgagccttg gtaactttaa ctctggaccc caagtcctta   10620
gctactaagc tttactgcat ggggtttagt caaattaaga cttttggaat atgagttact   10680
tttgagatta gctttgtgat attttttgtg ctcatttgtc caacaaagtc tattttattt   10740
tcatcttaat taggtttttg tatgaatatg caagaaggca tcctgattac tctgtcgtgc   10800
tgctgctgag acttgccaag acatatgaaa ccactctaga gaagtgctgt gccgctgcag   10860
atcctcatga atgctatgcc aaagtggtag gtttattgtt ggaaaaaaat gtagttcttt   10920
gactgatgat tccaataatg agaaagaaaa ataatgcaag aatgtaaaat gatatacagt   10980
gcaatttaga tcttttcttg agatggtttc aattctggaa tcttaaacat gaaagaaaaa   11040
gtagccttag aatgattaac aaaatttaga ctagttagaa tagaaagatc tgaatagagc   11100
aatctctaaa aaattttgat ctttttttct cttttcaca atcctgagaa caaaaaaaa    11160
ttaaatttaa atgttaatta gaagatattt aacttagatg taaagtgagt taacctgatt   11220
ccaggattaa tcaagtacta gaattagtat cttatggcaa attatagaac ctatcccttt   11280
agaatatttt caaatctttt tgaggatgtt taggaatagt tttacaagaa attaagttag   11340
gagaggaaat ctgttctgga ggattttag ggttcccact agcatatgta atggtttctg    11400
aactattcag aatcagagaa aactcatttt tcctgctttc aagaagctac tgtatgccag   11460
gcaccatgca caaacaatga ccaacgtaaa atctctcatt ttggagagcc tggaatctaa   11520
ctggaaaggt gaactaataa taataatatg tacaatcata gccatcattt attaaacttt   11580
tattatatgc aaggcactgt ttaatttcat tagcttacct ggtttacaga gcagctctat   11640
gagatgagtg ccatctttgc ccctatttta gggataagga ttctgaaatg tggagatggt   11700
aagtaaaatt gcacaactga agaatgagtt acatgacttg gctcaaatac tggtcattga   11760
actccagagc ctgaatattc ttaaccactt acatgatgca agctcaccaa ataaatagtt   11820
cgaatgtatt gtgacagagc ggcattgata ttcatctatt catgtggctt tgagtaggaa   11880
gaagaaagga tatcattctg accagagggg tgaaaaacaa cctgcatctg atcctgaggc   11940
ataatactat taacacaatt cttttatgtt tcagttcgat gaatttaaac ctcttgtgga   12000
agagcctcag aatttaatca aacaaaattg tgagctttt gagcagcttg gagagtacaa    12060
attccagaat gcgtaagtaa ttttttattga ctgattttt ttatcaattt gtaattattt    12120
aagacttaat atatgagcca cctagcatag aacttttaag aatgaaaata cattgcatat   12180
ttctaatcac tctttgtcaa gaaagatagg agaggagaga taaaatagtt gatggggtgg   12240
agaggtctat atttgaatgt agtctaaaaa ttgttctctt aagattggaa gtatgtaggc   12300
tgggagggta aataccaaat cttggtatat cagaactgag catgtccctt gaaggttaag   12360
aaatagttaa tgggcaaata gagcatggca atattttgta gagcagcaag tagtaggcct   12420
tgaatagatg tcgctcaaaa agtaatatgt aagctgaaca caaaaatgta acaaatgaat   12480
ttagatacat atttgaatat taaattcagg ttgtttggga gatgcaccta gtctttgatg   12540
gttaaacctt tccctccata gaagagacag agacagaatg gcttgctgga ctaatgtccc   12600
aattcaatag agtcttatct atgaaggtta aaaacaagaa gagacatatt atacagtaga   12660
tatttattgt gtggctcata cacatggtgc tcttctgatt atggattta gagataataa    12720
```

```
cagtgaacaa gacatagttt ctttcctcga gtagattaaa gtcatacatt gacttttaat   12780
ggtgactggc attcttaata catgattatt atatattagg taccatgtca gattaattat   12840
aatactttac tactttttaat ttaacccttg aactatccct attgagtcag atatatttcc   12900
ttccattttc tacttgtatc tttcaagttt agcatatgct gatacatatg aagctctctc   12960
caggttttat tgaaagaaga aattaataaa tttattaatg tcactgaatt aggcaactca   13020 cttttcccaag attatgcaag tggtacaggt ggaactcaaa gccaagttta actagttgtt   13080
caggagaatg ttttctaccc tccactaacc cactactctg cagatggaga taatatgatg   13140 aatgaacat agcaacatct tagttgattc cggccaagtg ttctctgttt tatctactat   13200
gttagacagt ttcttgcctt gctgaaaaca catgacttct ttttttcagg ctattagttc   13260
gttacaccaa gaaagtaccc caagtgtcaa ctccaactct tgtagaggtc tcaagaaacc   13320
taggaaaagt gggcagcaaa tgttgtaaac atcctgaagc aaaagaatg ccctgtgcag    13380 aagactatgt gagtctttaa aaaaatataa taaattaata atgaaaaaat tttacccttta  13440 gatattgata atgctagctt tcataagcag aaggaagtaa tgtgtgtgtg tgcatgtttg   13500
tgtgcatgtg tgtgtgcatg cacgtgtgtg tatgtgtgat attggcagtc aaggccccga   13560
ggatgataat ttttttttt tttttgagac ggagtctcgc tttgttgtcc aggctggagt     13620
gcagtggtgc catctcggct cactgcaacc tccgcctccc aggttcaagc cattctcctg   13680
cctcagcctc ccaagtagct gggactacag gtgcatgcca ccatgcctgg ctaattttttt  13740 gtattttttag tagaaaattt tcagcttcac ctctttttgaa tttctgctct cctgcctgtt  13800
ctttagctat ccgtggtcct gaaccagtta tgtgtgttgc atgagaaaac gccagtaagt   13860
gacagagtca ccaaatgctg cacagaatcc ttggtgaaca ggcgaccatg cttttcagct   13920
ctggaagtcg atgaaacata cgttcccaaa gagtttaatg ctgaaacatt caccttccat   13980
gcagatatat gcacactttc tgagaaggag agacaaatca agaaacaaac gtgaggagta   14040
tttcattact gcatgtgttt gtagtcttga tagcaagaac tgtcaattca agctagcaac   14100
tttttcctga agtagtgatt atatttctta gaggaaagta ttggagtgtt gcccttatta   14160
tgctgataag agtacccaga ataaaatgaa taactttta aagacaaaat cctctgttat     14220
aatattgcta aaattattca gagtaatatt gtggattaaa gccacaatag aataacatgt   14280
taggccatat tcagtagaaa aagatgaaca attaactgat aaatttgtgc acatggcaaa   14340
ttagttaatg ggaaccatag gagaatttat ttctagatgt aaataattat tttaagtttg   14400
ccctatggtg gccccacaca tgagacaaac ccccaagatg tgacttttga gaatgagact   14460
tggataaaaa acatgtagaa atgcaagccc tgaagctcaa ctccctattg ctatcacagg   14520
ggttataatt gcataaaatt tagctataga agttgctgt catctcttgt gggctgtaat    14580
catcgtctag gcttaagagt aatattgcaa aacctgtcat gcccacacaa atctctccct   14640
ggcattgttg tctttgcaga tgtcagtgaa agagaaccag cagctcccat gagtttggat   14700
agccttattt tctatagcct ccccactatt agctttgaag ggagcaaagt ttaagaacca   14760
aatataaagt ttctcatctt tatagatgag aaaaattta aataaagtcc aagataatta    14820 aattttttaag gatcattttt agctctttaa tagcaataaa actcaatatg acataatatg  14880
gcacttccaa aatctgaata atatataatt gcaatgacat acttctttc agagatttac    14940 tgaaaagaaa tttgttgaca ctacataacg tgatgagtgg tttatactga ttgtttcagt   15000
tggtcttccc accaactcca tgaaagtgga ttttattatc ctcatcatgc agatgagaat   15060
```

```
attgagactt atagcggtat gcctgagccc caaagtactc agagttgcct ggctccaaga    15120
tttataatct taaatgatgg gactaccatc cttactctct ccattttct atacgtgagt     15180
aatgttttt  ctgttttttt ttttctttt  tccattcaaa ctcagtgcac ttgttgagct   15240
cgtgaaacac aagcccaagg caacaaaaga gcaactgaaa gctgttatgg atgatttcgc   15300
agcttttgta gagaagtgct gcaaggctga cgataaggag acctgctttg ccgaggaggt   15360
actacagttc tcttcatttt aatatgtcca gtattcattt ttgcatgttt ggttaggcta   15420
gggcttaggg atttatatat caaggaggc tttgtacatg tgggacaggg atcttatttt    15480
acaaacaatt gtcttacaaa atgaataaaa cagcactttg tttttatctc ctgctctatt   15540
gtgccatact gttaaatgtt tataatgcct gttctgtttc caaatttgtg atgcttatga   15600
atattaatag gaatatttgt aaggcctgaa atattttgat catgaaatca aacattaat    15660
ttatttaaac atttacttga aatgtggtgg tttgtgattt agttgatttt ataggctagt   15720
gggagaattt acattcaaat gtctaaatca cttaaaattg cccttttatgg cctgacagta   15780
acttttttt  attcatttgg ggacaactat gtccgtgagc ttccgtccag agattatagt   15840
agtaaattgt aattaaagga tatgatgcac gtgaaatcac tttgcaatca tcaatagctt   15900
cataaatgtt aattttgtat cctaatagta atgctaatat tttcctaaca tctgtcatgt   15960
ctttgtgttc agggtaaaaa acttgttgct gcaagtcaag ctgccttagg cttataacat   16020
cacatttaaa agcatctcag gtaactatat tttgaatttt ttaaaaagt aactataata    16080
gttattatta aaatagcaaa gattgaccat ttccaagagc catatagacc agcaccgacc   16140
actattctaa actatttatg tatgtaaata ttagctttta aaattctcaa aatagttgct   16200
gagttgggaa ccactattat ttctattttg tagatgagaa aatgaagata aacatcaaag   16260
catagattaa gtaattttcc aaagggtcaa aattcaaaat tgaaaccaaa gtttcagtgt   16320
tgcccattgt cctgttctga cttatatgat gcggtacaca gagccatcca agtaagtgat   16380
ggctcagcag tgggaatactc tgggaattag gctgaaccac atgaaagagt gctttatagg   16440
gcaaaaacag ttgaatatca gtgatttcac atggttcaac ctaatagttc aactcatcct   16500
ttccattgga gaatatgatg gatctacctt ctgtgaactt tatagtgaag aatctgctat   16560
tacatttcca atttgtcaac atgctgagct ttaataggac ttatcttctt atgacaacat   16620
ttattggtgt gtccccttgc ctagcccaac agaagaattc agcagccgta agtctaggac   16680
aggcttaaat tgttttcact ggtgtaaatt gcagaaagat gatctaagta atttggcatt   16740
tattttaata ggtttgaaaa acacatgcca tttacaaat aagacttata tttgtccttt    16800
tgtttttcag cctaccatga gaataagaga aagaaaatga agatcaaaag cttattcatc   16860
tgttttctt  tttcgttggt gtaaagccaa caccctgtct aaaaaacata aatttcttta   16920
atcattttgc ctcttttctc tgtgcttcaa ttaataaaaa atggaaagaa tctaatagag   16980
tggtacagca ctgttatttt tcaaagatgt gttgctatcc tgaaaattct gtaggttctg   17040
tggaagttcc agtgttctct cttattccac ttcggtagag gatttctagt ttcttgtggg   17100
ctaattaaat aaatcattaa tactcttcta agttatggat tataaacatt caaaataata   17160
ttttgacatt atgataattc tgaataaaag aacaaaaacc atggtatagg taggaatat    17220
aaaacatggc ttttaccta gaaaaacaa ttctaaaatt catatggaat caaaaagag      17280
cctgcagaac caaagtaaga ctaagcaaaa agaacaaatt acctgatttc aaactacact   17340
ataaggccat agtcaccgaa acagcaaggt actggtataa actcgagata acttcgtata   17400
atgtatgcta tacgaagtta tatgcatgcc agtagcagca cccacgtcca ccttctgtct   17460
```

```
agtaatgtcc aacacctccc tcagtccaaa cactgctctg catccatgtg gctcccattt   17520 ataccctgaag cacttgatgg ggcctcaatg ttttactaga gcccaccccc ctgcaactct   17580
gagaccctct ggatttgtct gtcagtgcct cactggggcg ttggataatt tcttaaaagg   17640
tcaagttccc tcagcagcat tctctgagca gtctgaagat gtgtgctttt cacagttcaa   17700
atccatgtgg ctgtttcacc cacctgcctg gccttgggtt atctatcagg acctagccta   17760
gaagcaggtg tgtggcactt aacacctaag ctgagtgact aactgaacac tcaagtggat   17820
gccatctttg tcacttcttg actgtgacac aagcaactcc tgatgccaaa gccctgccca   17880
cccctctcat gcccatattt ggacatggta caggtcctca ctggccatgg tctgtgaggt   17940
cctggtcctc tttgacttca taattcctag gggccactag tatctataag aggaagaggg   18000
tgctggctcc caggccacag cccacaaaat tccacctgct cacaggttgg ctggctcgac   18060
ccaggtggtg tcccctgctc tgagccagct cccggccaag ccagcaccat gggaaccccc   18120
aagaagaaga ggaaggtgcg taccgattta aattccaatt tactgaccgt acaccaaaat   18180
ttgcctgcat taccggtcga tgcaacgagt gatgaggttc gcaagaacct gatggacatg   18240
ttcagggatc gccaggcgtt ttctgagcat acctggaaaa tgcttctgtc cgtttgccgg   18300
tcgtgggcgg catggtgcaa gttgaataac cggaaatggt ttcccgcaga acctgaagat   18360
gttcgcgatt atcttctata tcttcaggcg cgcggtctgg cagtaaaaac tatccagcaa   18420
catttgggcc agctaaacat gcttcatcgt cggtccgggc tgccacgacc aagtgacagc   18480
aatgctgttt cactggttat gcggcggatc cgaaaagaaa acgttgatgc cggtgaacgt   18540
gcaaaacagg taaatataaa attttttaagt gtataatgat gttaaactac tgattctaat   18600
tgtttgtgta ttttaggctc tagcgttcga acgcactgat ttcgaccagg ttcgttcact   18660 catgggaaaat agcgatcgct gccaggatat acgtaatctg gcatttctgg ggattgctta   18720
taacaccctg ttacgtatag ccgaaattgc caggatcagg gttaaagata tctcacgtac   18780
tgacggtggg agaatgttaa tccatattgg cagaacgaaa acgctggtta gcaccgcagg   18840
tgtagagaag gcacttagcc tgggggtaac taaactggtc gagcgatgga tttccgtctc   18900
tggtgtagct gatgatccga ataactacct gttttgccgg gtcagaaaaa atggtgttgc   18960
cgcgccatct gccaccagcc agctatcaac tcgcgccctg gaagggattt ttgaagcaac   19020
tcatcgattg atttacggcg ctaaggatga ctctggtcag agatacctgg cctggtctgg   19080
acacagtgcc cgtgtcggag ccgcgcgaga tatgcccgc gctggagttt caataccgga   19140
gatcatgcaa gctggtggct ggaccaatgt aaatattgtc atgaactata tccgtaacct   19200
ggatagtgaa acaggggcaa tggtgcgcct gctggaagat ggcgattagg cggccggccg   19260
ctaatcagcc ataccacatt tgtagaggtt ttacttgctt taaaaaacct cccacacctc   19320
cccctgaacc tgaaacataa aatgaatgca attgttgttg ttaacttgtt tattgcagct   19380
tataatggtt acaaataaag caatagcatc acaaatttca caaataaagc atttttttca   19440
ctgcattcta gttgtggttt gtccaaactc atcaatgtat cttatcatgt ctggatcccc   19500
cggctagagt ttaaacacta gaactagtgg atccccgggg atcatggcct ccgcgccggg   19560
ttttggcgcc tcccgcgggc gcccccctcc tcacggcgag cgctgccacg tcagacgaag   19620
ggcgcagcga gcgtcctgat ccttccgccc ggacgctcag gacagcggcc cgctgctcat   19680
aagactcggc cttagaaccc cagtatcagc agaaggacat ttaggacgg acttgggtg   19740 actctagggc actggttttc tttccagaga gcggaacagg cgaggaaaag tagtcccttc   19800
```

-continued

```
tcggcgattc tgcggaggga tctccgtggg gcggtgaacg ccgatgatta tataaggacg    19860
cgccgggtgt ggcacagcta gttccgtcgc agccgggatt tgggtcgcgg ttcttgtttg    19920
tggatcgctg tgatcgtcac ttggtgagta gcgggctgct gggctggccg gggctttcgt    19980
ggccgccggg ccgctcggtg ggacggaagc gtgtggagag accgccaagg gctgtagtct    20040
gggtccgcga gcaaggttgc cctgaactgg gggttggggg gagcgcagca aaatggcggc    20100
tgttcccgag tcttgaatgg aagacgcttg tgaggcgggc tgtgaggtcg ttgaaacaag    20160
gtgggggcag tggtgggcgg caagaaccca aggtcttgag gccttcgcta atgcgggaaa    20220
gctcttattc gggtgagatg ggctggggca ccatctgggg accctgacgt gaagtttgtc    20280
actgactgga gaactcggtt tgtcgtctgt tgcgggggcg gcagttatgg cggtgccgtt    20340
gggcagtgca cccgtacctt tgggagcgcg cgccctcgtc gtgtcgtgac gtcacccgtt    20400
ctgttggctt ataatgcagg gtggggccac ctgccggtag gtgtgcggta ggcttttctc    20460
cgtcgcagga cgcagggttc gggcctaggg taggctctcc tgaatcgaca ggcgccggac    20520
ctctggtgag gggagggata agtgaggcgt cagtttcttt ggtcggtttt atgtacctat    20580
cttcttaagt agctgaagct ccggttttga actatgcgct cggggttggc gagtgtgttt    20640
tgtgaagttt ttaggcacc ttttgaaatg taatcatttg ggtcaatatg taattttcag    20700
tgttagacta gtaaattgtc cgctaaattc tggccgtttt tggctttttt gttagacgtg    20760
ttgacaatta atcatcggca tagtatatcg gcatagtata atacgacaag gtgaggaact    20820
aaaccatggg atcggccatt gaacaagatg gattgcacgc aggttctccg gccgcttggg    20880
tggagaggct attcggctat gactgggcac aacagacaat cggctgctct gatgccgccg    20940
tgttccggct gtcagcgcag gggcgcccgg ttcttttgt caagaccgac ctgtccggtg    21000
ccctgaatga actgcaggac gaggcagcgc ggctatcgtg gctggccacg acgggcgttc    21060
cttgcgcagc tgtgctcgac gttgtcactg aagcgggaag ggactggctg ctattgggcg    21120
aagtgccggg gcaggatctc ctgtcatctc accttgctcc tgccgagaaa gtatccatca    21180
tggctgatgc aatgcggcgg ctgcatacgc ttgatccggc tacctgccca ttcgaccacc    21240
aagcgaaaca tcgcatcgag cgagcacgta ctcggatgga agccggtctt gtcgatcagg    21300
atgatctgga cgaagagcat caggggctcg cgccagccga actgttcgcc aggctcaagg    21360
cgcgcatgcc cgacggcgat gatctcgtcg tgacccatgg cgatgcctgc ttgccgaata    21420
tcatggtgga aaatggccgc ttttctggat tcatcgactg tggccggctg ggtgtggcgg    21480
accgctatca ggacatagcg ttggctaccc gtgatattgc tgaagagctt ggcggcgaat    21540
gggctgaccg cttcctcgtg ctttacggta tcgccgctcc cgattcgcag cgcatcgcct    21600
tctatcgcct tcttgacgag ttcttctgag gggatccgct gtaagtctgc agaaattgat    21660
gatctattaa acaataaaga tgtccactaa aatggaagtt tttcctgtca ctttgttta    21720 agaagggtga gaacagagta cctacatttt gaatggaagg attggagcta cggggtgggg    21780
ggtggggtgg gattagataa atgcctgctc tttactgaag gctctttact attgctttat    21840
gataatgttt catagttgga tatcataatt taaacaagca aaaccaaatt aagggccagc    21900
tcattcctcc cactcatgat ctatagatct atagatctct cgtgggatca ttgttttct    21960 cttgattccc actttgtggt tctaagtact gtggtttcca aatgtgtcag tttcatagcc    22020
tgaagaacga gatcagcagc ctctgttcca catacacttc attctcagta ttgttttgcc    22080
aagttctaat tccatcagac ctcgacctgc agccccctaga taacttcgta taatgtatgc    22140
tatacgaagt tatgctaggt aactataacg gtcctaaggt agcgagctag cacacatcac    22200
```

```
aaccacaacc ttctcaggta actatacttg ggacttaaaa aacataatca taatcatttt    22260
tcctaaaacg atcaagactg ataaccattt gacaagagcc atacagacaa gcaccagctg    22320
gcactcttag gtcttcacgt atggtcatca gtttgggttc catttgtaga taagaaactg    22380
aacatataaa ggtctaggtt aatgcaattt acacaaaagg agaccaaacc agggagagaa    22440
ggaaccaaaa ttaaaaattc aaaccagagc aaaggagtta gccctggttt tgctctgact    22500
tacatgaacc actatgtgga gtcctccatg ttagcctagt caagcttatc ctctggatga    22560
agttgaaacc atatgaagga atatttgggg ggtgggtcaa aacagttgtg tatcaatgat    22620
tccatgtggt ttgacccaat cattctgtga atccatttca acagaagata caacgggttc    22680
tgtttcataa taagtgatcc acttccaaat ttctgatgtg ccccatgcta agctttaaca    22740
gaatttatct tcttatgaca aagcagcctc ctttgaaaat atagccaact gcacacagct    22800
atgttgatca attttgttta taatcttgca gaagagaatt ttttaaaata gggcaataat    22860
ggaaggcttt ggcaaaaaaa ttgtttctcc atatgaaaac aaaaaaactta tttttttatt    22920 caagcaaaga acctatagac ataaggctat ttcaaaatta tttcagttttt agaaagaatt    22980 gaaagttttg tagcattctg agaagacagc tttcatttgt aatcataggt aatatgtagg    23040
tcctcagaaa tggtgagacc cctgactttg acacttgggg actctgaggg accagtgatg    23100
aagagggcac aacttatatc acacatgcac gagttggggt gagagggtgt cacaacatct    23160
atcagtgtgt catctgccca ccaagtaaca gatgtcagct aagactaggt catgtgtagg    23220
ctgtctacac cagtgaaaat cgcaaaaaga atctaagaaa ttccacattt ctagaaaata    23280
ggtttggaaa ccgtattcca ttttacaaag gacacttaca tttctctttt tgttttccag    23340
gctaccctga gaaaaaaaga catgaagact caggactcat ctttctgtt ggtgtaaaat    23400 caacacccta aggaacacaa atttctttaa acatttgact tcttgtctct gtgctgcaat    23460
taataaaaaa tggaaagaat ctac                                           23484
```

<210> SEQ ID NO 18
<211> LENGTH: 17768
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(46)
<223> OTHER INFORMATION: Mouse Sequence
<220> FEATURE:
<221> NAME/KEY: misc_feature
<222> LOCATION: (47)..(17381)
<223> OTHER INFORMATION: Human Sequence
<220> FEATURE:
<221> NAME/KEY: misc_feature
<222> LOCATION: (17382)..(17387)
<223> OTHER INFORMATION: XhoI
<220> FEATURE:
<221> NAME/KEY: misc_feature
<222> LOCATION: (17388)..(17421)
<223> OTHER INFORMATION: LoxP
<220> FEATURE:
<221> NAME/KEY: misc_feature
<222> LOCATION: (17428)..(17453)
<223> OTHER INFORMATION: I-CeuI
<220> FEATURE:
<221> NAME/KEY: misc_feature
<222> LOCATION: (17454)..(17459)
<223> OTHER INFORMATION: NheI
<220> FEATURE:
<221> NAME/KEY: misc_feature
<222> LOCATION: (17460)..(17768)

<223> OTHER INFORMATION: Mouse Sequence

<400> SEQUENCE: 18

```
tgcacacaga tcacctttcc tatcaacccc actagcctct ggcaaaatga agtgggtaac      60
ctttatttcc cttctttttc tctttagctc ggcttattcc aggggtgtgt ttcgtcgaga     120
tgcacgtaag aaatccattt ttctattgtt caacttttat tctattttcc cagtaaaata     180
aagttttagt aaactctgca tctttaaaga attattttgg catttatttc taaaatggca     240
tagtattttg tatttgtgaa gtcttacaag gttatcttat taataaaatt caaacatcct     300
aggtaaaaaa aaaaaaaggt cagaattgtt tagtgactgt aattttcttt tgcgcactaa     360
ggaaagtgca aagtaactta gagtgactga aacttcacag aataggggttg aagattgaat    420
tcataactat cccaaagacc tatccattgc actatgcttt atttaaaaac cacaaaacct     480
gtgctgttga tctcataaat agaacttgta tttatattta ttttcatttt agtctgtctt     540
cttggttgct gttgatagac actaaaagag tattagatat tatctaagtt tgaatataag     600
gctataaata tttaataatt tttaaaatag tattcttggt aattgaatta ttcttctgtt     660
taaaggcaga agaaataatt gaacatcatc ctgagttttt ctgtaggaat cagagcccaa     720
tattttgaaa caaatgcata atctaagtca aatggaaaga aatataaaaa gtaacattat     780
tacttcttgt tttcttcagt atttaacaat cctttttttt cttcccttgc ccagacaaga     840
gtgaggttgc tcatcggttt aaagatttgg gagaagaaaa tttcaaagcc ttgtaagtta     900
aaatattgat gaatcaaatt taatgtttct aatagtgttg tttattattc taaagtgctt     960
atatttcctt gtcatcaggg ttcagattct aaaacagtgc tgcctcgtag agttttctgc    1020
gttgaggaag atattctgta tctgggctat ccataaggt agtcactggt cacatggcta     1080
ttgagtactt caaatatgac aagtgcaact gagaaacaaa aacttaaatt gtatttaatt    1140
gtagttaatt tgaatgtata tagtcacatg tggctaatgg ctactgtatt ggacagtaca    1200
gctctggaac ttgcttggtg gaaaggactt taatataggt ttcctttggt ggcttaccca    1260
ctaaatcttc tttacatagc aagcattcct gtgcttagtt gggaatattt aattttttt    1320
tttttttaag acagggtctc gctctgtcgc ccaggctgga gtgcagtggc gcaatctcgg    1380
ctcactgcaa actccgcctc ccgggttcac gccattctcc tgcctcagcc tcccgagtag    1440
ctgggactac aggcgcccgc catcacgccc ggctaatctt ttgtattttt agtagagatg    1500
gggtttcacc gtgtgccagg atggtctcaa tctcctgaca tcgtgatctg cccacctcgg    1560
cctcccaaag tgctgggatt acaggagtga gccaccgcgc ccggcctatt taaatgtttt    1620
ttaatctagt aaaaaatgag aaaattgttt ttttaaaagt ctacctaatc ctacaggcta    1680
attaaagacg tgtgtgggga tcaggtgcgg tggttcacac ctgtaatccc agcactttgg    1740
aaggctgatg caggaggatt gcttgagccc aggagttcaa gaccagcctg gcaagtctc     1800
tttaaaaaaa acaaaacaaa caaacaaaaa aattaggcat ggtggcacat gcctgtagtc    1860
ctagctactt aggaggctga cgtaggagga tcgtttggac ctgagaggtc aaggctacag    1920
tgagccatga ttgtgccact gcactccagc ctgggtgaca gagtgagact ctgtctcaaa    1980
aaagaaaaag gaaatctgtg gggtttgttt tagttttaag taattctaag gactttaaaa    2040
atgcctagtc ttgacaatta gatctatttg gcatacaatt tgcttgctta atctatgtgt    2100
gtgcatagat ctactgacac acgcatacat ataaacatta gggaactacc attctctttg    2160
cgtaggaagc cacatatgcc tatctaggcc tcagatcata cctgatatga ataggctttc    2220
tggataatgg tgaagaagat gtataaaaga tagaacctat acccatacat gatttgttct    2280
```

```
ctagcgtagc aacctgttac atattaaagt tttattatac tacatttttc tacatccttt    2340
gtttcagggt gttgattgcc tttgctcagt atcttcagca gtgtccattt gaagatcatg    2400
taaaattagt gaatgaagta actgaatttg caaaaacatg tgttgctgat gagtcagctg    2460
aaaattgtga caaatcactt gtaagtacat tctaattgtg gagattcttt cttctgtttg    2520
aagtaatccc aagcatttca aaggaatttt ttttaagttt tctcaattat tattaagtgt    2580
cctgatttgt aagaaacact aaaaagttgc tcatagactg ataagccatt gtttcttttg    2640
tgatagagat gctttagcta tgtccacagt tttaaaatca tttctttatt gagaccaaac    2700
acaacagtca tggtgtattt aaatggcaat tgtcattta  taaacacctc ttttttaaaat    2760 ttgaggtttg gtttcttttt gtagaggcta atagggatat gatagcatgt atttatttat    2820
ttatttatct tattttatta tagtaagaac ccttaacatg agatctaccc tgttatattt    2880
ttaagtgtac aatccattat tgttaactac gggtacactg ttgtatagct tactcatctt    2940
gctgtattaa aactttgtgc ccattgatta gtaaccccctc gtttcgtcct cccccagcca    3000
ctggcaacca gcattatact ctttgattct atgagtttga ctactttagc tacctatat    3060 aagtggtatt atgtactgtt tatctttta tgactgactt atttccctta gcatagtgca    3120
ttcaaagtcc aaccatgttg ttgcctattg cagaatttcc ttcttttcaa ggctgaataa    3180
tattccagtg catgtgtgta ccacattttc tttatccatt aatttgttga ttgatagaca    3240
tttaggttgg ttttctacat cttgactatc atgaatagtg ttgcaatgaa cacaggagag    3300
ctactatctc ttagagatga tatcatggtt tttatcatca gaaaacaccc actgatttct    3360
atgctaattt tgttacctgg gtggaataat agtacagcta tatattcctc attttagata    3420
tctttgtatt tctacataca ataaaaaagc agagtactta gtcatgttga agaacttaa     3480 acttttagta tttccagatc aatcttcaaa acaaggacag gtttatctt ctctcaccac     3540 tcaatctata tatacctctt gtgggcaagg ccagttttta tcactggagc ctttccctt    3600 tttattatgt acctctccct cacagcagag tcaggacttt aactttacac aatactatgg    3660
ctctacatat gaaatcttaa aaatacataa aaattaataa attctgtcta gagtagtata    3720
ttttccctgg ggttacagtt actttcataa taaaaattag agataaggaa aggactcatt    3780
tattggaaag tgattttagg taacatttct ggaagaaaaa tgtctatatc ttaatagtca    3840
cttaatatat gatggattgt gttactcctc agttttcaat ggcatatact aaaacatggc    3900
cctctaaaaa gggggcaaat gaaatgagaa actctctgaa tgttttttctc ccctaggtga    3960 attcacctgc tgcttagaag cttatttct  cttgatttct gttataatga ttgctcttac    4020
cctttagttt taagtttcaa ataggagtc atataacttt ccttaaagct attgactgtc    4080
tttttgtcct gttttattca ccatgagtta tagtgtgaca gttaattctt atgaaaatta    4140
tatagagatg gttaaatcat cagaaactgt aaacctcgat tgggagggga agcggatttt    4200
taaatgattt cctgaccaag cttaaccagt atattaaatc ctttgtactg ttctttggct    4260
ataagaaaaa aaggtactgt ccagcaactg aaacctgctt tcttccattt agcataccct    4320
ttttggagac aaattatgca cagttgcaac tcttcgtgaa acctatggtg aaatggctga    4380
ctgctgtgca aaacaagaac ctgagagaaa tgaatgcttc ttgcaacaca agatgacaa    4440 cccaaacctc ccccgattgg tgagaccaga ggttgatgtg atgtgcactg cttttcatga    4500
caatgaagag acattttga aaaagtaagt aatcagatgt ttatagttca aaattaaaaa    4560
gcatggagta actccatagg ccaacactct ataaaaatta ccataacaaa aatattttca    4620
```

```
acattaagac ttggaagttt tgttatgatg attttttaaa gaagtagtat ttgataccac    4680
aaaattctac acagcaaaaa atatgatcaa agatattttg aagtttattg aaacaggata    4740
caatctttct gaaaaattta agatagacaa attatttaat gtattacgaa gatatgtata    4800
tatggttgtt ataattgatt tcgttttagt cagcaacatt atattgccaa aatttaacca    4860
tttatgcaca cacacacaca cacacacaca cttaacccct ttttccacat acttaaagaa    4920
tgacagagac aagaccatca tgtgcaaatt gagcttaatt ggttaattag atatctttgg    4980
aatttggagg ttctggggag aatgtcgatt acaattattt ctgtaatatt gtctgctata    5040
gaaaagtgac tgttttctt tttcaaaatt tagatactta tatgaaattg ccagaagaca    5100
tccttacttt tatgccccgg aactccttt ctttgctaaa aggtataaag ctgcttttac    5160
agaatgttgc caagctgctg ataaagctgc ctgcctgttg ccaaaggtat tatgcaaaag    5220
aatagaaaaa aagagttcat tatccaacct gattttgtcc attttgtggc tagatttagg    5280
gaacctgagt gtctgataca aactttccga catggtcaaa aaagccttcc ttttatctgt    5340
cttgaaaatc tttcatcttt gaaggcctac actctcgttt cttctttaa gatttgccaa    5400 tgatgatctg tcagaggtaa tcactgtgca tgtgtttaaa gatttcacca cttttatgg    5460 tggtgatcac tatagtgaaa tactgaaact tgtttgtcaa attgcacagc aaggggccac    5520
agttcttgtt tatcttttca tgataatttt tagtagggag ggaattcaaa gtagagaatt    5580
ttactgcatc tagatgcctg agttcatgca ttcattccat aaatatatat tatggaatgc    5640
tttattttct tttctgagga gtttactgat gttggtggag gagagactga aatgaattat    5700
acacaaaatt taaaaattag caaaattgca gccctggga tattagcgta ctcttttctct    5760 gacttttctc ccacttttaa ggctcttttt cctggcaatg tttccagttg gtttctaact    5820
acatagggaa ttccgctgtg accagaatga tcgaatgatc tttcctttc ttagagagca    5880 aaatcattat tcgctaaagg gagtacttgg gaatttaggc ataaattatg ccttcaaaat    5940
ttaatttggc acagtctcat ctgagcttat ggagggtgt ttcatgtaga attttttcttc    6000 taattttcat caaattattc cttttttgtag ctcgatgaac ttcgggatga agggaaggct    6060
tcgtctgcca aacagagact caagtgtgcc agtctccaaa aatttggaga aagagctttc    6120
aaagcatggt aaatactttt aaacatagtt ggcatcttta taacgatgta aatgataatg    6180
cttcagtgac aaattgtaca ttttatgta ttttgcaaag tgctgtcaaa tacatttctt    6240
tggttgtcta acaggtagaa ctctaataga ggtaaaaatc agaatatcaa tgacaatttg    6300
acattatttt taatcttttc tttctaaat agttgaataa tttagaggac gctgtccttt    6360
ttgtcctaaa aaaagggaca gatatttaag ttctatttat ttataaaatc ttggactctt    6420
attctaatgg ttcattattt ttatagagct gtaggcatgg ttctttattt aattttttaa    6480
agttattttt aattttgtg gatacagagt aggtatacat atttacgggg tatatgagat    6540
attttgatat aagtatacaa catatataat cccttattt aattttatct tccccccaat    6600
gatctaaaac tatttgcttg tccttttatg tcttatagtt aaattcagtc accaactaag    6660
ttgaagttac ttcttatttt tgcatagctc cagctctgat cttcatctca tgttttgcc    6720 tgagcctctg ttttcatatt acttagttgg ttctgggagc atactttaat agccgagtca    6780
agaaaaatac tagctgcccc gtcacccaca ctcctcacct gctagtcaac agcaaatcaa    6840
cacaacagga aataaaatga aaataataga cattatgcat gctctctaga aactgtcaat    6900
tgaactgtat ttgctcatca ttcctaccat ctacaccacc aaaatcaacc aaatttatga    6960
aaaaaaacag ccccaacata aaattataca cagataaaca ggctatgatt ggttttggga    7020
```

```
aagaagtcac ctttacctga tttaggcaac tgtgaaatga ctagagaatg aagaaaatta    7080
gacgtttaca tcttgtcata gagtttgaag atagtgctgg atctttcttt ttataagtaa    7140
gatcaataaa aactccctca ttctgtagaa gttatgattt cttttctaag agacctttag    7200
aagtcagaaa aaatgtgttt caattgagaa aaaagataac tggagtttgt gtagtacttc    7260
ccagattata aaatgctttt gtatgtatta tctaatttaa tcctcaaaac ttcttcaatt    7320
tagcatgttg tcatgacact gcagaggctg aagctcagag aggctgagcc ctctgctaac    7380
aagtcctact gctaacaagt gataaagcca gagctggaag tcacatctgg actccaaacc    7440
tgatgcttct cagcctgttg ccccttttag agttcctttt taatttctgc ttttatgact    7500
tgctagattt ctacctacca cacacactct aaatggata  attctgccct aaggataagt    7560
gattaccatt tggttcagaa ctagaactaa tgaattttaa aaattatttc tgtatgtcca    7620
ttttgaattt tcttatgaga aatagtattt gcctagtgtt ttcatataaa atatcgcatg    7680
ataataccat tttgattggc gattttcttt ttagggcagt agctcgcctg agccagagat    7740
ttcccaaagc tgagtttgca gaagtttcca agttagtgac agatcttacc aaagtccaca    7800
cggaatgctg ccatggagat ctgcttgaat gtgctgatga cagggtaaag agtcgtcgat    7860 atgcttttg  gtagcttgca tgctcaagtt ggtagaatgg atgcgtttgg tatcattggt    7920
gatagctgac agtgggttga gattgtcttc tgtgctttcg tctgtcctat cttcaatctt    7980
tccctgccta tggtggtggt acctttctgt ttttaacctg gctataaatt accagataaa    8040
cccattcact gatttgtaac tcctttcagt catgctctaa ctgtaaatga aggcttaaac    8100
tgaagtagaa cagttacaag gttttacttg gcagaacatc ttgcaaggta gatgtctaag    8160 aagattttt  tttctttttt taagacagag tttcgctctt gtttcccagg ctggggtgca    8220
atggtgtgat cttggctcag cgcaacctct gcctcctggg ttcaagtgat tctcatgcct    8280
cagcctccca gtagctggga ttacaggca  tgcgccacca cacctggcta attttgtatt    8340
tttagtagag gcggggtttc accatattgt ccagactggt ctcgaactcc tgacctcagg    8400
tgatccaccc gccttggcct cccaaagtgc tgggattaca ggcatgagcc accttgccca    8460
gcctaagaag attttttgag ggaggtaggt ggacttggag aaggtcacta cttgaagaga    8520 ttttggaaa  tgatgtattt ttcttctcta tattccttcc cttaattaac tctgtttgtt    8580
agatgtgcaa atatttggaa tgatatctct tttctcaaaa cttataatat tttctttctc    8640
cctttcttca agattaaact tatgggcaaa tactagaatc ctaatctctc atggcacttt    8700
ctggaaaatt taaggcggtt attttatata tgtaagcagg gcctatgact atgatcttga    8760 ctcattttc  aaaaatcttc tatattttat ttagttattt ggtttcaaaa ggcctgcact    8820
taattttggg ggattatttg gaaaaacagc attgagtttt aatgaaaaaa acttaaatgc    8880
cctaacagta gaaacataaa attaataaat aactgagctg agcacctgct actgattagt    8940
ctattttaat taagtgggaa tgtttttgta gtcctatcta catctccagg tttaggagca    9000
aacagagtat gttcatagaa ggaatatgtg tatggtctta gaatacaatg aatatgttct    9060
gccaacttaa taaggtctg  aggagaaagt gtagcaatgt caattcgtgt tgaacaattt    9120
ccaccaactt acttataggc ggaccttgcc aagtatatct gtgaaaatca agattcgatc    9180
tccagtaaac tgaaggaatg ctgtgaaaaa cctctgttgg aaaaatccca ctgcattgcc    9240
gaagtggaaa atgatgagat gcctgctgac ttgccttcat tagctgctga ttttgttgaa    9300
agtaaggatg tttgcaaaaa ctatgctgag gcaaaggatg tcttcctggg catgtaagta    9360
```

```
gataagaaat tattctttta tagctttggc atgacctcac aacttaggag gatagcctag    9420
gcttttctgt ggagttgcta caatttccct gctgcccaga atgtttcttc atccttccct    9480
ttcccaggct ttaacaattt ttgaaatagt taattagttg aatacattgt cataaaataa    9540
tacatgttca tggcaaagct caacattcct tactccttag gggtatttct gaaaatacgt    9600
ctagaaacat tttgtgtata tataaattat gtatacttca gtcattcatt ccaagtgtat    9660
ttcttgaaca tctataatat atgtgtgtga ctatgtattg cctgtctatc taactaatct    9720
aatctaatct agtctatcta tctaatctat gcaatgatag caaagaagta taaaaagaaa    9780
tatagagtct gacaccaggt gctttatatt tggtgaaaag accagaagtt cagtataatg    9840
gcaatatggt aggcaactca attacaaaat aaatgtttac atattgtcag aagttgtggt    9900
gataaactgc attttgttg ttggattatg ataatgcact aaataatatt tcctaaaatt      9960
atgtacccta caagatttca ctcatacaga gaagaaagag aatatttaa gaacatatct      10020 ctgcccatct atttatcaga atccttttga gatgtagttt aaatcaaaca aaatgttaat     10080
aaaaataaca agtatcattc atcaaagact tcatatgtgc caagcagtgt gtgctttgtg    10140
tagattatgt catatagttc tcataatcca ccttccgaga cagatactat ttattttttg    10200
agacagagtt ttactcttgt tgcccaggct ggagtgcaat ggtgccatct cggctcacca    10260
caacctccgc ctcccaggtt caagcgattc tcctgcctca gcctcctggg attacaggca    10320
tgcaccacca tgcctggcta attttgtatt tttagtagag atggggtttc accatgttgg    10380
tcagactggt ctcaaactcc tgacctctgg tgatatgcct gcctcagcct cctaaagtgc    10440
tgggattaca ggcatgagcc actgtgccca gccgacagat actattatta tttccattct    10500
accgagaagg agactaaggc tctgatcatt taaataagtt gcctaaggtg atgcagtgat    10560
ataagtagca gagctaggaa ttgagccttg gtaactttaa ctctggaccc caagtcctta    10620
gctactaagc tttactgcat ggggtttagt caaattaaga cttttggaat atgagttact    10680
tttgagatta gctttgtgat attttttgtg ctcatttgtc caacaaagtc tatttattt    10740 tcatcttaat taggttttg tatgaatatg caagaaggca tcctgattac tctgtcgtgc     10800
tgctgctgag acttgccaag acatatgaaa ccactctaga gaagtgctgt gccgctgcag    10860
atcctcatga atgctatgcc aaagtggtag gtttattgtt ggaaaaaaat gtagttcttt    10920
gactgatgat tccaataatg agaaagaaaa ataatgcaag aatgtaaaat gatatacagt    10980
gcaatttaga tcttttcttg agatggtttc aattctggaa tcttaaacat gaaagaaaaa    11040
gtagccttag aatgattaac aaaatttaga ctagttagaa tagaaagatc tgaatagagc    11100
aatctctaaa aaatttgat cttttttttct ctttttcaca atcctgagaa caaaaaaaaa     11160
ttaaatttaa atgttaatta gaagatattt aacttagatg taaagtgagt taacctgatt    11220
ccaggattaa tcaagtacta gaattagtat cttatggcaa attatagaac ctatccettt    11280 agaatatttt caaatctttt tgaggatgtt taggaatagt tttacaagaa attaagttag    11340
gagaggaaat ctgttctgga ggatttttag ggttcccact agcatatgta atggtttctg    11400
aactattcag aatcagagaa aactcatttt tcctgctttc aagaagctac tgtatgccag    11460
gcaccatgca caaacaatga ccaacgtaaa atctctcatt ttggagagcc tggaatctaa    11520
ctggaaaggt gaactaataa taataatatg tacaatcata gccatcattt attaaacttt    11580
tattatatgc aaggcactgt ttaatttcat tagcttacct ggtttacaga gcagctctat    11640
gagatgagtg ccatctttgc ccctatttta gggataagga ttctgaaatg tggagatggt    11700
aagtaaaatt gcacaactga agaatgagtt acatgacttg gctcaaatac tggtcattga    11760
```

```
actccagagc ctgaatattc ttaaccactt acatgatgca agctcaccaa ataaatagtt   11820
cgaatgtatt gtgacagagc ggcattgata ttcatctatt catgtggctt tgagtaggaa   11880
gaagaaagga tatcattctg accagagggg tgaaaaacaa cctgcatctg atcctgaggc   11940
ataatactat taacacaatt cttttatgtt tcagttcgat gaatttaaac ctcttgtgga   12000
agagcctcag aatttaatca aacaaaattg tgagcttttt gagcagcttg gagagtacaa   12060
attccagaat gcgtaagtaa ttttattga ctgatttttt ttatcaattt gtaattattt   12120
aagacttaat atatgagcca cctagcatag aacttttaag aatgaaaata cattgcatat   12180
ttctaatcac tctttgtcaa gaaagatagg agaggagaga taaaatagtt gatggggtgg   12240
agaggtctat atttgaatgt agtctaaaaa ttgttctctt aagattggaa gtatgtaggc   12300
tgggagggta aataccaaat cttggtatat cagaactgag catgtccctt gaaggttaag   12360
aaatagttaa tgggcaaata gagcatggca atattttgta gagcagcaag tagtaggcct   12420
tgaatagatg tcgctcaaaa agtaatatgt aagctgaaca caaaaatgta acaaatgaat   12480
ttagatacat atttgaatat taaattcagg ttgtttggga gatgcaccta gtctttgatg   12540
gttaaacctt tccctccata gaagagacag agacagaatg gcttgctgga ctaatgtccc   12600
aattcaatag agtcttatct atgaaggtta aaaacaagaa gagacatatt atacagtaga   12660
tatttattgt gtggctcata cacatggtgc tcttctgatt atggatttta gagataataa   12720
cagtgaacaa gacatagttt cttttcctcga gtagattaaa gtcatacatt gacttttaat   12780
ggtgactggc attcttaata catgattatt atatattagg taccatgtca gattaattat   12840
aatactttac tacttttaat ttaacccttg aactatccct attgagtcag atatatttcc   12900
ttccattttc tacttgtatc tttcaagttt agcatatgct gatacatatg aagctctctc   12960
caggttttat tgaaagaaga aattaataaa tttattaatg tcactgaatt aggcaactca   13020
ctttcccaag attatgcaag tggtacaggt ggaactcaaa gccaagttta actagttgtt   13080
caggagaatg ttttctaccc tccactaacc cactactctg cagatggaga taatatgatg   13140
aatgaaacat agcaacatct tagttgattc cggccaagtg ttctctgttt tatctactat   13200
gttagacagt ttcttgcctt gctgaaaaca catgacttct ttttttcagg ctattagttc   13260
gttacaccaa gaaagtaccc caagtgtcaa ctccaactct tgtagaggtc tcaagaaacc   13320
taggaaaagt gggcagcaaa tgttgtaaac atcctgaagc aaaagaatg ccctgtgcag   13380 aagactatgt gagtctttaa aaaaatataa taaattaata atgaaaaaat tttacctttta   13440 gatattgata atgctagctt tcataagcag aaggaagtaa tgtgtgtgtg tgcatgtttg   13500
tgtgcatgtg tgtgtgcatg cacgtgtgtg tatgtgtgat attggcagtc aaggccccga   13560
ggatgataat tttttttttt ttttgagac ggagtctcgc tttgttgtcc aggctggagt   13620
gcagtggtgc catctcggct cactgcaacc tccgcctccc aggttcaagc cattctcctg   13680
cctcagcctc ccaagtagct gggactacag gtgcatgcca ccatgcctgg ctaatttttt   13740
gtatttttag tagaaaattt tcagcttcac ctcttttgaa tttctgctct cctgcctgtt   13800
ctttagctat ccgtggtcct gaaccagtta tgtgtgttgc atgagaaaac gccagtaagt   13860
gacagagtca ccaaatgctg cacagaatcc ttggtgaaca ggcgaccatg cttttcagct   13920
ctggaagtcg atgaaacata cgttcccaaa gagtttaatg ctgaaacatt caccttccat   13980
gcagatatat gcacactttc tgagaaggag agacaaatca agaaacaaac gtgaggagta   14040
tttcattact gcatgtgttt gtagtcttga tagcaagaac tgtcaattca agctagcaac   14100
```

```
ttttcctga agtagtgatt atatttctta gaggaaagta ttggagtgtt gcccttatta    14160
tgctgataag agtacccaga ataaaatgaa taacttttta aagacaaaat cctctgttat    14220
aatattgcta aaattattca gagtaatatt gtggattaaa gccacaatag aataacatgt    14280
taggccatat tcagtagaaa aagatgaaca attaactgat aaatttgtgc acatggcaaa    14340
ttagttaatg ggaaccatag gagaatttat ttctagatgt aaataattat tttaagtttg    14400
ccctatggtg gccccacaca tgagacaaac ccccaagatg tgacttttga gaatgagact    14460
tggataaaaa acatgtagaa atgcaagccc tgaagctcaa ctccctattg ctatcacagg    14520
ggttataatt gcataaaatt tagctataga aagttgctgt catctcttgt gggctgtaat    14580
catcgtctag gcttaagagt aatattgcaa aacctgtcat gcccacacaa atctctccct    14640
ggcattgttg tctttgcaga tgtcagtgaa agagaaccag cagctcccat gagtttggat    14700
agccttattt tctatagcct ccccactatt agctttgaag ggagcaaagt ttaagaacca    14760
aatataaagt ttctcatctt tatagatgag aaaaatttta ataaagtcc aagataatta    14820 aattttttaag gatcattttt agctctttaa tagcaataaa actcaatatg acataatatg    14880
gcacttccaa aatctgaata atatataatt gcaatgacat acttcttttc agagatttac    14940 tgaaagaaa tttgttgaca ctacataacg tgatgagtgg tttatactga ttgtttcagt    15000
tggtcttccc accaactcca tgaaagtgga ttttattatc ctcatcatgc agatgagaat    15060
attgagactt atagcggtat gcctgagccc caaagtactc agagttgcct ggctccaaga    15120
tttataatct taaatgatgg gactaccatc cttactctct ccatttttct atacgtgagt    15180
aatgtttttt ctgttttttt ttttctttt tccattcaaa ctcagtgcac ttgttgagct    15240
cgtgaaacac aagcccaagg caacaaaga gcaactgaaa gctgttatgg atgatttcgc    15300
agcttttgta gagaagtgct gcaaggctga cgataaggag acctgctttg ccgaggaggt    15360
actacagttc tcttcatttt aatatgtcca gtattcattt ttgcatgttt ggttaggcta    15420
gggcttaggg atttatatat caaaggaggc tttgtacatg tgggacaggg atcttatttt    15480
acaaacaatt gtcttacaaa atgaataaaa cagcactttg ttttatctc ctgctctatt    15540 gtgccatact gttaaatgtt tataatgcct gttctgtttc caaatttgtg atgcttatga    15600
atattaatag gaatatttgt aaggcctgaa atattttgat catgaaatca aaacattaat    15660
ttatttaaac atttacttga aatgtggtgg tttgtgattt agttgatttt ataggctagt    15720
gggagaattt acattcaaat gtctaaatca cttaaaattg ccctttatgg cctgacagta    15780
actttttttt attcatttgg ggacaactat gtccgtgagc ttccgtccag agattatagt    15840
agtaaattgt aattaaagga tatgatgcac gtgaaatcac tttgcaatca tcaatagctt    15900
cataaatgtt aattttgtat cctaatagta atgctaatat tttcctaaca tctgtcatgt    15960
ctttgtgttc agggtaaaaa acttgttgct gcaagtcaag ctgccttagg cttataacat    16020
cacatttaaa agcatctcag gtaactatat tttgaatttt ttaaaaagt aactataata    16080 gttattatta aaatagcaaa gattgaccat ttccaagagc catatagacc agcaccgacc    16140
actattctaa actatttatg tatgtaaata ttagctttta aaattctcaa aatagttgct    16200
gagttgggaa ccactattat ttctattttg tagatgagaa aatgaagata acatcaaag    16260 catagattaa gtaattttcc aaagggtcaa aattcaaaat tgaaaccaaa gtttcagtgt    16320
tgcccattgt cctgttctga cttatatgat gcggtacaca gagccatcca agtaagtgat    16380
ggctcagcag tggaatactc tgggaattag gctgaaccac atgaaagagt gctttatagg    16440
gcaaaaacag ttgaatatca gtgatttcac atggttcaac ctaatagttc aactcatcct    16500
```

```
ttccattgga gaatatgatg gatctacctt ctgtgaactt tatagtgaag aatctgctat    16560
tacatttcca atttgtcaac atgctgagct ttaataggac ttatcttctt atgcaacat     16620 ttattggtgt gtccccttgc ctagcccaac agaagaattc agcagccgta agtctaggac    16680
aggcttaaat tgttttcact ggtgtaaatt gcagaaagat gatctaagta atttggcatt    16740
tattttaata ggtttgaaaa acacatgcca ttttacaaat aagacttata tttgtccttt    16800 tgttttcag cctaccatga gaataagaga aagaaaatga agatcaaaag cttattcatc     16860 tgttttctt tttcgttggt gtaaagccaa caccctgtct aaaaaacata aatttcttta    16920
atcattttgc ctcttttctc tgtgcttcaa ttaataaaaa atggaaagaa tctaatagag    16980
tggtacagca ctgttatttt tcaaagatgt gttgctatcc tgaaaattct gtaggttctg    17040
tggaagttcc agtgttctct cttattccac ttcggtagag gatttctagt ttcttgtggg    17100
ctaattaaat aaatcattaa tactcttcta agttatggat tataaacatt caaaataata    17160
ttttgacatt atgataattc tgaataaaag aacaaaaacc atggtatagg taaggaatat    17220
aaaacatggc ttttacctta gaaaaaacaa ttctaaaatt catatggaat caaaaaagag    17280
cctgcagaac caaagtaaga ctaagcaaaa agaacaaatt acctgatttc aaactacact    17340
ataaggccat agtcaccgaa acagcaaggt actggtataa actcgagata acttcgtata    17400
atgtatgcta tacgaagtta tgctaggtaa ctataacggt cctaaggtag cgagctagca    17460
cacatcacaa ccacaaccct ctcaggtaac tatacttggg acttaaaaaa cataatcata    17520 atcattttc ctaaaacgat caagactgat aaccatttga caagagccat acagacaagc     17580
accagctggc actcttaggt cttcacgtat ggtcatcagt ttgggttcca tttgtagata    17640
agaaactgaa catataaagg tctaggttaa tgcaatttac acaaaaggag accaaaccag    17700
ggagagaagg aaccaaaatt aaaaattcaa accagagcaa aggagttagc cctggttttg    17760
ctctgact                                                            17768

<210> SEQ ID NO 19
<211> LENGTH: 120
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(60)
<223> OTHER INFORMATION: Mouse Sequence
<220> FEATURE:
<221> NAME/KEY: misc_feature
<222> LOCATION: (61)..(120)
<223> OTHER INFORMATION: Human Sequence

<400> SEQUENCE: 19
agagcgagtc tttctgcaca cagatcacct ttcctatcaa ccccactagc ctctggcaaa      60
atgaagtggg taacctttat ttcccttctt tttctcttta gctcggctta ttccaggggt    120

<210> SEQ ID NO 20
<211> LENGTH: 160
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(60)
<223> OTHER INFORMATION: Human Sequence
<220> FEATURE:
```

```
<221> NAME/KEY: misc_feature
<222> LOCATION: (61)..(66)
<223> OTHER INFORMATION: XhoI
<220> FEATURE:
<221> NAME/KEY: misc_feature
<222> LOCATION: (67)..(100)
<223> OTHER INFORMATION: LoxP
<220> FEATURE:
<221> NAME/KEY: misc_feature
<222> LOCATION: (101)..(160)
<223> OTHER INFORMATION: Cassette

<400> SEQUENCE: 20
cctgatttca aactacacta taaggccata gtcaccgaaa cagcaaggta ctggtataaa       60
ctcgagataa cttcgtataa tgtatgctat acgaagttat atgcatgcca gtagcagcac      120
ccacgtccac cttctgtcta gtaatgtcca cacctccct                             160

<210> SEQ ID NO 21
<211> LENGTH: 192
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(60)
<223> OTHER INFORMATION: Cassette
<220> FEATURE:
<221> NAME/KEY: misc_feature
<222> LOCATION: (61)..(94)
<223> OTHER INFORMATION: LoxP
<220> FEATURE:
<221> NAME/KEY: misc_feature
<222> LOCATION: (101)..(126)
<223> OTHER INFORMATION: I-CeuI
<220> FEATURE:
<221> NAME/KEY: misc_feature
<222> LOCATION: (127)..(132)
<223> OTHER INFORMATION: NheI
<220> FEATURE:
<221> NAME/KEY: misc_feature
<222> LOCATION: (133)..(192)
<223> OTHER INFORMATION: Mouse Sequence

<400> SEQUENCE: 21
cattctcagt attgttttgc caagttctaa ttccatcaga cctcgacctg cagcccctag       60
ataacttcgt ataatgtatg ctatacgaag ttatgctagg taactataac ggtcctaagg      120
tagcgagcta gcacacatca caaccacaac cttctcaggt aactatactt gggacttaaa      180
aaacataatc at                                                          192

<210> SEQ ID NO 22
<211> LENGTH: 198
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(60)
<223> OTHER INFORMATION: Human Sequence
<220> FEATURE:
<221> NAME/KEY: misc_feature
<222> LOCATION: (61)..(66)
<223> OTHER INFORMATION: XhoI
<220> FEATURE:
<221> NAME/KEY: misc_feature
<222> LOCATION: (67)..(100)
<223> OTHER INFORMATION: LoxP
<220> FEATURE:
<221> NAME/KEY: misc_feature
```

```
<222> LOCATION: (107)..(132)
<223> OTHER INFORMATION: I-CeuI
<220> FEATURE:
<221> NAME/KEY: misc_feature
<222> LOCATION: (133)..(138)
<223> OTHER INFORMATION: NheI
<220> FEATURE:
<221> NAME/KEY: misc_feature
<222> LOCATION: (139)..(198)
<223> OTHER INFORMATION: Mouse Sequence

<400> SEQUENCE: 22
cctgatttca aactacacta taaggccata gtcaccgaaa cagcaaggta ctggtataaa     60
ctcgagataa cttcgtataa tgtatgctat acgaagttat gctaggtaac tataacggtc    120
ctaaggtagc gagctagcac acatcacaac cacaaccttc tcaggtaact atacttggga    180
cttaaaaaac ataatcat                                                  198

<210> SEQ ID NO 23
<211> LENGTH: 29
<212> TYPE: DNA
<213> ORGANISM: Artificial Sequence
<220> FEATURE:
<223> OTHER INFORMATION: Synthetic

<400> SEQUENCE: 23
gtaaccttta tttcccttct ttttctctt                                       29

<210> SEQ ID NO 24
<211> LENGTH: 14
<212> TYPE: DNA
<213> ORGANISM: Artificial Sequence
<220> FEATURE:
<223> OTHER INFORMATION: Synthetic

<400> SEQUENCE: 24
agctcggctt attc                                                       14

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cgtgcatctc gacgaaacac                                                 20

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26
gcagaaccaa agtaagacta agcaaa                                          26

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
```
agaacaaatt acctgatttc                                              20

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
tgtttcggtg actatggcct tat                                          23

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
gccgagaagc acgtaagagt tt                                           22

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30 atgtttttc atctctgctt gt                                            22

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
aataccaggc ttccattact agaaaaa                                      27

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ccctcccatg gcctaacaac                                              20

<210> SEQ ID NO 33
<211> LENGTH: 25
<212> TYPE: DNA
<213> ORGANISM: Artificial Sequence
<220> FEATURE:
<223> OTHER INFORMATION: Synthetic

<400> SEQUENCE: 33
ttgggcacaa cagatgtcag agagc                                        25

<210> SEQ ID NO 34
<211> LENGTH: 19
<212> TYPE: DNA
<213> ORGANISM: Artificial Sequence
<220> FEATURE:
<223> OTHER INFORMATION: Synthetic

<400> SEQUENCE: 34
acgtgccttg cattgctta                                            19

<210> SEQ ID NO 35
<211> LENGTH: 17335
<212> TYPE: DNA
<213> ORGANISM: Homo sapiens

<400> SEQUENCE: 35

| | | | | | |
|---|---|---|---|---|---|
| atgaagtggg | taacctttat | ttccttctt | tttctcttta | gctcggctta | ttccaggggt | 60 |
| gtgtttcgtc | gagatgcacg | taagaaatcc | attttctat | tgttcaactt | ttattctatt | 120 |
| ttcccagtaa | aataaagttt | tagtaaactc | tgcatcttta | aagaattatt | ttggcattta | 180 |
| tttctaaaat | ggcatagtat | tttgtatttg | tgaagtctta | caaggttatc | ttattaataa | 240 |
| aattcaaaca | tcctaggtaa | aaaaaaaaaa | aggtcagaat | tgtttagtga | ctgtaattt | 300 |
| cttttgcgca | ctaaggaaag | tgcaaagtaa | cttagagtga | ctgaaacttc | acagaatagg | 360 |
| gttgaagatt | gaattcataa | ctatcccaaa | gacctatcca | ttgcactatg | ctttattaa | 420 |
| aaaccacaaa | acctgtgctg | ttgatctcat | aaatagaact | tgtatttata | tttattttca | 480 |
| ttttagtctg | tcttcttggt | tgctgttgat | agacactaaa | agagtattag | atattatcta | 540 |
| agtttgaata | taaggctata | aatatttaat | aatttttaaa | atagtattct | tggtaattga | 600 |
| attattcttc | tgtttaaagg | cagaagaaat | aattgaacat | catcctgagt | ttttctgtag | 660 |
| gaatcagagc | ccaatatttt | gaaacaaatg | cataatctaa | gtcaaatgga | aagaaatata | 720 |
| aaaagtaaca | ttattacttc | ttgttttctt | cagtatttaa | caatccttt | ttttcttccc | 780 |
| ttgcccagac | aagagtgagg | ttgctcatcg | gtttaaagat | tgggagaag | aaaatttcaa | 840 |
| agccttgtaa | gttaaaatat | tgatgaatca | aatttaatgt | ttctaatagt | gttgtttatt | 900 |
| attctaaagt | gcttatattt | ccttgtcatc | agggttcaga | ttctaaaaca | gtgctgcctc | 960 |
| gtagagtttt | ctgcgttgag | gaagatattc | tgtatctggg | ctatccaata | aggtagtcac | 1020 |
| tggtcacatg | gctattgagt | acttcaaata | tgacaagtgc | aactgagaaa | caaaaactta | 1080 |
| aattgtattt | aattgtagtt | aatttgaatg | tatatagtca | catgtggcta | atggctactg | 1140 |
| tattggacag | tacagctctg | gaacttgctt | ggtggaaagg | actttaatat | aggtttcctt | 1200 |
| tggtggctta | cccactaaat | cttctttaca | tagcaagcat | tcctgtgctt | agttgggaat | 1260 |
| attaattt | tttttttttt | taagacaggg | tctcgctctg | tcgcccaggc | tggagtgcag | 1320 |
| tggcgcaatc | tcggctcact | gcaaactccg | cctcccgggt | tcacgccatt | ctcctgcctc | 1380 |
| agcctcccga | gtagctggga | ctacaggcgc | ccgccatcac | gcccggctaa | tctttgtat | 1440 |
| ttttagtaga | gatggggttt | caccgtgtgc | caggatggtc | tcaatctcct | gacatcgtga | 1500 |
| tctgcccacc | tcggcctccc | aaagtgctgg | gattacagga | gtgagccacc | gcgcccggcc | 1560 |
| tatttaaatg | ttttttaatc | tagtaaaaaa | tgagaaaatt | gttttttaa | aagtctacct | 1620 |
| aatcctacag | gctaattaaa | gacgtgtgtg | gggatcaggt | gcggtggttc | acacctgtaa | 1680 |
| tcccagcact | ttggaaggct | gatgcaggag | gattgcttga | gccaggagt | tcaagaccag | 1740 |
| cctgggcaag | tctctttaaa | aaaacaaaa | caaacaaaca | aaaaattag | gcatggtggc | 1800 |
| acatgcctgt | agtcctagct | acttaggagg | ctgacgtagg | aggatcgttt | ggacctgaga | 1860 |
| ggtcaaggct | acagtgagcc | atgattgtgc | cactgcactc | cagcctgggt | gacagagtga | 1920 |

```
gactctgtct caaaaaagaa aaaggaaatc tgtggggttt gttttagttt taagtaattc    1980
taaggacttt aaaaatgcct agtcttgaca attagatcta tttggcatac aatttgcttg    2040
cttaatctat gtgtgtgcat agatctactg acacacgcat acatataaac attagggaac    2100
taccattctc tttgcgtagg aagccacata tgcctatcta ggcctcagat catacctgat    2160
atgaataggc tttctggata atggtgaaga agatgtataa aagatagaac ctatacccat    2220
acatgatttg ttctctagcg tagcaacctg ttacatatta aagttttatt atactacatt    2280
tttctacatc ctttgtttca gggtgttgat tgcctttgct cagtatcttc agcagtgtcc    2340
atttgaagat catgtaaaat tagtgaatga agtaactgaa tttgcaaaaa catgtgttgc    2400
tgatgagtca gctgaaaatt gtgacaaatc acttgtaagt acattctaat tgtggagatt    2460
ctttcttctg tttgaagtaa tcccaagcat ttcaaaggaa ttttttttaa gttttctcaa    2520
ttattattaa gtgtcctgat ttgtaagaaa cactaaaaag ttgctcatag actgataagc    2580
cattgtttct tttgtgatag agatgcttta gctatgtcca cagttttaaa atcatttctt    2640
tattgagacc aaacacaaca gtcatggtgt atttaaatgg caatttgtca tttataaaca    2700
cctcttttta aaatttgagg tttggtttct ttttgtagag gctaataggg atatgatagc    2760
atgtatttat ttatttattt atcttatttt attatagtaa gaacccttaa catgagatct    2820
accctgttat attttaagt gtacaatcca ttattgttaa ctacgggtac actgttgtat    2880
agcttactca tcttgctgta ttaaaacttt gtgcccattg attagtaacc cctcgtttcg    2940
tcctccccca gccactggca accagcatta tactctttga ttctatgagt ttgactactt    3000
tagctacctt atataagtgg tattatgtac tgtttatctt tttatgactg acttatttcc    3060
cttagcatag tgcattcaaa gtccaaccat gttgttgcct attgcagaat ttccttcttt    3120
tcaaggctga ataatattcc agtgcatgtg tgtaccacat tttctttatc cattaatttg    3180
ttgattgata gacatttagg ttggttttct acatcttgac tatcatgaat agtgttgcaa    3240
tgaacacagg agagctacta tctcttagag atgatatcat ggttttttatc atcagaaaac    3300 acccactgat ttctatgcta attttgttac ctgggtggaa taatagtaca gctatatatt    3360 cctcattttta gatatctttg tatttctaca tacaataaaa aagcagagta cttagtcatg    3420
ttgaagaact ttaaactttt agtatttcca gatcaatctt caaaacaagg acaggtttat    3480
ctttctctca ccactcaatc tatatatacc tcttgtgggc aaggccagtt tttatcactg    3540
gagcctttcc cctttttatt atgtacctct ccctcacagc agagtcagga ctttaacttt    3600
acacaatact atggctctac atatgaaatc ttaaaaatac ataaaaatta ataaattctg    3660
tctagagtag tatattttcc ctggggttac agttactttc ataataaaaa ttagagataa    3720
ggaaaggact catttattgg aaagtgattt taggtaacat ttctggaaga aaaatgtcta    3780
tatcttaata gtcacttaat atatgatgga ttgtgttact cctcagtttt caatggcata    3840
tactaaaaca tggccctcta aaaggggggc aaatgaaatg agaaactctc tgaatgtttt    3900
tctcccctag gtgaattcac ctgctgctta gaagcttatt ttctcttgat ttctgttata    3960
atgattgctc ttacccttta gttttaagtt tcaaaatagg agtcatataa ctttccttaa    4020
agctattgac tgtcttttg tcctgttta ttccatgat gttatagtgt gacagttaat    4080
tcttatgaaa attatataga gatggttaaa tcatcagaaa ctgtaaacct cgattgggag    4140
gggaagcgga ttttttaaatg atttcctgac caagcttaac cagtatatta aatcctttgt    4200
actgttcttt ggctataaag aaaaaaggta ctgtccagca actgaaacct gctttcttcc    4260
atttagcata ccctttttgg agacaaatta tgcacagttg caactcttcg tgaaacctat    4320
```

```
ggtgaaatgg ctgactgctg tgcaaaacaa gaacctgaga gaaatgaatg cttcttgcaa   4380
cacaaagatg acaacccaaa cctcccccga ttggtgagac cagaggttga tgtgatgtgc   4440
actgcttttc atgacaatga agagacattt ttgaaaaagt aagtaatcag atgtttatag   4500
ttcaaaatta aaaagcatgg agtaactcca taggccaaca ctctataaaa attaccataa   4560
caaaaatatt ttcaacatta agacttggaa gttttgttat gatgattttt taaagaagta   4620
gtatttgata ccacaaaatt ctacacagca aaaaatatga tcaaagatat tttgaagttt   4680
attgaaacag gatacaatct ttctgaaaaa tttaagatag acaaattatt taatgtatta   4740
cgaagatatg tatatatggt tgttataatt gatttcgttt tagtcagcaa cattatattg   4800
ccaaaattta accatttatg cacacacaca cacacacaca cacacttaac cctttttttcc   4860 acatacttaa agaatgacag agacaagacc atcatgtgca aattgagctt aattggttaa   4920
ttagatatct ttggaatttg gaggttctgg ggagaatgtc gattacaatt atttctgtaa   4980
tattgtctgc tatagaaaag tgactgtttt tcttttttcaa aatttagata cttatatgaa   5040
attgccagaa gacatcctta ctttttatgcc ccggaactcc ttttctttgc taaaaggtat   5100
aaagctgctt ttacagaatg ttgccaagct gctgataaag ctgcctgcct gttgccaaag   5160
gtattatgca aaagaataga aaaaaagagt tcattatcca acctgatttt gtccattttg   5220
tggctagatt tagggaacct gagtgtctga tacaaacttt ccgacatggt caaaaaagcc   5280 ttcctttttat ctgtcttgaa aatctttcat cttttgaaggc ctacactctc gtttcttctt   5340
ttaagatttg ccaatgatga tctgtcagag gtaatcactg tgcatgtgtt taaagatttc   5400 accactttttt atggtggtga tcactatagt gaaatactga aacttgtttg tcaaattgca   5460
cagcaagggg ccacagttct tgtttatctt ttcatgataa tttttagtag ggagggaatt   5520
caaagtagag aattttactg catctagatg cctgagttca tgcattcatt ccataaatat   5580
atattatgga atgctttatt ttcttttctg aggagtttac tgatgttggt ggaggagaga   5640
ctgaaatgaa ttatacacaa aatttaaaaa ttagcaaaat tgcagcccct gggatattag   5700
cgtactcttt ctctgacttt tctcccactt ttaaggctct ttttcctggc aatgtttcca   5760
gttggtttct aactacatag ggaattccgc tgtgaccaga atgatcgaat gatctttcct   5820
tttcttagag agcaaaatca ttattcgcta aagggagtac ttgggaattt aggcataaat   5880
tatgccttca aaatttaatt tggcacagtc tcatctgagc ttatggaggg gtgtttcatg   5940 tagaatttttt cttctaattt tcatcaaatt attccttttt gtagctcgat gaacttcggg   6000
atgaagggaa ggcttcgtct gccaaacaga gactcaagtg tgccagtctc caaaaatttg   6060
gagaaagagc tttcaaagca tggtaaatac tttttaaacat agttggcatc tttataacga   6120
tgtaaatgat aatgcttcag tgacaaattg tacatttttta tgtatttttgc aaagtgctgt   6180 caaatacatt tctttggttg tctaacaggt agaactctaa tagaggtaaa aatcagaata   6240
tcaatgacaa tttgacatta ttttttaatct tttcttttct aaatagttga ataatttaga   6300
ggacgctgtc ctttttgtcc taaaaaaagg gacagatatt taagttctat ttatttataa   6360
aatcttggac tcttattcta atggttcatt attttttatag agctgtaggc atggttcttt   6420
atttaatttt ttaaagttat ttttaatttt tgtggataca gagtaggtat acatatttac   6480
ggggtatatg agatattttg atataagtat acaacatata taatcccttt atttaatttt   6540
atcttccccc caatgatcta aaactatttg cttgtccttt tatgtcttat agttaaattc   6600
agtcaccaac taagttgaag ttacttctta tttttgcata gctccagctc tgatcttcat   6660
```

```
ctcatgtttt tgcctgagcc tctgttttca tattacttag ttggttctgg gagcatactt   6720
taatagccga gtcaagaaaa atactagctg ccccgtcacc cacactcctc acctgctagt   6780
caacagcaaa tcaacacaac aggaaataaa atgaaaataa tagacattat gcatgctctc   6840
tagaaactgt caattgaact gtatttgctc atcattccta ccatctacac caccaaaatc   6900
aaccaaattt atgaaaaaaa acagccccaa cataaaatta tacacagata aacaggctat   6960
gattggtttt gggaagaag tcacctttac ctgatttagg caactgtgaa atgactagag    7020
aatgaagaaa attagacgtt tacatcttgt catagagttt gaagatagtg ctggatcttt   7080 cttttatataa gtaagatcaa taaaaactcc ctcattctgt agaagttatg atttctttc   7140 taagagacct ttagaagtca gaaaaatgt gtttcaattg agaaaaaaga taactggagt   7200
ttgtgtagta cttcccagat tataaaatgc ttttgtatgt attatctaat ttaatcctca   7260
aaacttcttc aatttagcat gttgtcatga cactgcagag gctgaagctc agagaggctg   7320
agccctctgc taacaagtcc tactgctaac aagtgataaa gccagagctg gaagtcacat   7380
ctggactcca aacctgatgc ttctcagcct gttgcccctt ttagagttcc ttttttaattt   7440 ctgcttttat gacttgctag atttctacct accacacaca ctcttaaatg gataattctg   7500
ccctaaggat aagtgattac catttggttc agaactagaa ctaatgaatt ttaaaaatta   7560
tttctgtatg tccattttga attttcttat gagaaatagt atttgcctag tgttttcata   7620
taaaatatcg catgataata ccattttgat tggcgatttt cttttaggg cagtagctcg    7680 cctgagccag agatttccca aagctgagtt tgcagaagtt tccaagttag tgacagatct   7740
taccaaagtc cacacggaat gctgccatgg agatctgctt gaatgtgctg atgacagggt   7800
aaagagtcgt cgatatgctt tttggtagct tgcatgctca agttggtaga atggatgcgt   7860
ttggtatcat tggtgatagc tgacagtggg ttgagattgt cttctgtgct ttcgtctgtc   7920
ctatcttcaa tcttttccctg cctatggtgg tggtaccttt ctgttttttaa cctggctata   7980 aattaccaga taaacccatt cactgatttg taactccttt cagtcatgct ctaactgtaa   8040
atgaaggctt aaactgaagt agaacagtta caaggtttta cttggcagaa catcttgcaa   8100
ggtagatgtc taagaagatt ttttttctt tttttaagac agagtttcgc tcttgtttcc   8160
caggctgggg tgcaatggtg tgatcttggc tcagcgcaac ctctgcctcc tgggttcaag   8220
tgattctcat gcctcagcct cccaagtagc tgggattaca ggcatgcgcc accacctg    8280 gctaattttg tattttagt agaggcgggg tttcaccata ttgtccagac tggtctcgaa   8340
ctcctgacct caggtgatcc acccgccttg gcctcccaaa gtgctgggat tacaggcatg   8400
agccaccttg cccagcctaa aagatttttt tgagggaggt aggtggactt ggagaaggtc   8460
actacttgaa gagattttg gaatgatgt attttttcttc tctatattcc ttcccttaat   8520
taactctgtt tgttagatgt gcaaatattt ggaatgatat ctcttttctc aaaacttata   8580
atattttctt tctcccttc ttcaagatta aacttatggg caaatactag aatcctaatc   8640
tctcatggca ctttctggaa aatttaaggc ggttatttta tatatgtaag cagggcctat   8700
gactatgatc ttgactcatt tttcaaaaat cttctatatt ttatttagtt atttggtttc   8760
aaaaggcctg cacttaattt tgggggatta tttggaaaaa cagcattgag ttttaatgaa   8820
aaaaacttaa atgccctaac agtagaaaca taaaattaat aaataactga gctgagcacc   8880
tgctactgat tagtctattt taattaagtg ggaatgtttt tgtagtccta tctacatctc   8940
caggtttagg agcaaacaga gtatgttcat agaaggaata tgtgtatggt cttagaatac   9000
aatgaatatg ttctgccaac ttaataaagg tctgaggaga aagtgtagca atgtcaattc   9060
```

```
gtgttgaaca atttccacca acttacttat aggcggacct tgccaagtat atctgtgaaa    9120
atcaagattc gatctccagt aaactgaagg aatgctgtga aaaacctctg ttggaaaaat    9180
cccactgcat tgccgaagtg gaaaatgatg agatgcctgc tgacttgcct tcattagctg    9240
ctgattttgt tgaaagtaag gatgtttgca aaaactatgc tgaggcaaag gatgtcttcc    9300
tgggcatgta agtagataag aaattattct tttatagctt tggcatgacc tcacaactta    9360
ggaggatagc ctaggctttt ctgtggagtt gctacaattt ccctgctgcc cagaatgttt    9420
cttcatcctt cccttttccca ggctttaaca attttttgaaa tagttaatta gttgaataca   9480
ttgtcataaa ataatacatg ttcatggcaa agctcaacat tccttactcc ttaggggtat    9540
ttctgaaaat acgtctagaa acattttgtg tatatataaa ttatgtatac ttcagtcatt    9600
cattccaagt gtatttcttg aacatctata atatatgtgt gtgactatgt attgcctgtc    9660
tatctaacta atctaatcta atctagtcta tctatctaat ctatgcaatg atagcaaaga    9720
agtataaaaa gaaatataga gtctgacacc aggtgcttta tatttggtga aaagaccaga    9780
agttcagtat aatggcaata tggtaggcaa ctcaattaca aaataaatgt ttacatattg    9840
tcagaagttg tggtgataaa ctgcattttt gttgttggat tatgataatg cactaaataa    9900
tatttcctaa aattatgtac cctacaagat ttcactcata cagagaagaa agagaatatt    9960
ttaagaacat atctctgccc atctatttat cagaatcctt ttgagatgta gtttaaatca   10020
aacaaaatgt taataaaaat aacaagtatc attcatcaaa gacttcatat gtgccaagca   10080
gtgtgtgctt tgtgtagatt atgtcatata gttctcataa tccaccttcc gagacagata   10140
ctatttattt tttgagacag agttttactc ttgttgccca ggctggagtg caatggtgcc   10200
atctcggctc accacaacct ccgcctccca ggttcaagcg attctcctgc ctcagcctcc   10260
tgggattaca ggcatgcacc accatgcctg gctaattttg tatttttagt agagatgggg   10320
tttcaccatg ttggtcagac tggtctcaaa ctcctgacct ctggtgatat gcctgcctca   10380
gcctcctaaa gtgctgggat tacaggcatg agccactgtg cccagccgac agatactatt   10440
attatttcca ttctaccgag aaggagacta aggctctgat catttaaata agttgcctaa   10500
ggtgatgcag tgatataagt agcagagcta ggaattgagc cttggtaact ttaactctgg   10560
accccaagtc cttagctact aagctttact gcatggggtt tagtcaaatt aagacttttg   10620
gaatatgagt tacttttgag attagctttg tgatattttt tgtgctcatt tgtccaacaa   10680
agtctatttt attttcatct taattaggtt tttgtatgaa tatgcaagaa ggcatcctga   10740
ttactctgtc gtgctgctgc tgagacttgc caagacatat gaaaccactc tagagaagtg   10800
ctgtgccgct gcagatcctc atgaatgcta tgccaaagtg gtaggtttat tgttggaaaa   10860
aaatgtagtt ctttgactga tgattccaat aatgagaaag aaaaataatg caagaatgta   10920
aaatgatata cagtgcaatt tagatctttt cttgagatgg tttcaattct ggaatcttaa   10980
acatgaaaga aaaagtagcc ttagaatgat taacaaaatt tagactagtt agaatagaaa   11040
gatctgaata gagcaatctc taaaaaattt tgatcttttt ttctcttttt cacaatcctg   11100
agaacaaaaa aaaattaaat ttaaatgtta attagaagat atttaactta gatgtaaagt   11160
gagttaacct gattccagga ttaatcaagt actagaatta gtatcttatg gcaaattata   11220
gaacctatcc ctttagaata ttttcaaatc tttttgagga tgtttaggaa tagttttaca   11280
agaaattaag ttaggagagg aaatctgttc tggaggattt ttagggttcc cactagcata   11340
tgtaatggtt tctgaactat tcagaatcag agaaaactca tttttcctgc tttcaagaag   11400
```

```
ctactgtatg ccaggcacca tgcacaaaca atgaccaacg taaaatctct cattttggag  11460
agcctggaat ctaactggaa aggtgaacta ataataataa tatgtacaat catagccatc  11520
atttattaaa cttttattat atgcaaggca ctgtttaatt tcattagctt acctggttta  11580
cagagcagct ctatgagatg agtgccatct ttgcccctat tttagggata aggattctga  11640
aatgtggaga tggtaagtaa aattgcacaa ctgaagaatg agttacatga cttggctcaa  11700
atactggtca ttgaactcca gagcctgaat attcttaacc acttacatga tgcaagctca  11760
ccaaataaat agttcgaatg tattgtgaca gagcggcatt gatattcatc tattcatgtg  11820
gctttgagta ggaagaagaa aggatatcat tctgaccaga ggggtgaaaa acaacctgca  11880
tctgatcctg aggcataata ctattaacac aattctttta tgtttcagtt cgatgaattt  11940
aaacctcttg tggaagagcc tcagaattta atcaaacaaa attgtgagct ttttgagcag  12000
cttggagagt acaaattcca gaatgcgtaa gtaatttttta ttgactgatt tttttttatca  12060
atttgtaatt atttaagact taatatatga gccacctagc atagaacttt taagaatgaa  12120
aatacattgc atatttctaa tcactctttg tcaagaaaga taggagagga gagataaaat  12180
agttgatggg gtggagaggt ctatatttga atgtagtcta aaaattgttc tcttaagatt  12240
ggaagtatgt aggctgggag ggtaaatacc aaatcttggt atatcagaac tgagcatgtc  12300
ccttgaaggt taagaaatag ttaatgggca aatagagcat ggcaatattt tgtagagcag  12360
caagtagtag gccttgaata gatgtcgctc aaaaagtaat atgtaagctg aacacaaaaa  12420
tgtaacaaat gaatttagat acatatttga atattaaatt caggttgttt gggagatgca  12480
cctagtcttt gatggttaaa cctttccctc catagaagag acagagacag aatggcttgc  12540
tggactaatg tcccaattca atagagtctt atctatgaag gttaaaaaca agaagagaca  12600
tattatacag tagatattta ttgtgtggct catacacatg gtgctcttct gattatggat  12660
tttagagata ataacagtga acaagacata gtttctttcc tcgagtagat taaagtcata  12720
cattgacttt taatggtgac tggcattctt aatacatgat tattatatat taggtaccat  12780
gtcagattaa ttataatact ttactacttt taatttaacc cttgaactat ccctattgag  12840
tcagatatat ttccttccat tttctacttg tatctttcaa gtttagcata tgctgataca  12900
tatgaagctc tctccaggtt ttattgaaag aagaaattaa taaatttatt aatgtcactg  12960
aattaggcaa ctcactttcc caagattatg caagtggtac aggtggaact caaagccaag  13020
tttaactagt tgttcaggag aatgttttct accctccact aacccactac tctgcagatg  13080
gagataatat gatgaatgga acatagcaac atcttagttg attccggcca agtgttctct  13140
gttttatcta ctatgttaga cagtttcttg ccttgctgaa aacacatgac ttcttttttt  13200
caggctatta gttcgttaca ccaagaaagt accccaagtg tcaactccaa ctcttgtaga  13260
ggtctcaaga aacctaggaa aagtgggcag caaatgttgt aaacatcctg aagcaaaaag  13320
aatgccctgt gcagaagact atgtgagtct ttaaaaaaat ataataaatt aataatgaaa  13380
aaattttacc tttagatatt gataatgcta gctttcataa gcagaaggaa gtaatgtgtg  13440
tgtgtgcatg tttgtgtgca tgtgtgtgtg catgcacgtg tgtgtatgtg tgatattggc  13500
agtcaaggcc ccgaggatga taatttttttt ttttttttg agacgagtc tcgctttgtt  13560
gtccaggctg gagtgcagtg gtgccatctc ggctcactgc aacctccgcc tcccaggttc  13620
aagccattct cctgcctcag cctcccaagt agctgggact acaggtgcat gccaccatgc  13680
ctggctaatt ttttgtattt ttagtagaaa attttcagct tcacctcttt tgaatttctg  13740
ctctcctgcc tgttctttag ctatccgtgg tcctgaacca gttatgtgtg ttgcatgaga  13800
```

```
aaacgccagt aagtgacaga gtcaccaaat gctgcacaga atccttggtg aacaggcgac    13860
catgcttttc agctctggaa gtcgatgaaa catacgttcc caaagagttt aatgctgaaa    13920
cattcacctt ccatgcagat atatgcacac tttctgagaa ggagagacaa atcaagaaac    13980
aaacgtgagg agtatttcat tactgcatgt gtttgtagtc ttgatagcaa gaactgtcaa    14040
ttcaagctag caacttttc ctgaagtagt gattatattt cttagaggaa agtattggag     14100 tgttgcccctt attatgctga taagagtacc cagaataaaa tgaataactt tttaaagaca   14160
aaatcctctg ttataatatt gctaaaatta ttcagagtaa tattgtggat taaagccaca    14220
atagaataac atgttaggcc atattcagta gaaaaagatg aacaattaac tgataaattt    14280
gtgcacatgg caaattagtt aatgggaacc ataggagaat ttatttctag atgtaaataa    14340
ttattttaag tttgccctat ggtggcccca cacatgagac aaacccccaa gatgtgactt    14400
ttgagaatga gacttggata aaaaacatgt agaaatgcaa gccctgaagc tcaactccct    14460
attgctatca caggggttat aattgcataa aatttagcta tagaaagttg ctgtcatctc    14520
ttgtgggctg taatcatcgt ctaggcttaa gagtaatatt gcaaaacctg tcatgcccac    14580
acaaatctct ccctggcatt gttgtctttg cagatgtcag tgaaagagaa ccagcagctc    14640
ccatgagttt ggatagcctt attttctata gcctccccac tattagcttt gaagggagca    14700
aagtttaaga accaaatata aagtttctca tctttataga tgagaaaaat tttaaataaa    14760
gtccaagata attaaatttt taaggatcat ttttagctct ttaatagcaa taaaactcaa    14820
tatgacataa tatggcactt ccaaaatctg aataatatat aattgcaatg acatacttct    14880
tttcagagat ttactgaaaa gaaatttgtt gacactacat aacgtgatga gtggtttata    14940
ctgattgttt cagttggtct tcccaccaac tccatgaaag tggattttat tatcctcatc    15000
atgcagatga gaatattgag acttatagcg gtatgcctga gccccaaagt actcagagtt    15060
gcctggctcc aagatttata atcttaaatg atgggactac catccttact ctctccattt    15120
ttctatacgt gagtaatgtt ttttctgttt tttttttttc tttttccatt caaactcagt    15180
gcacttgttg agctcgtgaa acacaagccc aaggcaacaa aagagcaact gaaagctgtt    15240
atggatgatt tcgcagcttt tgtagagaag tgctgcaagg ctgacgataa ggagacctgc    15300
tttgccgagg aggtactaca gttctcttca ttttaatatg tccagtattc attttttgcat   15360 gtttggttag gctagggctt agggatttat atatcaaagg aggctttgta catgtgggac    15420
agggatctta ttttacaaac aattgtctta caaatgaat aaaacagcac tttgttttta     15480
tctcctgctc tattgtgcca tactgttaaa tgtttataat gcctgttctg tttccaaatt    15540
tgtgatgctt atgaatatta ataggaatat ttgtaaggcc tgaaatattt tgatcatgaa    15600
atcaaaacat taatttattt aaacatttac ttgaaatgtg gtggtttgtg atttagttga    15660
ttttataggc tagtgggaga atttacattc aaatgtctaa atcacttaaa attgcccttt    15720
atggcctgac agtaacttt tttattcat ttggggacaa ctatgtccgt gagcttccgt      15780
ccagagatta tagtagtaaa ttgtaattaa aggatatgat gcacgtgaaa tcactttgca    15840
atcatcaata gcttcataaa tgttaatttt gtatcctaat agtaatgcta atattttcct    15900
aacatctgtc atgtctttgt gttcagggta aaaaacttgt tgctgcaagt caagctgcct    15960
taggcttata acatcacatt taaaagcatc tcaggtaact atattttgaa tttttttaaaa   16020 aagtaacctat aatagttatt attaaaatag caaagattga ccatttccaa gagccatata   16080
gaccagcacc gaccactatt ctaaactatt tatgtatgta aatattagct tttaaaattc    16140
```

| | |
|---|---|
| tcaaaatagt tgctgagttg ggaaccacta ttatttctat tttgtagatg agaaaatgaa | 16200 |
| gataaacatc aaagcataga ttaagtaatt ttccaaaggg tcaaaattca aaattgaaac | 16260 |
| caaagtttca gtgttgccca ttgtcctgtt ctgacttata tgatgcggta cacagagcca | 16320 |
| tccaagtaag tgatggctca gcagtggaat actctgggaa ttaggctgaa ccacatgaaa | 16380 |
| gagtgcttta tagggcaaaa acagttgaat atcagtgatt tcacatggtt caacctaata | 16440 |
| gttcaactca tccttttccat tggagaatat gatggatcta ccttctgtga actttatagt | 16500 |
| gaagaatctg ctattacatt tccaatttgt caacatgctg agctttaata ggacttatct | 16560 |
| tcttatgaca acatttattg gtgtgtcccc ttgcctagcc aacagaaga attcagcagc | 16620 |
| cgtaagtcta ggacaggctt aaattgtttt cactggtgta aattgcagaa agatgatcta | 16680 |
| agtaatttgg catttatttt aataggtttg aaaacacat gccattttac aaataagact | 16740 |
| tatatttgtc cttttgtttt tcagcctacc atgagaataa gagaaagaaa atgaagatca | 16800 |
| aaagcttatt catctgtttt tcttttcgt tggtgtaaag ccaacaccct gtctaaaaaa | 16860 |
| cataaatttc tttaatcatt ttgcctcttt tctctgtgct tcaattaata aaaaatggaa | 16920 |
| agaatctaat agagtggtac agcactgtta ttttcaaag atgtgttgct atcctgaaaa | 16980 |
| ttctgtaggt tctgtggaag ttccagtgtt ctctcttatt ccacttcggt agaggatttc | 17040 |
| tagtttcttg tgggctaatt aaataaatca ttaatactct tctaagttat ggattataaa | 17100 |
| cattcaaaat aatattttga cattatgata attctgaata aagaacaaa aaccatggta | 17160 |
| taggtaagga atataaaaca tggcttttac cttagaaaaa acaattctaa aattcatatg | 17220 |
| gaatcaaaaa agagcctgca gaaccaaagt aagactaagc aaaaagaaca aattacctga | 17280 |
| tttcaaacta cactataagg ccatagtcac cgaaacagca aggtactggt ataaa | 17335 |

<210> SEQ ID NO 36
<211> LENGTH: 2076
<212> TYPE: DNA
<213> ORGANISM: Mus musculus

<400> SEQUENCE: 36

| | |
|---|---|
| atattagagc gagtctttct gcacacagat cacctttcct atcaacccca ctagcctctg | 60 |
| gcaaaatgaa gtgggtaacc tttctcctcc tcctcttcgt ctccggctct gcttttttcca | 120 |
| gggtgtgtt tcgccgagaa gcacacaaga gtgagatcgc ccatcggtat aatgatttgg | 180 |
| gagaacaaca tttcaaaggc ctagtcctga ttgcctttc ccagtatctc cagaaatgct | 240 |
| catacgatga gcatgccaaa ttagtgcagg aagtaacaga cttttgcaaag acgtgtgttg | 300 |
| ccgatgagtc tgccgccaac tgtgacaaat cccttcacac tcttttttgga gataagttgt | 360 |
| gtgccattcc aaacctccgt gaaaactatg gtgaactggc tgactgctgt acaaaacaag | 420 |
| agcccgaaag aaacgaatgt ttcctgcaac acaaagatga caaccccagc ctgccaccat | 480 |
| ttgaaaggcc agaggctgag gccatgtgca cctccttaa ggaaaaccca accacccttta | 540 |
| tgggacacta tttgcatgaa gttgccagaa gacatcctta tttctatgcc ccagaacttc | 600 |
| tttactatgc tgagcagtac aatgagattc tgacccagtg ttgtgcagag gctgacaagg | 660 |
| aaagctgcct gaccccgaag cttgatgtgt gaaggagaa agcattggtc tcatctgtcc | 720 |
| gtcagagaat gaagtgctcc agtatgcaga agtttggaga gagagcttt aaagcatggg | 780 |
| cagtagctcg tctgagccag acattcccca atgctgactt tgcagaaatc accaaattgg | 840 |
| caacagacct gaccaaagtc aacaaggagt gctgccatgg tgacctgctg gaatgcgcag | 900 |
| atgacagggc ggaacttgcc aagtacatgt gtgaaaacca ggcgactatc tccagcaaac | 960 |

```
tgcagacttg ctgcgataaa ccactgttga agaaagccca ctgtcttagt gaggtggagc    1020
atgacaccat gcctgctgat ctgcctgcca ttgctgctga ttttgttgag gaccaggaag    1080
tgtgcaagaa ctatgctgag gccaaggatg tcttcctggg cacgttcttg tatgaatatt    1140
caagaagaca ccctgattac tctgtatccc tgttgctgag acttgctaag aaatatgaag    1200
ccactctgga aaagtgctgc gctgaagcca atcctcccgc atgctacggc acagtgcttg    1260
ctgaatttca gcctcttgta gaagagccta agaacttggt caaaaccaac tgtgatcttt    1320
acgagaagct tggagaatat ggattccaaa atgccattct agttcgctac acccagaaag    1380
cacctcaggt gtcaaccccca actctcgtgg aggctgcaag aaacctagga agagtgggca    1440
ccaagtgttg tacacttcct gaagatcaga gactgccttg tgtggaagac tatctgtctg    1500
caatcctgaa ccgtgtgtgt ctgctgcatg agaagacccc agtgagtgag catgttacca    1560
agtgctgtag tggatccctg gtggaaaggc ggccatgctt ctctgctctg acagttgatg    1620
aaacatatgt ccccaaagag tttaaagctg agaccttcac cttccactct gatatctgca    1680
cacttccaga gaaggagaag cagattaaga acaaacggc tcttgctgag ctggtgaagc    1740
acaagcccaa ggctacagcg gagcaactga agactgtcat ggatgacttt gcacagttcc    1800
tggatacatg ttgcaaggct gctgacaagg acacctgctt ctcgactgag ggtccaaacc    1860
ttgtcactag atgcaaagac gccttagcct aaacacatca aaccacaac cttctcaggc    1920 taccctgaga aaaaagaca tgaagactca ggactcatct tttctgttgg tgtaaaatca    1980
acaccctaag gaacacaaat ttcttttaaac atttgacttc ttgtctctgt gctgcaatta    2040
ataaaaaatg gaaagaatct aaaaaaaaaa aaaaaa                              2076

<210> SEQ ID NO 37
<211> LENGTH: 2285
<212> TYPE: DNA
<213> ORGANISM: Homo sapiens

<400> SEQUENCE: 37
ctagcttttc tcttctgtca accccacacg cctttggcac aatgaagtgg gtaacctta      60 tttcccttct ttttctcttt agctcggctt attccagggg tgtgtttcgt cgagatgcac    120
acaagagtga ggttgctcat cggttttaaag atttgggaga agaaaatttc aaagccttgg    180
tgttgattgc ctttgctcag tatcttcagc agtgtccatt tgaagatcat gtaaaattag    240
tgaatgaagt aactgaattt gcaaaaacat gtgttgctga tgagtcagct gaaaattgtg    300
acaaatcact tcatacccct tttggagaca aattatgcac agttgcaact cttcgtgaaa    360
cctatggtga aatggctgac tgctgtgcaa acaagaaacc tgagagaaat gaatgcttct    420
tgcaacacaa agatgacaac ccaaaacctcc ccgattggt gagaccagag ttgatgtga    480 tgtgcactgc ttttcatgac aatgaagaga cattttttgaa aaaatactta tatgaaattg    540
ccagaagaca tccttacttt tatgccccgg aactccttt ctttgctaaa aggtataaag    600
ctgcttttac agaatgttgc caagctgctg ataaagctgc ctgcctgttg ccaaagctcg    660
atgaacttcg ggatgaaggg aaggcttcgt ctgccaaaca gagactcaag tgtgccagtc    720
tccaaaaatt tggagaaaga gctttcaaag catgggcagt agctcgcctg agccagagat    780
ttcccaaagc tgagtttgca gaagtttcca gttagtgac agatcttacc aaagtccaca    840
cggaatgctg ccatggagat ctgcttgaat gtgctgatga cagggcggac cttgccaagt    900
atatctgtga aaatcaagat tcgatctcca gtaaactgaa ggaatgctgt gaaaaacctc    960
```

```
tgttggaaaa atcccactgc attgccgaag tggaaaatga tgagatgcct gctgacttgc    1020
cttcattagc tgctgatttt gttgaaagta aggatgtttg caaaaactat gctgaggcaa    1080
aggatgtctt cctgggcatg ttttgtatg aatatgcaag aaggcatcct gattactctg     1140
tcgtgctgct gctgagactt gccaagacat atgaaaccac tctagagaag tgctgtgccg    1200
ctgcagatcc tcatgaatgc tatgccaaag tgttcgatga atttaaacct cttgtggaag    1260
agcctcagaa tttaatcaaa caaaattgtg agctttttga gcagcttgga gagtacaaat    1320
tccagaatgc gctattagtt cgttacacca agaaagtacc ccaagtgtca actccaactc    1380
ttgtagaggt ctcaagaaac ctaggaaaag tgggcagcaa atgttgtaaa catcctgaag    1440
caaaaagaat gccctgtgca aagactatc tatccgtggt cctgaaccag ttatgtgtgt     1500
tgcatgagaa aacgccagta agtgacagag tcaccaaatg ctgcacagaa tccttggtga    1560
acaggcgacc atgcttttca gctctggaag tcgatgaaac atacgttccc aaagagttta    1620
atgctgaaac attcaccttc catgcagata tatgcacact ttctgagaag gagagacaaa    1680
tcaagaaaca aactgcactt gttgagctcg tgaaacacag gcccaaggca acaaaagagc    1740
aactgaaagc tgttatggat gatttcgcag cttttgtaga gaagtgctgc aaggctgacg    1800
ataaggagac ctgctttgcc gaggagggta aaaaacttgt tgctgcaagt caagctgcct    1860
taggcttata acatcacatt taaaagcatc tcagcctacc atgagaataa gagaaagaaa    1920
atgaagatca aaagcttatt catctgtttt tctttttcgt tggtgtaaag ccaacaccct    1980
gtctaaaaaa cataaatttc tttaatcatt ttgcctcttt tctctgtgct tcaattaata    2040
aaaaatggaa agaatctaat agagtggtac agcactgtta ttttttcaaag atgtgttgct    2100 atcctgaaaa ttctgtaggt tctgtggaag ttccagtgtt ctctcttatt ccacttcggt    2160
agaggatttc tagtttcttg tgggctaatt aaataaatca ttaatactct tctaagttat    2220
ggattataaa cattcaaaat aatattttga cattatgata attctgaata aaagaacaaa    2280
aacca                                                                2285

<210> SEQ ID NO 38
<211> LENGTH: 1391
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(10)
<223> OTHER INFORMATION: 5' NLS
<220> FEATURE:
<221> NAME/KEY: MISC_FEATURE
<222> LOCATION: (1376)..(1391)
<223> OTHER INFORMATION: 3' NLS

<400> SEQUENCE: 38

Met Asp Lys Pro Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60

Thr Ala Glu Ala Thr Arg Leu Lys Arg Thr Ala Arg Arg Arg Tyr Thr
65                  70                  75                  80
```

```
Arg Arg Lys Asn Arg Ile Cys Tyr Leu Gln Glu Ile Phe Ser Asn Glu
                85                  90                  95
Met Ala Lys Val Asp Asp Ser Phe Phe His Arg Leu Glu Glu Ser Phe
            100                 105                 110
Leu Val Glu Glu Asp Lys Lys His Glu Arg His Pro Ile Phe Gly Asn
        115                 120                 125
Ile Val Asp Glu Val Ala Tyr His Glu Lys Tyr Pro Thr Ile Tyr His
    130                 135                 140
Leu Arg Lys Lys Leu Val Asp Ser Thr Asp Lys Ala Asp Leu Arg Leu
145                 150                 155                 160
Ile Tyr Leu Ala Leu Ala His Met Ile Lys Phe Arg Gly His Phe Leu
                165                 170                 175
Ile Glu Gly Asp Leu Asn Pro Asp Asn Ser Asp Val Asp Lys Leu Phe
            180                 185                 190
Ile Gln Leu Val Gln Thr Tyr Asn Gln Leu Phe Glu Glu Asn Pro Ile
        195                 200                 205
Asn Ala Ser Gly Val Asp Ala Lys Ala Ile Leu Ser Ala Arg Leu Ser
    210                 215                 220
Lys Ser Arg Arg Leu Glu Asn Leu Ile Ala Gln Leu Pro Gly Glu Lys
225                 230                 235                 240
Lys Asn Gly Leu Phe Gly Asn Leu Ile Ala Leu Ser Leu Gly Leu Thr
                245                 250                 255
Pro Asn Phe Lys Ser Asn Phe Asp Leu Ala Glu Asp Ala Lys Leu Gln
            260                 265                 270
Leu Ser Lys Asp Thr Tyr Asp Asp Leu Asp Asn Leu Leu Ala Gln
        275                 280                 285
Ile Gly Asp Gln Tyr Ala Asp Leu Phe Leu Ala Ala Lys Asn Leu Ser
    290                 295                 300
Asp Ala Ile Leu Leu Ser Asp Ile Leu Arg Val Asn Thr Glu Ile Thr
305                 310                 315                 320
Lys Ala Pro Leu Ser Ala Ser Met Ile Lys Arg Tyr Asp Glu His His
                325                 330                 335
Gln Asp Leu Thr Leu Leu Lys Ala Leu Val Arg Gln Gln Leu Pro Glu
            340                 345                 350
Lys Tyr Lys Glu Ile Phe Phe Asp Gln Ser Lys Asn Gly Tyr Ala Gly
        355                 360                 365
Tyr Ile Asp Gly Gly Ala Ser Gln Glu Glu Phe Tyr Lys Phe Ile Lys
    370                 375                 380
Pro Ile Leu Glu Lys Met Asp Gly Thr Glu Glu Leu Leu Val Lys Leu
385                 390                 395                 400
Asn Arg Glu Asp Leu Leu Arg Lys Gln Arg Thr Phe Asp Asn Gly Ser
                405                 410                 415
Ile Pro His Gln Ile His Leu Gly Glu Leu His Ala Ile Leu Arg Arg
            420                 425                 430
Gln Glu Asp Phe Tyr Pro Phe Leu Lys Asp Asn Arg Glu Lys Ile Glu
        435                 440                 445
Lys Ile Leu Thr Phe Arg Ile Pro Tyr Tyr Val Gly Pro Leu Ala Arg
    450                 455                 460
Gly Asn Ser Arg Phe Ala Trp Met Thr Arg Lys Ser Glu Glu Thr Ile
465                 470                 475                 480
Thr Pro Trp Asn Phe Glu Glu Val Val Asp Lys Gly Ala Ser Ala Gln
                485                 490                 495
Ser Phe Ile Glu Arg Met Thr Asn Phe Asp Lys Asn Leu Pro Asn Glu
```

```
            500                 505                 510
Lys Val Leu Pro Lys His Ser Leu Leu Tyr Glu Tyr Phe Thr Val Tyr
            515                 520                 525
Asn Glu Leu Thr Lys Val Lys Tyr Val Thr Glu Gly Met Arg Lys Pro
            530                 535                 540
Ala Phe Leu Ser Gly Glu Gln Lys Lys Ala Ile Val Asp Leu Leu Phe
545                 550                 555                 560
Lys Thr Asn Arg Lys Val Thr Val Lys Gln Leu Lys Glu Asp Tyr Phe
            565                 570                 575
Lys Lys Ile Glu Cys Phe Asp Ser Val Glu Ile Ser Gly Val Glu Asp
            580                 585                 590
Arg Phe Asn Ala Ser Leu Gly Thr Tyr His Asp Leu Leu Lys Ile Ile
            595                 600                 605
Lys Asp Lys Asp Phe Leu Asp Asn Glu Glu Asn Glu Asp Ile Leu Glu
            610                 615                 620
Asp Ile Val Leu Thr Leu Thr Leu Phe Glu Asp Arg Glu Met Ile Glu
625                 630                 635                 640
Glu Arg Leu Lys Thr Tyr Ala His Leu Phe Asp Asp Lys Val Met Lys
            645                 650                 655
Gln Leu Lys Arg Arg Arg Tyr Thr Gly Trp Gly Arg Leu Ser Arg Lys
            660                 665                 670
Leu Ile Asn Gly Ile Arg Asp Lys Gln Ser Gly Lys Thr Ile Leu Asp
            675                 680                 685
Phe Leu Lys Ser Asp Gly Phe Ala Asn Arg Asn Phe Met Gln Leu Ile
            690                 695                 700
His Asp Asp Ser Leu Thr Phe Lys Glu Asp Ile Gln Lys Ala Gln Val
705                 710                 715                 720
Ser Gly Gln Gly Asp Ser Leu His Glu His Ile Ala Asn Leu Ala Gly
            725                 730                 735
Ser Pro Ala Ile Lys Lys Gly Ile Leu Gln Thr Val Lys Val Val Asp
            740                 745                 750
Glu Leu Val Lys Val Met Gly Arg His Lys Pro Glu Asn Ile Val Ile
            755                 760                 765
Glu Met Ala Arg Glu Asn Gln Thr Thr Gln Lys Gly Gln Lys Asn Ser
770                 775                 780
Arg Glu Arg Met Lys Arg Ile Glu Glu Gly Ile Lys Glu Leu Gly Ser
785                 790                 795                 800
Gln Ile Leu Lys Glu His Pro Val Glu Asn Thr Gln Leu Gln Asn Glu
            805                 810                 815
Lys Leu Tyr Leu Tyr Tyr Leu Gln Asn Gly Arg Asp Met Tyr Val Asp
            820                 825                 830
Gln Glu Leu Asp Ile Asn Arg Leu Ser Asp Tyr Asp Val Asp His Ile
            835                 840                 845
Val Pro Gln Ser Phe Leu Lys Asp Asp Ser Ile Asp Asn Lys Val Leu
            850                 855                 860
Thr Arg Ser Asp Lys Asn Arg Gly Lys Ser Asp Asn Val Pro Ser Glu
865                 870                 875                 880
Glu Val Val Lys Lys Met Lys Asn Tyr Trp Arg Gln Leu Leu Asn Ala
            885                 890                 895
Lys Leu Ile Thr Gln Arg Lys Phe Asp Asn Leu Thr Lys Ala Glu Arg
            900                 905                 910
Gly Gly Leu Ser Glu Leu Asp Lys Ala Gly Phe Ile Lys Arg Gln Leu
            915                 920                 925
```

```
Val Glu Thr Arg Gln Ile Thr Lys His Val Ala Gln Ile Leu Asp Ser
    930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
        995                 1000                1005

Pro Lys Leu Glu Ser Glu Phe Val Tyr Gly Asp Tyr Lys Val Tyr
    1010                1015                1020

Asp Val Arg Lys Met Ile Ala Lys Ser Glu Gln Glu Ile Gly Lys
    1025                1030                1035

Ala Thr Ala Lys Tyr Phe Phe Tyr Ser Asn Ile Met Asn Phe Phe
    1040                1045                1050

Lys Thr Glu Ile Thr Leu Ala Asn Gly Glu Ile Arg Lys Arg Pro
    1055                1060                1065

Leu Ile Glu Thr Asn Gly Glu Thr Gly Glu Ile Val Trp Asp Lys
    1070                1075                1080

Gly Arg Asp Phe Ala Thr Val Arg Lys Val Leu Ser Met Pro Gln
    1085                1090                1095

Val Asn Ile Val Lys Lys Thr Glu Val Gln Thr Gly Gly Phe Ser
    1100                1105                1110

Lys Glu Ser Ile Leu Pro Lys Arg Asn Ser Asp Lys Leu Ile Ala
    1115                1120                1125

Arg Lys Lys Asp Trp Asp Pro Lys Lys Tyr Gly Gly Phe Asp Ser
    1130                1135                1140

Pro Thr Val Ala Tyr Ser Val Leu Val Val Ala Lys Val Glu Lys
    1145                1150                1155

Gly Lys Ser Lys Lys Leu Lys Ser Val Lys Glu Leu Leu Gly Ile
    1160                1165                1170

Thr Ile Met Glu Arg Ser Ser Phe Glu Lys Asn Pro Ile Asp Phe
    1175                1180                1185

Leu Glu Ala Lys Gly Tyr Lys Glu Val Lys Lys Asp Leu Ile Ile
    1190                1195                1200

Lys Leu Pro Lys Tyr Ser Leu Phe Glu Leu Glu Asn Gly Arg Lys
    1205                1210                1215

Arg Met Leu Ala Ser Ala Gly Glu Leu Gln Lys Gly Asn Glu Leu
    1220                1225                1230

Ala Leu Pro Ser Lys Tyr Val Asn Phe Leu Tyr Leu Ala Ser His
    1235                1240                1245

Tyr Glu Lys Leu Lys Gly Ser Pro Glu Asp Asn Glu Gln Lys Gln
    1250                1255                1260

Leu Phe Val Glu Gln His Lys His Tyr Leu Asp Glu Ile Ile Glu
    1265                1270                1275

Gln Ile Ser Glu Phe Ser Lys Arg Val Ile Leu Ala Asp Ala Asn
    1280                1285                1290

Leu Asp Lys Val Leu Ser Ala Tyr Asn Lys His Arg Asp Lys Pro
    1295                1300                1305

Ile Arg Glu Gln Ala Glu Asn Ile Ile His Leu Phe Thr Leu Thr
    1310                1315                1320
```

```
Asn Leu Gly Ala Pro Ala Ala Phe Lys Tyr Phe Asp Thr Thr Ile
    1325                1330                1335

Asp Arg Lys Arg Tyr Thr Ser Thr Lys Glu Val Leu Asp Ala Thr
    1340                1345                1350

Leu Ile His Gln Ser Ile Thr Gly Leu Tyr Glu Thr Arg Ile Asp
    1355                1360                1365

Leu Ser Gln Leu Gly Gly Asp Lys Arg Pro Ala Ala Thr Lys Lys
    1370                1375                1380

Ala Gly Gln Ala Lys Lys Lys Lys
    1385                1390

<210> SEQ ID NO 39
<211> LENGTH: 4176
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Start Codon
<220> FEATURE:
<221> NAME/KEY: misc_feature
<222> LOCATION: (10)..(30)
<223> OTHER INFORMATION: 5' NLS
<220> FEATURE:
<221> NAME/KEY: misc_feature
<222> LOCATION: (4126)..(4173)
<223> OTHER INFORMATION: 3' NLS
<220> FEATURE:
<221> NAME/KEY: misc_feature
<222> LOCATION: (4174)..(4176)
<223> OTHER INFORMATION: Stop Codon

<400> SEQUENCE: 39
atggacaagc ccaagaaaaa gcggaaagtg aagtacagca tcggcctgga catcggcacc      60
aactctgtgg gctgggccgt gatcaccgac gagtacaagg tgcccagcaa gaaattcaag     120
gtgctgggca acaccgacag gcacagcatc aagaagaacc tgatcggcgc cctgctgttc     180
gacagcggcg aaacagccga ggccaccaga ctgaagagaa ccgccagaag aagatacacc     240
aggcggaaga acaggatctg ctatctgcaa gagatcttca gcaacgagat ggccaaggtg     300
gacgacagct tcttccacag actggaagag tccttcctgg tggaagagga caagaagcac     360
gagagacacc ccatcttcgg caacatcgtg gacgaggtgg cctaccacga agtaccccc     420 accatctacc acctgagaaa gaaactggtg gacagcaccg acaaggccga cctgagactg     480
atctacctgg ccctggccca catgatcaag ttcagaggcc acttcctgat cgagggcgac     540
ctgaaccccg acaacagcga cgtggacaag ctgttcatcc agctggtgca gacctacaac     600
cagctgttcg aggaaaaccc catcaacgcc agcggcgtgg acgccaaggc tatcctgtct     660
gccagactga gcaagagcag aaggctggaa atctgatcg cccagctgcc cggcgagaag     720
aagaacggcc tgttcggcaa cctgattgcc ctgagcctgg cctgacccc caacttcaag     780 agcaacttcg acctggccga ggatgccaaa ctgcagctga gcaaggacac ctacgacgac     840
gacctggaca acctgctggc ccagatcggc gaccagtacg ccgacctgtt cctggccgcc     900
aagaacctgt ctgacgccat cctgctgagc gacatcctga gtgaacac cgagatcacc     960 aaggcccccc tgagcgcctc tatgatcaag agatacgacg agcaccacca ggacctgacc    1020
ctgctgaaag ctctcgtgcg gcagcagctg cctgagaagt acaaagaaat cttcttcgac    1080
cagagcaaga acggctacgc cggctacatc gatggcggcg ctagccagga agagttctac    1140
```

```
aagttcatca agcccatcct ggaaaagatg gacggcaccg aggaactgct cgtgaagctg    1200
aacagagagg acctgctgag aaagcagaga accttcgaca acggcagcat ccccaccag     1260 atccacctgg gagagctgca cgctatcctg agaaggcagg aagattttta cccattcctg    1320
aaggacaacc gggaaaagat cgagaagatc ctgaccttca ggatccccta ctacgtgggc    1380
cccctggcca gaggcaacag cagattcgcc tggatgacca gaaagagcga ggaaaccatc    1440
accccctgga acttcgagga agtggtggac aagggcgcca cgcccagag cttcatcgag     1500 agaatgacaa acttcgataa gaacctgccc aacgagaagg tgctgcccaa gcacagcctg    1560
ctgtacgagt acttcaccgt gtacaacgag ctgaccaaag tgaaatacgt gaccgaggga    1620
atgagaaagc ccgccttcct gagcggcgag cagaaaaagg ccatcgtgga cctgctgttc    1680
aagaccaaca gaaaagtgac cgtgaagcag ctgaaagagg actacttcaa gaaaatcgag    1740
tgcttcgact ccgtggaaat ctccggcgtg gaagatagat caacgcctc cctgggcaca     1800 taccacgatc tgctgaaaat tatcaaggac aaggacttcc tggataacga agagaacgag    1860
gacattctgg aagatatcgt gctgaccctg acactgtttg aggaccgcga gatgatcgag    1920
gaaaggctga aaacctacgc tcacctgttc gacgacaaag tgatgaagca gctgaagaga    1980
aggcggtaca ccggctgggg caggctgagc agaaagctga tcaacggcat cagagacaag    2040
cagagcggca gacaatcct ggatttcctg aagtccgacg gcttcgccaa ccggaacttc      2100
atgcagctga tccacgacga cagcctgaca ttcaaagagg acatccagaa agcccaggtg    2160
tccggccagg gcgactctct gcacgagcat atcgctaacc tggccggcag ccccgctatc    2220
aagaagggca tcctgcagac agtgaaggtg gtggacgagc tcgtgaaagt gatgggcaga    2280
cacaagcccg agaacatcgt gatcgagatg gctagagaga accagaccac ccagaaggga    2340
cagaagaact cccgcgagag gatgaagaga atcgaagagg gcatcaaaga gctgggcagc    2400
cagatcctga aagaacaccc cgtggaaaac acccagctgc agaacgagaa gctgtacctg    2460
tactacctgc agaatggccg ggatatgtac gtggaccagg aactggacat caacagactg    2520
tccgactacg atgtggacca tatcgtgcct cagagctttc tgaaggacga ctccatcgat    2580
aacaaagtgc tgactcggag cgacaagaac agaggcaaga gcgacaacgt gccctccgaa    2640
gaggtcgtga agaagatgaa gaactactgg cgacagctgc tgaacgccaa gctgattacc    2700
cagaggaagt tcgataacct gaccaaggcc gagagaggcg gcctgagcga gctggataag    2760
gccggcttca tcaagaggca gctggtggaa accagacaga tcacaaagca cgtggcacag    2820
atcctggact cccggatgaa cactaagtac gacgaaaacg ataagctgat ccgggaagtg    2880
aaagtgatca ccctgaagtc caagctggtg tccgatttcc ggaaggattt ccagttttac    2940
aaagtgcgcg agatcaacaa ctaccaccac gcccacgacg cctacctgaa cgccgtcgtg    3000
ggaaccgccc tgatcaaaaa gtaccctaag ctggaaagcg agttcgtgta cggcgactac    3060
aaggtgtacg acgtgcggaa gatgatcgcc aagagcgagc aggaaatcgg caaggctacc    3120
gccaagtact tcttctacag caacatcatg aacttttttca agaccgaaat cacccctggcc   3180 aacggcgaga tcagaaagcg ccctctgatc gagacaaacg gcgaaaccgg ggagatcgtg    3240
tgggataagg gcagagactt cgccacagtg cgaaaggtgc tgagcatgcc ccaagtgaat    3300
atcgtgaaaa agaccgaggt gcagacaggc ggcttcagca agagtctat cctgcccaag     3360 aggaacagcg acaagctgat cgccagaaag aaggactggg accccaagaa gtacggcggc    3420
ttcgacagcc ctaccgtggc ctactctgtg ctggtggtgg ctaaggtgga aaagggcaag    3480
tccaagaaac tgaagagtgt gaaagagctg ctggggatca ccatcatgga aagaagcagc    3540
```

| | |
|---|---:|
| tttgagaaga acccuaucga cuuucuggaa gccaagggcu acaaagaagu gaaaaaggac | 3600 |
| ctgatcatca agctgcctaa gtactccctg ttcgagctgg aaaacggcag aaagagaatg | 3660 |
| ctggcctctg ccggcgaact gcagaaggga acgagctgg ccctgcctag caaatatgtg | 3720 |
| aacttcctgt acctggcctc ccactatgag aagctgaagg cagccctga ggacaacgaa | 3780 |
| cagaaacagc tgtttgtgga acagcataag cactacctgg acgagatcat cgagcagatc | 3840 |
| agcgagttct ccaagagagt gatcctggcc gacgccaatc tggacaaggt gctgtctgcc | 3900 |
| tacaacaagc acagggacaa gcctatcaga gagcaggccg agaatatcat ccacctgttc | 3960 |
| accctgacaa acctgggcgc tcctgccgcc ttcaagtact tgacaccac catcgaccgg | 4020 |
| aagaggtaca ccagcaccaa agaggtgctg gacgccaccc tgatccacca gagcatcacc | 4080 |
| ggcctgtacg agacaagaat cgacctgtct cagctgggag cgacaagag acctgccgcc | 4140 |
| actaagaagg ccggacaggc caaaaagaag aagtga | 4176 |

<210> SEQ ID NO 40
<211> LENGTH: 16
<212> TYPE: RNA
<213> ORGANISM: Artificial Sequence
<220> FEATURE:
<223> OTHER INFORMATION: Synthetic

<400> SEQUENCE: 40

| | |
|---|---:|
| guuuuagagc uaugcu | 16 |

<210> SEQ ID NO 41
<211> LENGTH: 67
<212> TYPE: RNA
<213> ORGANISM: Artificial Sequence
<220> FEATURE:
<223> OTHER INFORMATION: Synthetic

<400> SEQUENCE: 41

| | |
|---|---:|
| agcauagcaa guuaaaauaa ggcuaguccg uuaucaacuu gaaaaagugg caccgagucg | 60 |
| gugcuuu | 67 |

<210> SEQ ID NO 42
<211> LENGTH: 77
<212> TYPE: RNA
<213> ORGANISM: Artificial Sequence
<220> FEATURE:
<223> OTHER INFORMATION: Synthetic

<400> SEQUENCE: 42

| | |
|---|---:|
| guuuuagagc uagaaauagc aaguuaaaau aaggcuaguc cguuaucaac uugaaaaagu | 60 |
| ggcaccgagu cggugcu | 77 |

<210> SEQ ID NO 43
<211> LENGTH: 82
<212> TYPE: RNA
<213> ORGANISM: Artificial Sequence
<220> FEATURE:
<223> OTHER INFORMATION: Synthetic

<400> SEQUENCE: 43

| | |
|---|---:|
| guuggaacca uucaaaacag cauagcaagu uaaauaagg cuaguccguu aucaacuuga | 60 |
| aaaaguggca ccgagucggu gc | 82 |

<210> SEQ ID NO 44

```
<211> LENGTH: 76
<212> TYPE: RNA
<213> ORGANISM: Artificial Sequence
<220> FEATURE:
<223> OTHER INFORMATION: Synthetic

<400> SEQUENCE: 44
guuuuagagc uagaaauagc aaguuaaaau aaggcuaguc cguuaucaac uugaaaaagu      60
ggcaccgagu cggugc                                                      76

<210> SEQ ID NO 45
<211> LENGTH: 86
<212> TYPE: RNA
<213> ORGANISM: Artificial Sequence
<220> FEATURE:
<223> OTHER INFORMATION: Synthetic

<400> SEQUENCE: 45
guuuaagagc uaugcuggaa acagcauagc aaguuuaaau aaggcuaguc cguuaucaac      60
uugaaaaagu ggcaccgagu cggugc                                           86

<210> SEQ ID NO 46
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n is a, c, g, or t

<400> SEQUENCE: 46
gnnnnnnnnn nnnnnnnnnn ngg                                              23

<210> SEQ ID NO 47
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n is a, c, g, or t

<400> SEQUENCE: 47
nnnnnnnnnn nnnnnnnnnn ngg                                              23

<210> SEQ ID NO 48
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n is a, c, g, or t

<400> SEQUENCE: 48
ggnnnnnnnn nnnnnnnnnn nnngg                                            25

<210> SEQ ID NO 49
<211> LENGTH: 20
<212> TYPE: RNA
<213> ORGANISM: Artificial Sequence
```

```
<220> FEATURE:
<223> OTHER INFORMATION: Synthetic

<400> SEQUENCE: 49
gagcaaccuc acucuugucu                                                    20

<210> SEQ ID NO 50
<211> LENGTH: 20
<212> TYPE: RNA
<213> ORGANISM: Artificial Sequence
<220> FEATURE:
<223> OTHER INFORMATION: Synthetic

<400> SEQUENCE: 50
ugcauuuguu ucaaaauauu                                                    20

<210> SEQ ID NO 51
<211> LENGTH: 20
<212> TYPE: RNA
<213> ORGANISM: Artificial Sequence
<220> FEATURE:
<223> OTHER INFORMATION: Synthetic

<400> SEQUENCE: 51
auuuaugaga ucaacagcac                                                    20

<210> SEQ ID NO 52
<211> LENGTH: 20
<212> TYPE: RNA
<213> ORGANISM: Artificial Sequence
<220> FEATURE:
<223> OTHER INFORMATION: Synthetic

<400> SEQUENCE: 52
uuaaauaaag cauagugcaa                                                    20

<210> SEQ ID NO 53
<211> LENGTH: 20
<212> TYPE: RNA
<213> ORGANISM: Artificial Sequence
<220> FEATURE:
<223> OTHER INFORMATION: Synthetic

<400> SEQUENCE: 53
uaaagcauag ugcaauggau                                                    20

<210> SEQ ID NO 54
<211> LENGTH: 20
<212> TYPE: RNA
<213> ORGANISM: Artificial Sequence
<220> FEATURE:
<223> OTHER INFORMATION: Synthetic

<400> SEQUENCE: 54
uaauaaaauu caaacauccu                                                    20

<210> SEQ ID NO 55
<211> LENGTH: 20
<212> TYPE: RNA
<213> ORGANISM: Artificial Sequence
<220> FEATURE:
<223> OTHER INFORMATION: Synthetic

<400> SEQUENCE: 55
ugacugaaac uucacagaau                                                    20
```

```
<210> SEQ ID NO 56
<211> LENGTH: 20
<212> TYPE: RNA
<213> ORGANISM: Artificial Sequence
<220> FEATURE:
<223> OTHER INFORMATION: Synthetic

<400> SEQUENCE: 56
gacugaaacu ucacagaaua                                                    20

<210> SEQ ID NO 57
<211> LENGTH: 20
<212> TYPE: RNA
<213> ORGANISM: Artificial Sequence
<220> FEATURE:
<223> OTHER INFORMATION: Synthetic

<400> SEQUENCE: 57
agugcaaugg auaggucuuu                                                    20

<210> SEQ ID NO 58
<211> LENGTH: 20
<212> TYPE: RNA
<213> ORGANISM: Artificial Sequence
<220> FEATURE:
<223> OTHER INFORMATION: Synthetic

<400> SEQUENCE: 58
ccucacucuu gucugggcaa                                                    20

<210> SEQ ID NO 59
<211> LENGTH: 20
<212> TYPE: RNA
<213> ORGANISM: Artificial Sequence
<220> FEATURE:
<223> OTHER INFORMATION: Synthetic

<400> SEQUENCE: 59
accucacucu ugucugggca                                                    20

<210> SEQ ID NO 60
<211> LENGTH: 20
<212> TYPE: RNA
<213> ORGANISM: Artificial Sequence
<220> FEATURE:
<223> OTHER INFORMATION: Synthetic

<400> SEQUENCE: 60
ugagcaaccu cacucuuguc                                                    20

<210> SEQ ID NO 61
<211> LENGTH: 20
<212> TYPE: RNA
<213> ORGANISM: Artificial Sequence
<220> FEATURE:
<223> OTHER INFORMATION: Synthetic

<400> SEQUENCE: 61
uacuuugcac uuuccuuagu                                                    20

<210> SEQ ID NO 62
<211> LENGTH: 20
<212> TYPE: RNA
<213> ORGANISM: Artificial Sequence
<220> FEATURE:
<223> OTHER INFORMATION: Synthetic
```

<400> SEQUENCE: 62
cacucuuguc uguggaaaca                                                    20

<210> SEQ ID NO 63
<211> LENGTH: 6150
<212> TYPE: DNA
<213> ORGANISM: Artificial Sequence
<220> FEATURE:
<223> OTHER INFORMATION: Synthetic

<400> SEQUENCE: 63

| | | | | | |
|---|---|---|---|---|---|
| aacaccccett | gtattactgt | ttatgtaagc | agacagtttt | attgttcatg | atgatatatt | 60 |
| tttatcttgt | gcaatgtaac | atcagagatt | ttgagacacg | ggccagagct | gcatcgcgcg | 120 |
| tttcggtgat | gacggtgaaa | acctctgaca | catgcagctc | ccggagacgg | tcacagcttg | 180 |
| tctgtaagcg | gatgccggga | gcagacaagc | ccgtcagggc | gcgtcagcgg | gtgttggcgg | 240 |
| gtgtcgggc | tggcttaact | atgcggcatc | agagcagatt | gtactgagag | tgcaccatat | 300 |
| gcggtgtgaa | ataccgcaca | gatgcgtaag | gagaaaatac | cgcatcaggc | gccattcgcc | 360 |
| attcaggctg | cgcaactgtt | gggaagggcg | atcggtgcgg | gcctcttcgc | tattacgcca | 420 |
| gctggcgaaa | gggggatgtg | ctgcaaggcg | attaagttgg | gtaacgccag | ggttttccca | 480 |
| gtcacgacgt | tgtaaaacga | cggccagaga | attcgagctc | ggtacctcgc | gaatacatct | 540 |
| agataggaac | ccctagtgat | ggagttggcc | actccctctc | tgcgcgctcg | ctcgctcact | 600 |
| gaggccgccc | gggcaaagcc | cgggcgtcgg | gcgacctttg | gtcgcccggc | ctcagtgagc | 660 |
| gagcgagcgc | gcagagaggg | agtggccaaa | gatctcttag | gtcagtgaag | agaagaacaa | 720 |
| aaagcagcat | attacagtta | gttgtcttca | tcaatcttta | aatatgttgt | gtggttttc | 780 |
| tctccctgtt | tccacagttt | ttcttgatca | tgaaaacgcc | aacaaaattc | tgaatcggcc | 840 |
| aaagaggtat | aattcaggta | aattggaaga | gtttgttcaa | gggaaccttg | agagagaatg | 900 |
| tatggaagaa | aagtgtagtt | ttgaagaagc | acgagaagtt | tttgaaaaca | ctgaaagaac | 960 |
| aactgaattt | tggaagcagt | atgttgatgg | agatcagtgt | gagtccaatc | catgtttaaa | 1020 |
| tggcggcagt | tgcaaggatg | acattaattc | ctatgaatgt | tggtgtccct | ttggatttga | 1080 |
| aggaaagaac | tgtgaattag | atgtaacatg | taacattaag | aatggcagat | gcgagcagtt | 1140 |
| ttgtaaaaat | agtgctgata | acaaggtggt | ttgctcctgt | actgagggat | atcgacttgc | 1200 |
| agaaaaccag | aagtcctgtg | aaccagcagt | gccatttcca | tgtggaagag | tttctgtttc | 1260 |
| acaaacttct | aagctcaccc | gtgctgagac | tgttttttcct | gatgtggact | atgtaaattc | 1320 |
| tactgaagct | gaaaccattt | tggataacat | cactcaaagc | acccaatcat | ttaatgactt | 1380 |
| cactcgggtt | gttggtggag | aagatgccaa | accaggtcaa | ttcccttggc | aggttgtttt | 1440 |
| gaatggtaaa | gttgatgcat | tctgtggagg | ctctatcgtt | aatgaaaaat | ggattgtaac | 1500 |
| tgctgcccac | tgtgttgaaa | ctggtgttaa | aattacagtt | gtcgcaggtg | aacataatat | 1560 |
| tgaggagaca | gaacatacag | agcaaaagcg | aaatgtgatt | cgaattattc | ctcaccacaa | 1620 |
| ctacaatgca | gctattaata | agtacaacca | tgacattgcc | cttctggaac | tggacgaacc | 1680 |
| cttagtgcta | aacagctacg | ttacacctat | ttgcattgct | gacaaggaat | acacgaacat | 1740 |
| cttcctcaaa | tttggatctg | gctatgtaag | tggctgggga | agagtcttcc | acaaagggag | 1800 |
| atcagcttta | gttcttcagt | acctagagt | tccacttgtt | gaccgagcca | catgtcttct | 1860 |
| atctacaaag | ttcaccatct | ataacaacat | gttctgtgct | ggcttccatg | aaggaggtag | 1920 |

```
agattcatgt caaggagata gtgggggacc ccatgttact gaagtggaag ggaccagttt    1980
cttaactgga attattagct ggggtgaaga gtgtgcaatg aaaggcaaat atggaatata    2040
taccaaggta tcccggtatg tcaactggat taaggaaaaa acaaagctca cttaacctcg    2100
actgtgcctt ctagttgcca gccatctgtt gtttgcccct cccccgtgcc ttccttgacc    2160
ctggaaggtg ccactcccac tgtcctttcc taataaaatg aggaaattgc atcgcattgt    2220
ctgagtaggt gtcattctat tctggggggt ggggtggggc aggacagcaa ggggaggat    2280 tgggaagaca atagcaggca tgctggggat gcggtgggct ctatggcttc tgaggcggaa    2340
agaaccagct ggggctctag ggggtatccc caaaaaacct cccacacctc cccctgaacc    2400
tgaaacataa aatgaatgca attgttgttg ttaacttgtt tattgcagct tataatggtt    2460
acaaataaag caatagcatc acaaatttca caaataaagc attttttca ctgcattcta    2520 gttgtggttt gtccaaactc atcaatgtat cttatcatgt ctgttaggtg agcttagtct    2580
tttcttttat ccaattcacg tagcgagaga ccttcgtata gatgccatat ttccccttca    2640
tcgcacattc ctcccccaa cttattatcc cggtcaagaa acttgttcct tcgacttcag    2700
tgacgtgtgg tccacctgaa tcaccttggc atgagtcgcg accgccctcg tgaaacccag    2760
cacaaaacat gttattgtaa atcgtaaatt tcgtggacag aagacaggtc gctctatcga    2820
ccaacgggac gcgcaaatat tgcagaacga gggctgatcg acctttgtgg aagacccgcc    2880
cccacccact cacatatccg ctcccaaatt tcaagaagat atttgtatat tctttatcgg    2940
ctatacaaat cggggtaaca taggagttaa gtacgagtgg ctcgtccagc tccaggaggg    3000
ctatatcatg gttgtacttg tttatagcgg cattataatt gtgatggggt atgatcctga    3060
taacattcct tttctgttca gtatgctcag tttcttcaat gttgtgttcg ccagccacga    3120
ccgtaatctt aaccccgtc tcgacacagt gtgcggccgt tacaatccac ttttcattga    3180
ctatggagcc cccacaaaac gcgtcgactt ttccgttgag caccacctgc catggaaatt    3240
ggccaggttt agcgtcctcg cccccgacaa ccctagtaaa gtcattaaat gactgtgtgg    3300
attgtgttat attatcaaga atcgtttcgg cttcagtaga gttaacgtag tccacatcgg    3360
gaaaaactgt ctcggccctt gtcaactttg atgtctggga cacacttacc cgaccgcacg    3420
ggaagggcac cgccggttca cagctctttt gattctcagc gagccggtag ccctcagtgc    3480
aactacacac aactttgttg tcggcggaat ttttacagaa ttgctcgcat cgtccatttt    3540
taatgttgca ggtgacgtcc aactcgcagt ttttccttc aaaaccaaaa gggcaccaac    3600
actcgtagga atttatatcg tctttacaac tcccccatt cagacatgga ttagattcgc    3660
attggtcccc atcgacatat tgcttccaga actcagtggt ccgttctgta ttctcaaaca    3720
cctcgcgcgc ttcttcaaaa ctgcattttt cctccataca ctctcgctcc aagttccctt    3780
gcacgaattc ttcaagcttt cctgagttat acctttagg ccggttaagt atcttattcg    3840
cgttttcgtg gtccagaaaa actgtggaaa cagggagaga aaaaccacac aacatattta    3900
aagattgatg aagacaacta actgtaatat gctgcttttt gttcttctct tcactgacct    3960
aagagatcta ggaaccccta gtgatggagt tggccactcc ctctctgcgc gctcgctcgc    4020
tcactgaggc cgcccgggca aagcccgggc gtcgggcgac ctttggtcgc ccggcctcag    4080
tgagcgagcg agcgcgcaga gagggagtgg ccaaactcgg atcccgggcc cgtcgactgc    4140
agaggcctgc atgcaagcgt ggtgtaatca tggtcatagc tgtttcctgt gtgaaattgt    4200
tatccgctca caattccaca caacatacga gccgaagca taaagtgtaa agcctggggt    4260
gcctaatgag tgagctaact cacattaatt gcgttgcgct cactgcccgc tttccagtcg    4320
```

```
ggaaacctgt cgtgccagct gcattaatga atcggccaac gcgcggggag aggcggtttg    4380
cgtattgggc gctcttccgc ttcctcgctc actgactcgc tgcgctcggt cgttcggctg    4440
cggcgagcgg tatcagctca ctcaaaggcg gtaatacggt tatccacaga atcaggggat    4500
aacgcaggaa agaacatgtg agcaaaaggc cagcaaaagg ccaggaaccg taaaaaggcc    4560
gcgttgctgg cgtttttcca taggctccgc cccctgacg agcatcacaa aaatcgacgc    4620
tcaagtcaga ggtggcgaaa cccgacagga ctataaagat accaggcgtt ccccctgga    4680 agctccctcg tgcgctctcc tgttccgacc ctgccgctta ccggatacct gtccgccttt    4740
ctcccttcgg gaagcgtggc gctttctcat agctcacgct gtaggtatct cagttcggtg    4800
taggtcgttc gctccaagct gggctgtgtg cacgaacccc ccgttcagcc cgaccgctgc    4860
gccttatccg gtaactatcg tcttgagtcc aacccggtaa gacacgactt atcgccactg    4920
gcagcagcca ctggtaacag gattagcaga gcgaggtatg taggcggtgc tacagagttc    4980
ttgaagtggt ggcctaacta cggctacact agaagaacag tatttggtat ctgcgctctg    5040
ctgaagccag ttaccttcgg aaaaagagtt ggtagctctt gatccggcaa acaaaccacc    5100
gctggtagcg gtggtttttt tgtttgcaag cagcagatta cgcgcagaaa aaaggatct    5160 caagaagatc ctttgatctt ttctacgggg tctgacgctc agtggaacga aaactcacgt    5220
taagggattt tggtcatgag attatcaaaa aggatcttca cctagatcct tttaaattaa    5280
aaatgaagtt ttaaatcaag cccaatctga ataatgttac aaccaattaa ccaattctga    5340
ttagaaaaac tcatcgagca tcaaatgaaa ctgcaattta ttcatatcag gattatcaat    5400
accatatttt tgaaaaagcc gtttctgtaa tgaaggagaa aactcaccga ggcagttcca    5460
taggatggca agatcctggt atcggtctgc gattccgact cgtccaacat caatacaacc    5520
tattaatttc ccctcgtcaa aaataaggtt atcaagtgag aaatcaccat gagtgacgac    5580
tgaatccggt gagaatggca aaagtttatg catttctttc cagacttgtt caacaggcca    5640
gccattacgc tcgtcatcaa aatcactcgc atcaaccaaa ccgttattca ttcgtgattg    5700
cgcctgagcg agacgaaata cgcgatcgct gttaaaagga caattacaaa caggaatcga    5760
atgcaaccgg cgcaggaaca ctgccagcgc atcaacaata ttttcacctg aatcaggata    5820
ttcttctaat acctggaatg ctgttttttcc ggggatcgca gtggtgagta accatgcatc    5880
atcaggagta cggataaaat gcttgatggt cggaagaggc ataaattccg tcagccagtt    5940
tagtctgacc atctcatctg taacatcatt ggcaacgcta cctttgccat gtttcagaaa    6000
caactctggc gcatcgggct tcccatacaa gcgatagatt gtcgcacctg attgcccgac    6060
attatcgcga gcccatttat acccatataa atcagcatcc atgttggaat ttaatcgcgg    6120
cctcgacgtt tcccgttgaa tatggctcat                                     6150
```

<210> SEQ ID NO 64
<211> LENGTH: 6901
<212> TYPE: DNA
<213> ORGANISM: Artificial Sequence
<220> FEATURE:
<223> OTHER INFORMATION: Synthetic

<400> SEQUENCE: 64

```
gaggcccttt cgtctcgcgc gtttcggtga tgacggtgaa aacctctgac acatgcagct      60
cccggagacg gtcacagctt gtctgtaagc ggatgccggg agcagacaag cccgtcaggg     120
cgcgtcagcg ggtgttggcg ggtgtcgggg ctggcttaac tatgcggcat cagagcagat     180
```

```
tgtactgaga gtgcaccata tgcggtgtga ataccgcac agatgcgtaa ggagaaaata      240
ccgcatcagg cgccattcgc cattcaggct gcgcaactgt tgggaagggc gatcggtgcg      300
ggcctcttcg ctattacgcc agctggcgaa agggggatgt gctgcaaggc gattaagttg      360
ggtaacgcca gggttttccc agtcacgacg ttgtaaaacg acggccagtg aattcgagct      420
cggtacccct gcaggcagct gcgcgctcgc tcgctcactg aggccgcccg ggcaaagccc      480
gggcgtcggg cgacctttgg tcgcccggcc tcagtgagcg agcgagcgcg cagagaggga      540
gtggccaact ccatcactag gggttcctcg gcaaagcca cgcgtactag ttattaatag       600
taatcaatta cggggtcatt agttcatagc ccatatatgg agttccgcgt tacataactt      660
acggtaaatg gcccgcctgg ctgaccgccc aacgaccccc gcccattgac gtcaataatg      720
acgtatgttc ccatagtaac gccaataggg actttccatt gacgtcaatg ggtggagtat      780
ttacggtaaa ctgcccactt ggcagtacat caagtgtatc atatgccaag tacgccccct      840
attgacgtca atgacggtaa atggcccgcc tggcattatg cccagtacat gaccttatgg      900
gactttccta cttggcagta catctacgta ttagtcatcg ctattaccat ggtcgaggtg      960
agccccacgt tctgcttcac tctccccatc tcccccccct ccccaccccc aattttgtat     1020
ttatttattt tttaattatt ttgtgcagcg atggggcgg ggggggggg gggcgcgcg       1080 ccaggcgggg cggggcgggg cgaggggcgg ggcggggcga ggcggagagg tgcggcggca     1140
gccaatcaga gcgcgcgct ccgaaagttt ccttttatgg cgaggcggcg gcggcggcgg     1200
ccctataaaa agcgaagcgc gcggcgggcg gggagtcgct gcgacgctgc cttcgccccg     1260
tgccccgctc cgccgccgcc tcgcgccgcc cgccccggct ctgactgacc gcgttactcc     1320
cacaggtgag cgggcgggac ggcccttctc ctccgggctg taattagcgc ttggtttaat     1380
gacggcttgt ttcttttctg tggctgcgtg aaagccttga ggggctccgg gagggccctt     1440
tgtgcggggg gagcggctcg ggggtgcgt gcgtgtgtgt gtgcgtgggg agcgccgcgt      1500
gcggctccgc gctgcccggc ggctgtgagc gctgcgggcg cggcgcgggg ctttgtgcgc     1560
tccgcagtgt gcgcgagggg agcgcggccg gggcggtgc cccgcggtgc gggggggct       1620 gcgaggggaa caaggctgc gtgcgggtg tgtgcgtggg gggtgagca gggggtgtgg       1680 gcgcgtcggt cgggctgcaa cccccctgc accccctcc ccgagttgct gagcacggcc       1740
cggcttcggg tgcggggctc cgtacgggc gtggcgcggg gctcgccgtg ccggcgggg      1800 ggtggcggca ggtgggggtg ccgggcgggg cggggccgcc tcgggccggg gagggctcgg     1860
gggaggggcg cggcggcccc cggagcgccg gcggctgtcg aggcgcggcg agccgcagcc     1920
attgcctttt atggtaatcg tgcgagaggg cgcagggact tcctttgtcc caaatctgtg     1980
cggagccgaa atctgggagg cgccgccgca ccccctctag cgggcgcggg gcgaagcggt     2040
gcggcgccgg caggaaggaa atgggcgggg agggccttcg tgcgtcgccg cgccgccgtc     2100
cccttctccc tctccagcct cggggctgtc cgcgggggga cggctgcctt cggggggac      2160 ggggcagggc ggggttcggc ttctggcgtg tgaccggcgg ctctagagcc tctgctaacc     2220
atgttcatgc cttcttcttt ttcctacagc tcctgggcaa cgtgctggtt attgtgctgt     2280
ctcatcattt tggcaaagaa ttcctcgaga tgcagcgcgt gaacatgatc atggcagaat     2340
caccaggcct catcaccatc tgccttttag gatatctact cagtgctgaa tgtacagttt     2400
ttcttgatca tgaaaacgcc aacaaaattc tgaatcggcc aaagaggtat aattcaggta     2460
aattggaaga gtttgttcaa gggaaccttg agagagaatg tatggaagaa agtgtagtt      2520 ttgaagaagc acgagaagtt tttgaaaaca ctgaaagaac aactgaattt tggaagcagt     2580
```

```
atgttgatgg agatcagtgt gagtccaatc catgtttaaa tggcggcagt tgcaaggatg    2640
acattaattc ctatgaatgt tggtgtccct ttggatttga aggaaagaac tgtgaattag    2700
atgtaacatg taacattaag aatggcagat gcgagcagtt ttgtaaaaat agtgctgata    2760
acaaggtggt ttgctcctgt actgagggat atcgacttgc agaaaaccag aagtcctgtg    2820
aaccagcagt gccatttcca tgtggaagag tttctgtttc acaaacttct aagctcaccc    2880
gtgctgagac tgttttttcct gatgtggact atgtaaattc tactgaagct gaaaccattt    2940
tggataacat cactcaaagc acccaatcat ttaatgactt cactcgggtt gttggtggag    3000
aagatgccaa accaggtcaa ttcccttggc aggttgtttt gaatggtaaa gttgatgcat    3060
tctgtggagg ctctatcgtt aatgaaaaat ggattgtaac tgctgcccac tgtgttgaaa    3120
ctggtgttaa aattacagtt gtcgcaggtg aacataatat tgaggagaca gaacatacag    3180
agcaaaagcg aaatgtgatt cgaattattc ctcaccacaa ctacaatgca gctattaata    3240
agtacaacca tgacattgcc cttctggaac tggacgaacc cttagtgcta aacagctacg    3300
ttacacctat ttgcattgct gacaaggaat acacgaacat cttcctcaaa tttggatctg    3360
gctatgtaag tggctgggga agagtcttcc acaaagggag atcagcttta gttcttcagt    3420
accttagagt tccacttgtt gaccgagcca catgtcttcg atctacaaag ttcaccatct    3480
ataacaacat gttctgtgct ggcttccatg aaggaggtag agattcatgt caaggagata    3540
gtgggggacc ccatgttact gaagtggaag ggaccagttt cttaactgga attattagct    3600
ggggtgaaga gtgtgcaatg aaaggcaaat atggaatata taccaaggta tcccggtatg    3660
tcaactggat taaggaaaaa acaaagctca cttaagcggc cgcgtttaaa ctcaacctct    3720
ggattacaaa atttgtgaaa gattgactgg tattcttaac tatgttgctc cttttacgct    3780
atgtggatac gctgctttaa tgcctttgta tcatgctatt gcttcccgta tggctttcat    3840
tttctcctcc ttgtataaat cctggttgct gtctctttat gaggagttgt ggcccgttgt    3900
caggcaacgt ggcgtggtgt gcactgtgtt tgctgacgca acccccactg gttggggcat    3960
tgccaccacc tgtcagctcc tttccgggac tttcgctttc ccctcccta ttgccacggc    4020 ggaactcatc gccgcctgcc ttgcccgctg ctggacaggg gctcggctgt tgggcactga    4080
caattccgtg gtgttgtcgg ggaaatcatc gtccttttcct tggctgctcg cctgtgttgc    4140
cacctggatt ctgcgcggga cgtccttctg ctacgtccct tcggccctca atccagcgga    4200
ccttccttcc cgcggcctgc tgccggctct gcggcctctt ccgcgtcttc gccttcgccc    4260
tcagacgagt cggatctccc tttgggccgc ctccccgcag aattcctgca gctagttgcc    4320
agccatctgt tgtttgcccc tcccccgtgc cttccttgac cctggaaggt gccactccca    4380
ctgtcctttc ctaataaaat gaggaaattg catcgcattg tctgagtagg tgtcattcta    4440
ttctgggggg tggggtgggg caggacagca agggggagga ttgggaagac aatagcaggc    4500
atgctgggga tgcggtgggc tctatggggt aaccaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagctgcct gcaggaagct    4680
tggcgtaatc atggtcatag ctgtttcctg tgtgaaattg ttatccgctc acaattccac    4740
acaacatacg agccggaagc ataaagtgta aagcctgggg tgcctaatga gtgagctaac    4800
tcacattaat tgcgttgcgc tcactgcccg ctttccagtc gggaaacctg tcgtgccagc    4860
tgcattaatg aatcggccaa cgcgcgggga gaggcggttt gcgtattggg cgctcttccg    4920
```

```
cttcctcgct cactgactcg ctgcgctcgg tcgttcggct gcggcgagcg gtatcagctc    4980
actcaaaggc ggtaatacgg ttatccacag aatcagggga taacgcagga aagaacatgt    5040
gagcaaaagg ccagcaaaag gccaggaacc gtaaaaaggc cgcgttgctg gcgttttcc     5100 ataggctccg ccccctgac gagcatcaca aaaatcgacg ctcaagtcag aggtggcgaa     5160
acccgacagg actataaaga taccaggcgt ttccccctgg aagctccctc gtgcgctctc    5220
ctgttccgac cctgccgctt accggatacc tgtccgcctt tctcccttcg ggaagcgtgg    5280
cgctttctca tagctcacgc tgtaggtatc tcagttcggt gtaggtcgtt cgctccaagc    5340
tgggctgtgt gcacgaaccc cccgttcagc ccgaccgctg cgccttatcc ggtaactatc    5400
gtcttgagtc caacccggta agacacgact tatcgccact ggcagcagcc actggtaaca    5460
ggattagcag agcgaggtat gtaggcggtg ctacagagtt cttgaagtgg tggcctaact    5520
acggctacac tagaaggaca gtatttggta tctgcgctct gctgaagcca gttaccttcg    5580
gaaaaagagt tggtagctct tgatccggca aacaaaccac cgctggtagc ggtggttttt    5640
ttgtttgcaa gcagcagatt acgcgcagaa aaaaaggatc tcaagaagat cctttgatct    5700
tttctacggg gtctgacgct cagtggaacg aaaactcacg ttaagggatt ttggtcatga    5760
gattatcaaa aaggatcttc acctagatcc ttttaaatta aaaatgaagt tttaaatcaa    5820
tctaaagtat atatgagtaa acttggtctg acagttacca atgcttaatc agtgaggcac    5880
ctatctcagc gatctgtcta tttcgttcat ccatagttgc ctgactcccc gtcgtgtaga    5940
taactacgat acgggagggc ttaccatctg gccccagtgc tgcaatgata ccgcgagacc    6000
cacgctcacc ggctccagat ttatcagcaa taaaccagcc agccggaagg gccgagcgca    6060
gaagtggtcc tgcaacttta tccgcctcca tccagtctat taattgttgc cgggaagcta    6120
gagtaagtag ttcgccagtt aatagtttgc gcaacgttgt tgccattgct acaggcatcg    6180
tggtgtcacg ctcgtcgttt ggtatggctt cattcagctc cggttcccaa cgatcaaggc    6240
gagttacatg atcccccatg ttgtgcaaaa aagcggttag ctccttcggt cctccgatcg    6300
ttgtcagaag taagttggcc gcagtgttat cactcatggt tatggcagca ctgcataatt    6360
ctcttactgt catgccatcc gtaagatgct tttctgtgac tggtgagtac tcaaccaagt    6420
cattctgaga atagtgtatg cggcgaccga gttgctcttg cccggcgtca atacgggata    6480
ataccgcgcc acatagcaga actttaaaag tgctcatcat tggaaaacgt tcttcggggc    6540
gaaaactctc aaggatctta ccgctgttga gatccagttc gatgtaaccc actcgtgcac    6600
ccaactgatc ttcagcatct tttactttca ccagcgtttc tgggtgagca aaaacaggaa    6660
ggcaaaatgc cgcaaaaaag ggaataaggg cgacacggaa atgttgaata ctcatactct    6720
tcctttttca atattattga agcatttatc agggttattg tctcatgagc ggatacatat    6780
ttgaatgtat ttagaaaaat aaacaaatag gggttccgcg cacatttccc cgaaaagtgc    6840
cacctgacgt ctaagaaacc attattatca tgacattaac ctataaaaat aggcgtatca    6900
c                                                                    6901
```